US010612039B2

(12) United States Patent
Bramlett et al.

(10) Patent No.: US 10,612,039 B2
(45) Date of Patent: Apr. 7, 2020

(54) COMPOSITIONS AND METHODS FOR CONTOLLING PLANT PESTS

(71) Applicant: SYNGENTA PARTICIPATIONS AG, Basel (CH)

(72) Inventors: Matthew Richard Bramlett, Research Triangle Park, NC (US); Katherine Seguin, Research Triangle Park, NC (US); Vance Cary Kramer, Research Triangle Park, NC (US); Mark Scott Rose, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 16/524,873

(22) Filed: Jul. 29, 2019

(65) Prior Publication Data

US 2019/0345514 A1 Nov. 14, 2019

Related U.S. Application Data

(62) Division of application No. 15/534,074, filed as application No. PCT/US2015/063610 on Dec. 3, 2015, now Pat. No. 10,407,693.

(60) Provisional application No. 62/090,899, filed on Dec. 12, 2014.

(51) Int. Cl.
C12N 15/82 (2006.01)
C07K 14/325 (2006.01)
C07H 21/00 (2006.01)

(52) U.S. Cl.
CPC ......... *C12N 15/8286* (2013.01); *C07H 21/00* (2013.01); *C07K 14/325* (2013.01); *Y02A 40/162* (2018.01)

(58) Field of Classification Search
None
See application file for complete search history.

(56) References Cited

U.S. PATENT DOCUMENTS 788,471 A 4/1905 Jenkins
10,093,946 B2 * 10/2018 Lehtinen ............... C07K 14/325

2005/0097635 A1 5/2005 Lambert
2005/0138685 A1 6/2005 Flannagan et al.
2009/0238798 A1 9/2009 Bogdanova et al.
2010/0256051 A1 10/2010 Isaac et al.
2014/0056866 A1 2/2014 Andersch et al.

FOREIGN PATENT DOCUMENTS

| WO | 94/05771 A2 | 3/1994 |
| WO | 1998/00546 A2 | 1/1998 |
| WO | 99/33991 A2 | 7/1999 |
| WO | 01/19859 A2 | 3/2001 |
| WO | 2009/158470 A2 | 12/2009 |
| WO | 2013/134734 A2 | 9/2013 |
| WO | 2015/088937 A2 | 6/2015 |

OTHER PUBLICATIONS

International Search Report and Written Opinion for International Application No. PCT/US2015/063610 dated Dec. 3, 2015.
The Partial Supplemtary European Search Report EP15867122.2 dated May 29, 2018.
Database GENPEPT (Online) NCBI; Jun. 13, 2014, "Hypothetical protein (Paenibacillus taiwanesis)" Database accession No. WP_028546603.
Database EMBL (Online) Jun. 10, 1991, "B. Thuringiensis DNA for pseudooperon cryX-cryIG", retrieved from EBOI acession No. EMBL: X58120.
Extended European Search Report for EP Application No. 15867122.2 dated Sep. 17, 2018.
Database GenPept (Online) NCBI; "Hypothetical Protein (Paenibacillus taiwanesis)", XP002780287.
Lambert et al. 2005, Genbank CAA85764.1.
Li et al., Environmental Science and Technology, vol. 41, pp. 6052-6058, 2007.
Howe et al., Molecular Breeding, vol. 10, pp. 153-164, 2002.

* cited by examiner

*Primary Examiner* — Matthew R Keogh
(74) *Attorney, Agent, or Firm* — Gregory Warren

(57) ABSTRACT

Novel insecticidal proteins isolated from *Bacillus thuringiensis* that are active against lepidopteran insect pests are disclosed. The DNA encoding the insecticidal proteins can be used to transform various prokaryotic and eukaryotic organisms to express the insecticidal proteins. These recombinant organisms can be used to control lepidopteran insects in various environments.

16 Claims, No Drawings
Specification includes a Sequence Listing.

SEQUENCE LISTING

<160> NUMBER OF SEQ ID NOS: 26

<210> SEQ ID NO 1
<211> LENGTH: 3444
<212> TYPE: DNA
<213> ORGANISM: Bacillus thuringiensis

<400> SEQUENCE: 1

```
atggatttag acggtaataa aactgaaact gagactgaaa ttgtaaatgg ttccgaaagt      60
agtatcgatc catcaagcgt gtcttatgcg ggaaataaca gctattcttc cgctttgaat     120
ctcaattctt gtcaaaacag agggattgca cagtgggtta atacgcttgg aggtgcaatc     180
ggtcaggctg tatccatagg aacatccatc atttccttgc ttgcggcgcc tacgcttact     240
ggaagtattt cgttagcttt taatcttata aggagaatgg ggacaggcag taatggaagc     300
tctatttcgg acttgtcaat atgtgactta ctatccataa ttaatttacg tgtaagtcaa     360
gctgtattga acgacgggat tgcagatttt aacggctcag tggctgtata tgatctctat     420
ttgcatgctt tacgcagttg gaacaataac cctaatgctg ctaccgcgga ggaacttcgc     480
actcgttttc gtattgcaga ttccgaattc gaacgtatct taacgcgggg gtccttgaca     540
catggtggtt cattagctag acaagatgct caagtgttac tgttaccttc ttttgtaaat     600
gctgcctatc ttcatttact tatattaagg gatgctagca gatatggggc tagctggggc     660
ttgtttaata cgacaccaca tatcaattat ccagtaagat tacaacaact tattggttct     720
tatacccatt actgcacaca ttggtataat caaggtttaa atgaaatcag acaacgaggc     780
aatacggctg tcaattggtt ggaatttcat agatacagaa gagatatgac attaatggta     840
ctagatgttg tgtcattatt ttcagcgctt gatactataa ggtatccgaa cgcaaccgtt     900
gtccaattaa gcagaaccgt ttatacagac ccgattggtt ttgtaaatcg tggaagcggc     960
aacagattaa gctggtttga ttggcggaat caagctaatt tttcaacgct agaaagtgaa    1020
atgccaaccc cctcgtctcc actttctttg aatcatatga gtatatttac gggtcccctt    1080
actttacctg tctctcctaa tacccataga gccagggtat ggtatggcaa tcaaaatatg    1140
ttcacaacgg gtagtcaaaa ttcaggtcaa acaacaaact ctattcaaaa catttcgggt    1200
```

```
ttagaaatat ttagaataga ttctcaagcc tgtaatctaa acaataattc gtatggcgtg    1260
aaccgagctg aatttttca tggcgctagt cagggctccc aaagatctgt ttatcaaggc    1320
tatattagac aaagtggatt ggacaacccg gtagttatga atcttcaaag cttttttacct   1380 ggcgaaaatt cagcgacacc aaccgcacaa gattatacgc atatattaag taatcctgtt   1440
aatataagag gaggacttcg acaaatagta gctgatcgtc gttcttctgt agtcgtttat   1500
ggttggacac acaaaagttt gagtcgacgt agtttagttg caccagatca aattactcaa   1560
gtacctgctg ttaaagcaag tccctcatcc cattgtacca tcattgcagg acctggattt   1620
acgggcgggg atctcgtaag tctgcaacca atggacaac tcgttatacc gtttcaggta    1680
tcggcgccag aaacaaatta tcatattcga atatgttatg tttctacgtc cgactgttcc   1740
ataaatacaa tatgtaatga tgagacccat ttaagtacgt tgccttccac aacctcatca   1800
cttgaaaatt tacaatgtaa ccatttgcat tattttaacg tgggcacttt caaacctacg   1860
atagatagta aactaacgct tgtaaataca agtccaaatg caaatattat catcgacaaa   1920
attgaattta ttcccgtaga tacggcccaa caacaaaatg aggatctaga agcagcaaaa   1980
aaagcggtgg cgagcttgtt tacacgcaca agggacggat tacaagtaaa tgtgaaagat   2040
tatcaagtcg atcaagcggc aaatttagtg tcatgcttat cagatgaaca atatgggtat   2100
gacaaaaaga tgttattgga agcggtacgt gcggcaaaac gacttagccg agaacgcaac   2160
ttacttcagg acccagattt taatacaatc aatagtacag aagaaaatgg atggaaagca   2220
agtaacggcg ttactattag tgagggcggg ccattctata aaggccgtgc aattcagcta   2280
gcaagtgcac gagaaaatta cccaacatac atctatcaaa aagtagatgc atcggagtta   2340
aagccgtata cacgttatag actggatggg ttcgtgaaga gtagtcaaga tttagaaatt   2400
gatctcattc accatcataa agtccatctt gtgaaaaatg taccagataa tttagtatct   2460
gatacttacc cagatgattc ttgtagtgga atcaatcgat gtcaggaaca acagatggta   2520
aatgcgcaac tggaaacaga gcatcatcat ccgatggatt gctgtgaagc agctcaaaca   2580
catgagtttt cttcctatat tgatacaggg gatttaaatt cgagtgtaga ccagggaatc   2640
tgggcgatct ttaaagttcg aacaaccgat ggttatgcga cgttaggaaa tcttgaattg   2700
gtagaggtcg gaccgttatc gggtgaatct ttagaacgtg aacaaaggga taatacaaaa   2760
tggagtgcag agctaggaag aaagcgtgca gaaacagatc gcgtgtatca agatgccaaa   2820
caatccatca atcatttatt tgtggattat caagatcaac aattaaatcc agaaataggg   2880
atggcagata ttatggacgc tcaaaatctt gtcgcatcaa tttcagatgt atatagcgat   2940
gccgtactgc aaatccctgg aattaactat gagatttaca cagagctgtc caatcgctta   3000
caacaagcat cgtatctgta tacgtctcga atgcggtgc aaaatgggga ctttaacaac    3060
gggctagata gctggaatgc aacagcgggt gcatcggtac aacaggatgg caatacgcat   3120
ttcttagttc tttctcattg ggatgcacaa gtttctcaac aatttagagt gcagccgaat   3180
tgtaaatatg tattacgtgt aacagcagag aaagtaggcg gcggagacgg atacgtgact   3240
atccgggatg atgctcatca tacagaaacg cttacattta atgcatgtga ttatgatata   3300
aatggcacgt acgtgactga taatacgtat ctaacaaaag aagtggtatt ccatccggag   3360
acacaacaca tgtgggtaga ggtaaatgaa acagaaggtg catttcatat agatagtatt   3420
gaattcgttg aaacagaaaa gtaa                                          3444
```

<210> SEQ ID NO 2

<211> LENGTH: 3474
<212> TYPE: DNA
<213> ORGANISM: Bacillus thuringiensis

<400> SEQUENCE: 2

| | | | | | |
|---|---|---|---|---|---|
| atgaatcgaa | ataatcaaaa | tgaatatgaa | attattgatg | cccccattg | tgggtgtcca | 60 |
| tcagatgacg | atgtgaagta | tcctttggca | agtgacccaa | atgcagcgtt | acaaaatatg | 120 |
| aactataaag | attacttaca | aatgacagat | gaggactaca | ctgattctta | tataaatcct | 180 |
| agtttatcta | ttagtggtag | agatgcagtt | cagactgcgc | ttactgttgt | tgggagaata | 240 |
| ctcggggctt | taggtgttcc | gttttctgga | caaatagtga | ttttttatca | attccttta | 300 |
| aatacactgt | ggccagttaa | tgatacagct | atatgggaag | ctttcatgcg | acaggtggag | 360 |
| gaacttgtca | atcaacaaat | aacagaattt | gcaagaaatc | aggcacttgc | aagattgcaa | 420 |
| ggattaggag | attcttttaa | tgtatatcaa | cgttcccttc | aaaattggtt | ggctgatcga | 480 |
| aatgatacac | gaaatttaag | tgttgttcgt | gctcaattta | tagctttaga | ccttgatttt | 540 |
| gttaatgcta | ttccattgtt | tgcagtaaat | ggacagcagg | ttccattact | gtcagtatat | 600 |
| gcacaagctg | tgaatttaca | tttgttatta | ttaaaagatg | catctctttt | tggagaagga | 660 |
| tggggattca | cacagggga | aatttccaca | tattatgacc | gtcaattgga | actaaccgct | 720 |
| aggtacacta | attactgtga | aacttggtat | aatacaggtt | tagatcgttt | aagaggaaca | 780 |
| aatactgaaa | gttggttaag | atatcatcaa | ttccgtagag | aaatgacttt | agtggtatta | 840 |
| gatgttgtgg | cgctatttcc | atattatgat | gtacgacttt | atccaacggg | atcaaaccca | 900 |
| cagcttacac | gtgaggtata | tacagatccg | attgtattta | tccaccagc | taatgttgga | 960 |
| ctttgccgac | gttggggtac | taatccctat | aatacttttt | ctgagctcga | aaatgccttc | 1020 |
| attcgcccac | cacatctttt | tgataggctg | aatagcttaa | caatcagcag | taatcgattt | 1080 |
| ccagtttcat | ctaattttat | ggattattgg | tcaggacata | cgttacgccg | tagttatctg | 1140 |
| aacgattcag | cagtacaaga | agatagttat | ggcctaatta | caaccacaag | agcaacaatt | 1200 |
| aatcccggag | ttgatggaac | aaaccgcata | gagtcaacgg | cagtagattt | tcgttctgca | 1260 |
| ttgataggta | tatatggcgt | gaatagagct | tcttttgtcc | caggaggctt | gtttaatggt | 1320 |
| acgacttctc | ctgctaatgg | aggatgtaga | gatctctatg | atacaaatga | tgaattacca | 1380 |
| ccagatgaaa | gtaccggaag | ttcaacccat | agactatctc | atgttacctt | ttttagcttt | 1440 |
| caaactaatc | aggctggatc | tatagctaat | gcaggaagtg | tacctactta | tgtttggacc | 1500 |
| cgtcgtgatg | tggaccttaa | taatacgatt | accccaaata | gaattacaca | attaccattg | 1560 |
| gtaaaggcat | ctgcacctgt | ttcgggtact | acggtcttaa | aaggtccagg | atttacagga | 1620 |
| ggggtatac | tccgaagaac | aactaatggc | acatttggaa | cgttaagagt | aacggttaat | 1680 |
| tcaccattaa | cacaacaata | tcgcctaaga | gttcgttttg | cctcaacagg | aaatttcagt | 1740 |
| ataaggttac | tccgtggagg | ggtttctatc | ggtgatgtta | gattagggag | cacaatgaac | 1800 |
| agagggcagg | aactaactta | cgaatccttt | ttcacaagag | agtttactac | tactggtccg | 1860 |
| ttcaatccgc | ctttacatt | tacacaagct | caagagattc | taacagtgaa | tgcagaaggt | 1920 |
| gttagcaccg | tggtgaata | ttatatgat | agaattgaaa | ttgtccctgt | gaatccggca | 1980 |
| cgagaagcgg | aagaggattt | agaagcggcg | aagaaagcgg | tggcgagctt | gtttacacgt | 2040 |
| acaagagatg | gattacaggt | aaatgtgaca | gattaccaag | tggatcgagc | ggcaaattta | 2100 |
| gtgtcatgct | tatcagatga | acaatattcg | catgataaaa | agatgttatt | ggaagccgta | 2160 |
| cgcgcagcaa | aacgcctcag | ccgcgaacgc | aacttacttc | aagatccaga | ttttaataca | 2220 |

```
atcaatagta cagaagaaaa tggctggaag gcaagtaacg gtgttactat tagcgagggc   2280
ggtccattct ttaaaggtcg tgcacttcag ttagcaagcg caagagaaaa ttatccaaca   2340
tacatttatc aaaaagtaga tgcatcggtg ttaaagcctt atacacgcta tagactagat   2400
ggatttgtga agagtagtca agatttagaa attgatctca tccaccatca taaagtccat   2460
cttgtaaaaa atgtaccaga taatttagta tctgatactt actcagatgg ttcttgcagc   2520
ggaatcaacc gttgtgatga acagcagcag gtagatatgc agctagatgc ggagcatcat   2580
ccaatggatt gctgtgaagc ggctcaaaca catgagtttt cttcctatat taatacaggg   2640
gatctaaatg caagtgtaga tcagggcatt tgggttgtat taaaagttcg aacaacagat   2700
gggtatgcga cgttaggaaa tcttgaattg gtagaggttg ggccattatc gggtgaatct   2760
ctagaacgcg aacaaagaga taatgcgaaa tggaatgcag agctaggaag aaagcgtgca   2820
gaaacagatc gcgtgtatct agctgcgaaa caagcaatta atcatctatt tgtagactat   2880
caagatcaac aattaaatcc agaaattggg ctagcggaaa taaatgaagc ttcaaatctt   2940
gtgaagtcaa tttcgggtgt atatagtgat acactattac agattcctgg aattaactac   3000
gaaatttaca cagagttatc cgatcgatta caacaagcat cgtatctgta tacgtctcga   3060
aatgccgtgc aaaatggaga ctttaacagt ggtctagata gttggaatgc aacaacagat   3120
gcatcggttc agcaagatgg cagtacacat ttcttagttc tttcgcattg ggatgcacaa   3180
gtttcccaac aaatgagagt aaatttgaat tgtaagtatg ttttacgtgt aacagcaaaa   3240
aaagtaggag gcggagatgg atacgtcaca atccgagatg gcgctcatca ccaagaaact   3300
cttacattta atgcatgtga ctacgatgta aatggtacgt atgtcaatga caattcgtac   3360
ataacaaaag aagtggtatt ctacccagag acaaaacata tgtgggtaga ggtgagtgaa   3420
tccgaaggtt cattctatat agacagtatt gagtttattg aaacacaaga gtag         3474
```

<210> SEQ ID NO 3
<211> LENGTH: 3522
<212> TYPE: DNA
<213> ORGANISM: Bacillus thuringiensis

<400> SEQUENCE: 3

```
atgaatcgaa ataatcaagg tgaatatgaa attattgacg cttccacttg tggttgttcg     60
tcagatgatg ttgttcaata tcctttggca agagatccga atgctgcatt ccaaaatatg    120
aattataaag attatttgaa aatgtctgac ggagactacg tcgattctta tataaaccca    180
ggcttatcta ttggtcgtag agatgtgacc ctaactggag ttggtattgt tgcgctaata    240
gtagggactt taggtggtcc agttgggggt atagtaactg gcttgatttc ctctctttta    300
ggattattgt ggccaagtaa tgataatgat gtatgggaag cttttatggc acaaatagaa    360
gagctaattg aacaaaggat agcagatcaa gtagtaagga atgcactcga taacttaact    420
ggattgcgcg attattataa tcaataccta ttagcattgg aggagtggca ggaaaggccg    480
aacgctgtaa gatctacctt agtttttaat agatttgaaa ccctgcattc tcactttgta    540
actagtatgc caagctttgg tagtggccct ggaagtgaaa ggtatgcggt acaattgctg    600
acagtttatg cacaagcggc aaatctgcat ttgttattat taagagatgc tgacatttat    660
ggggcaaggt ggggacttcg tgaatctcag attgatttat attttaatga gctacaaaat    720
cgtactcgag attataccaa tcattgtgta actgcgtaca ataatgggtt agaggagata    780
cgaggaacaa gccctgcaag ttggttgagg taccatcaat tccgtagaga gacaacacta    840
```

```
atagcattgg atttagtggc gatattccca tattacaacg tacgagaata tccaattggg    900
gtaaatcctc agcttacacg tgatgtatat acagatccaa tagggggttac tttcagaaga    960
gaagattggg aaacaggagt agaatgcaga ccatgggtaa atactcctta catgagcttt   1020
tcggatcttg aaaatgcaat aattcgtcca ccacatctat ttgaaacatt acgtaattta   1080
acaattcata caggtcgata taacctagta ggaggggcga gatttattga aggatgggtc   1140
ggacattctg taacaaatac tcgcttgggt aattcaacag tatttacaag taattatggt   1200
tctttgccac ctcgttttca agttttaaat tttactaatt ttgatgttta ccaaattaat   1260
acgagagcag attctacagg taccttagga atccctggat ttgcagttac aagggcccaa   1320
ttcattccgg gtgggactta ttcagtagct caccgagatc caggggcatg tcaacaagat   1380
tatgattcaa ttgaagagtt accaagtcta gacccggatg aacctattaa tagaagttat   1440
agtcatagat tatcgcatgt tacccttat aaatatactc tctcagatac agattatgga   1500
gttatcaatt atacagatta tggaagtatg cctgcatatg tctggacaca tcgcgatgtg   1560
gaccttacta acacgattac tgcagataga attacacaac tcccattagt aaaggcatct   1620
acactacctg cgggtactac tgtggtaaaa ggcccaggat ttacaggagg agatatactc   1680
cgaagaacaa ctaatggaac atttgggaca ttacatgtaa gggttaattc accattaaca   1740
caacaatatc gcctaagagt tcgttttgcc tcaacaggaa atttcagtat aagggtactc   1800
cgtggaggga cttctatcgg tgatgctaga tttgggagca caatgaacag aggacaggaa   1860
ctaacttacg aatcctttgt cacaagagag tttactacta ctggtccgtt caatccgcct   1920
tttacattta cacaaactca agaaattcta acagtgaatg cagaaggtgt tagcaccggt   1980
ggtgaatatt atatagatag tattgagatt gttcctgtaa atccgacgcg agaggcggaa   2040
gaggatctag aagcagcgaa gaaagcggtg gcgagcttgt ttacacgtac aagggacgga   2100
ttacaagtaa atgtgacaga ttaccaagtg gatcgagcgg caaatttagt gttatgctta   2160
tcagatgaac aatatgcgca tgataaaaag atgttattgg aagccgtacg cgcagccaaa   2220
cgactcagcc gcgagcgtaa cttgcttcaa gatccagatt tcaatgaaat aaatagtacg   2280
gaagatagtg ttggaagac aagtaacggc attatcatta gtgagggtgg tccattcttt   2340
aaaggtcgtg cccttcagct agcaagcgca cgtgaaaatt acccaacata catctatcaa   2400
aaggtagact catcaatgtt aaaaccttat acacgtata aactagatgg atttgtgcaa   2460
agtagtcaag atttagaaat tgaactcatt caccatcata aagtccacct cgtgaaaaat   2520
gtaccagata atttagtact tgatacttac ccagatggtt cttgcaacgg aattaaccga   2580
tgtgaggaac aacagatggt gaattcgcaa ctagaaacag aacatcatcc aatggattgc   2640
tgtgaagcat cccaaacaca tgagttttct tcctatattc atacaggtga cctaaatgca   2700
agtgtagatc aaggcatttg ggttgtattg aagattcgga caacagatgg ttctgcgacg   2760
ttaggaaatc ttgaattggt agaggttggt ccattatcgg gtgaatctct agaacgtgaa   2820
caaagagata atgcgaaatg gaatgcagag ttaggaagga agcgtgcaga agcagatcgc   2880
gtgtatcaag gtgcgaaaca agcaattaac catctatttg tagactatca agatcaacaa   2940
ttaaatccag aagttgggct agcagaaatt agtgaagctc gaaatcttat cgaatcaatt   3000
tcagatgtat attgcgatgc agtactgcga attcctggaa ttaactacga gatgtataca   3060
gagttatcta atcgtctaca acaagcagcg tatctgtata cgtctcgaaa tgccgtgcaa   3120
aacgggact taacagcgg tttagatagt tggaatgcaa caactgatgc gacggttcag   3180
caggatggca atatgtattt cttagttctt tcccattggg atgcacaagt ttctcaacaa   3240
```

```
tttagagtac agccgaattg taaatatgtg ttacgtgtga cagcgaagaa agtagggaac    3300
ggagatggat atgttacgat ccaagatggc gctcatcacc gagaaacact tacattcaat    3360
gcatgtgact acgatgtaaa tggtacgcat gtaaatgaca attcgtatat tacaaaagaa    3420
ttggagttct atccaaagac agaacatatg tgggtagagg taagtgaaac agaaggtacc    3480
ttctatatag acagcattga gctaattgaa acacaagagt ag                      3522
```

<210> SEQ ID NO 4
<211> LENGTH: 3540
<212> TYPE: DNA
<213> ORGANISM: Bacillus thuringiensis

<400> SEQUENCE: 4

```
atgggaggaa aaagtatgaa tcgaaataat caaggtgaat atgaaattat tgacgcttcc      60
acttgtggtt gttcgtcaga tgatgttgtt caatatcctt tggcaagaga tccgaatgct     120
gcattccaaa atatgaatta taagattat ttgaaaatgt ctgacggaga ctacgtcgat      180
tcttatataa acccaggctt atctattggt cgtagagatg tgaccctaac tggagttggt    240
attgttgcgc taatagtagg gactttaggt ggtccagttg ggggtatagt aactggcttg    300
atttcctctc ttttaggatt attgtggcca agtaatgata atgatgtatg ggaagctttt    360
atggcacaaa tagaagagct aattgaacaa aggatagcag atcaagtagt aaggaatgca    420
ctcgataact taactggatt gcgcgattat tataatcaat acctattagc attggaggag    480
tggcaggaaa ggccgaacgc tgtaagatct accttagttt ttaatagatt tgaaaccctg    540
cattctcact ttgtaactag tatgccaagc tttggtagtg gccctggaag tgaaaggtat    600
gcggtacaat tgctgacagt ttatgcacaa gcggcaaatc tgcatttgtt attattaaga    660
gatgctgaca tttatggggc aaggtgggga cttcgtgaat ctcagattga tttatatttt    720
aatgagctac aaaatcgtac tcgagattat accaatcatt gtgtaactgc gtacaataat    780
gggttagagg agatacgagg aacaagccct gcaagttggt tgaggtacca tcaattccgt    840
agagagacaa cactaatagc attggattta gtgcgatat cccatatta caacgtacga      900 gaatatccaa ttggggtaaa tcctcagctt acacgtgatg tatatacaga tccaataggg    960
gttactttca gaagagaaga ttgggaaaca ggagtagaat gcagaccatg ggtaaatact    1020
ccttacatga gcttttcgga tcttgaaaat gcaataattc gtccaccaca tctatttgaa    1080
acattacgta atttaacaat tcatacaggt cgatataacc tagtaggagg ggcgagattt    1140
attgaaggat gggtcggaca ttctgtaaca aatactcgct tgggtaattc aacagtattt    1200
acaagtaatt atggttcttt gccacctcgt tttcaagttt ttaattttac taattttgat    1260
gtttaccaaa ttaatacgag agcagattct acaggtacct tagaatccc tggatttgca    1320 gttacaaggg cccaattcat tccgggtggg acttattcag tagctcaccg agatccaggg    1380
gcatgtcaac aagattatga ttcaattgaa gagttaccaa gtctagaccc ggatgaacct    1440
attaatagaa gttatagtca tagattatcg catgttaccc tttataaata tactctctca    1500
gatacagatt atggagttat caattataca gattatggaa gtatgcctgc atatgtctgg    1560
acacatcgcg atgtggacct tactaacacg attactgcag atagaattac acaactccca    1620
ttagtaaagg catctacact acctgcgggt actactgtgg taaaaggccc aggatttaca    1680
ggaggagata tactccgaag aacaactaat ggaacatttg gacattaca tgtaagggtt    1740 aattcaccat taacacaaca atatcgccta agagttcgtt ttgcctcaac aggaaatttc    1800
```

```
agtataaggg tactccgtgg agggacttct atcggtgatg ctagatttgg gagcacaatg      1860
aacagaggac aggaactaac ttacgaatcc tttgtcacaa gagagtttac tactactggt      1920
ccgttcaatc cgccttttac atttacacaa actcaagaaa ttctaacagt gaatgcagaa      1980
ggtgttagca ccggtggtga atattatata gatagtattg agattgttcc tgtaaatccg      2040
acgcgagagg cggaagagga tctagaagca gcgaagaaag cggtggcgag cttgtttaca      2100
cgtacaaggg acggattaca agtaaatgtg acagattatc aagtcgatca agcggcaaat      2160
ttagtgtcat gcttatcaga tgaacaatat gggtatgaca aaaagatgtt attggaagcg      2220
gtacgcgcgg caaaacgcct cagccgagaa cgtaacttac ttcaagatcc agattttaat      2280
acaatcaata gtacagaaga aaatggatgg aaagcaagta acggcgttac tattagtgag      2340
ggcggtccat tctataaagg ccgtgcactt cagctagcaa gtgcacgaga aaattatcca      2400
acatacattt atcaaaaagt agatgcatcg gagttaaaac cttatacacg atatagacta      2460
gatgggttcg tgaagagtag tcaagattta gaaattgatc tcattcacca tcataaagtc      2520
catcttgtga aaaatgtacc agataattta gtatctgata cttacccaga tgattcttgt      2580
agtggaatca atcgatgtca ggaacaacag atggtaaatg cgcaactgga aacagagcat      2640
catcatccga tggattgctg tgaagcagct caaacacatg agttttcttc ctatattgat      2700 acagggatt taaattcgag tgtagaccag ggaatctggg cgatctttaa agttcgaaca      2760
accgatggtt atgcgacgtt aggaaatctt gaattggtag aggtcggacc gttatcgggt      2820
gaatctttag aacgtgaaca aagggataat acaaaatgga gtgcagagct aggaagaaag      2880
cgtgcagaaa cagatcgcgt gtatcaagat gccaaacaat ccatcaatca tttatttgtg      2940
gattatcaag atcaacaatt aaatccagaa atagggatgg cagatattat ggacgctcaa      3000
aatcttgtcg catcaatttc agatgtatat agcgatgccg tactgcaaat ccctggaatt      3060
aactatgaga tttacacaga gctgtccaat cgcttacaac aagcatcgta tctgtatacg      3120
tctcgaaatg cggtgcaaaa tgggactttt aacaacgggc tagatagctg gaatgcaaca      3180
gcgggtgcat cggtacaaca ggatggcaat acgcatttct tagttctttc tcattgggat      3240
gcacaagttt ctcaacaatt tagagtgcag ccgaattgta aatatgtatt acgtgtaaca      3300
gcagagaaag taggcggcgg agacggatac gtgactatcc gggatggtgc tcatcataca      3360
gaaacgctta catttaatgc atgtgattat gatataaatg gcacgtacgt gactgataat      3420
acgtatctaa caaaagaagt gatattctat tcacatacag aacacatgtg ggtagaggta      3480
aatgaaacag aaggtgcatt tcatatagat agtattgaat tcgttgaaac agaaaagtaa      3540
```

<210> SEQ ID NO 5
<211> LENGTH: 3444
<212> TYPE: DNA
<213> ORGANISM: Artificial Sequence
<220> FEATURE:
<223> OTHER INFORMATION: Synthetic Cry Gene

<400> SEQUENCE: 5

```
atggacctgg atgggaataa gacagagaca gagaccgaga ttgtgaatgg gagcgagagc       60
agcattgacc cgagcagcgt ttcgtacgct gggaacaata gctactccag cgccctgaac      120
ctcaattcgt gccagaatag gggcatcgct cagtgggtta acacgctggg cggggctatt      180 ggcaggccg tgagcatcgg cacatctatc atttcactcc tggccgcgcc gacactcact      240
gggtctattt cactggcctt caatctcatc aggaggatgg ggaccggctc caacggctcg      300
tctatttccg acctgagcat ctgcgatctc ctgagcatca ttaacctgcg ggtttcgcag      360
```

```
gctgtgctca acgacgggat cgctgatttc aatggctccg ttgctgtgta cgacctgtac      420
ctccacgccc tgcgcagctg aacaataacc cctaacgctg ctactgctga ggagctgagg      480
acccgcttca ggatcgccga ttcggagttc gagaggattc tgacgagggg ctcgctcaca      540
catggcggct ccctcgcccg ccaggacgct caggtcctcc tgctcccgtc cttcgttaac      600
gcggcttacc tgcacctgct catcctccgc gatgcttcgc gctacggggc tcttggggc       660 ctcttcaaca ccacgccgca tatcaattac cccgtgaggc tgcagcagct cattggcagc      720
tacacgcact actgcacaca ttggtacaac caggggctga atgagatccg gcagcgcggc      780
aacactgccg tgaattggct cgagttccac cgctaccgcc gcgacatgac gctgatggtc      840
ctcgatgtgg tctcgctgtt ctctgccctc gacacgatcc gctacccgaa cgctacagtt      900
gtgcagctca gccgcactgt ctacaccgat ccgattggct tcgttaaccg cgggtcaggc      960
aataggctgt cctggttcga ctggaggaac caggcgaatt tctctactct cgagtcagag     1020
atgccgaccc cctcatcccc actgagcctc aaccacatgt cgatcttcac tgggcctctg     1080
accctcccag tgtcccctaa cacgcatagg gcccgggtct ggtacggcaa ccagaatatg     1140
ttcacaactg ggtcacagaa ctccggccag accacgaact ctattcagaa tatctcaggc     1200
ctggagattt tccgcatcga ctctcaggcg tgcaatctca ataacaattc atacggcgtg     1260
aacagggcgg agttcttcca cggggctagc cagggctcgc agcggtctgt ctaccaggga     1320
tacatccgcc agagcggcct ggacaaccct gtcgttatga atctgcagtc tttcctccca     1380
ggcgagaact cagccacccc tacgcgcag gattacaccc acattctgtc caacccggtt     1440
aatatcaggg gcgggctcag gcagattgtg gccgacaggc gctcctccgt ggtcgtttac     1500
ggctggacgc acaagtccct gagcaggagg tcactcgtgg ctccagacca gatcacccag     1560
gtcccagccg ttaaggcgtc cccttcttca cattgcacta tcattgccgg cccaggcttc     1620
accggcgggg acctggtgtc gctccagccc aacggccagc tcgtcatccc gttccaggtt     1680
tctgcgcccg agacgaacta ccacattcgc atctgctacg tctcgacgtc tgattgcagc     1740
attaacacaa tctgcaatga cgagacgcat ctgtccacac tcccgagcac aacttccagc     1800
ctggagaacc tccagtgcaa tcacctgcat tacttcaacg tgggcacttt caagccaacc     1860
atcgactcga agctgacgct cgtcaacaca tctcctaacg ctaacatcat tatcgacaag     1920
atcgagttca tccccggtgga taccgcccag cagcagaacg aggacctcga ggccgcgaag     1980
aaggctgtcg cctccctgtt cacacgcact agggacggcc tccaggtcaa tgttaaggac     2040
taccaggtgg atcaggctgc caacctggtc tcatgcctct ccgacgagca gtacggctac     2100
gataagaaga tgctgctcga ggccgtgagg gctgctaaga ggctgagcag ggagaggaac     2160
ctgctccagg accccgattt caacacaatc aactcgaccg aggagaacgg gtggaaggcg     2220
tcaaatggcg tcaccatctc cgagggcggg ccattctaca agggcagggc tattcagctc     2280
gcgtctgctc gggagaacta ccccacatac atctaccaga aggtggatgc ctccgagctg     2340
aagccataca cccgctaccg cctcgacggc ttcgtcaagt cgtctcagga cctggagatt     2400
gatctcatcc accatcacaa ggtgcacctg gtcaagaacg ttccggacaa tctcgtgagc     2460
gatacgtacc ccgacgattc atgctccgga atcaacaggt gccaggagca gcagatggtc     2520
aacgcgcagc tggagaccga gcatcaccat ccgatggact gctgcgaggc tgctcagacg     2580
cacgagttct catcctacat cgacacaggg gatctgaaca gctcggtcga tcagggcatt     2640
tgggccatct tcaaggttag gaccacggac gggtacgcta ccctcggcaa cctggagctg     2700
```

-continued

| | |
|---|---|
| gtggaggtcg ggccactgag cggcgagtcg ctcgagaggg agcagaggga caacactaag | 2760 |
| tggtccgctg agctgggccg caagagggct gagaccgacc gcgtctacca ggatgccaag | 2820 |
| cagagcatca atcacctgtt cgttgactac caggatcagc agctcaaccc cgagattggc | 2880 |
| atggcggaca tcatggatgc tcagaacctg gtggccagca tctcggacgt gtacagcgat | 2940 |
| gcggtcctcc agattccagg aatcaactac gagatctaca cggagctgtc gaacaggctc | 3000 |
| cagcaggcct cctacctgta cacaagccgg aacgcggtcc agaatgggga cttcaacaat | 3060 |
| ggcctcgatt catggaatgc tacggctggg gcttccgtgc agcaggatgg caacacacac | 3120 |
| ttcctggtcc tctcccattg ggacgcgcag gttagccagc agttccgcgt gcagccgaac | 3180 |
| tgcaagtatg tgctgagggt cactgctgag aaggttggcg ggggcgacgg ctacgtgacc | 3240 |
| atcagggacg atgcgcacca taccgagacg ctgacattca acgcttgcga ctacgacatc | 3300 |
| aacggcacct acgtgacaga caacacttac ctaaccaagg aggtggtctt ccacccggag | 3360 |
| actcagcata tgtgggttga ggtgaacgag accgagggcg ccttccacat agactccatc | 3420 |
| gagttcgtcg agaccgagaa gtga | 3444 |

<210> SEQ ID NO 6
<211> LENGTH: 3474
<212> TYPE: DNA
<213> ORGANISM: Artificial Sequence
<220> FEATURE:
<223> OTHER INFORMATION: Synthetic Cry Gene

<400> SEQUENCE: 6

| | |
|---|---|
| atgaacagga caaccagaa cgagtacgag attattgacg ccccccattg cggctgcccc | 60 |
| tccgacgacg atgtgaagta cccactggct agcgacccca cgctgctctg cagaacatg | 120 |
| aattacaagg attacctcca gatgaccgac gaggattaca cggactcgta catcaaccca | 180 |
| tccctcagca tttcgggcag ggacgctgtc cagacagccc tgactgtggt cggccgcatc | 240 |
| ctcggggcgc tgggcgttcc cttctcaggc cagattgtgt ccttctacca gttcctcctg | 300 |
| aatacctct ggccagtgaa cgacacggcg atctgggagg ctttcatgcg ccaggtggag | 360 |
| gagctggtca atcagcagat tacggagttc gccaggaacc aggctctcgc gcggctgcag | 420 |
| ggcctcgggg actccttcaa tgtctaccag aggagcctgc agaactggct cgccgaccgc | 480 |
| aacgatacca ggaatctctc cgttgtgcgc gcccagttca tcgcgctcga cctggatttc | 540 |
| gtgaatgcca ttcctctgtt cgctgtgaac ggccagcagg tcccgctcct gtccgtttac | 600 |
| gctcaggccg tgaacctgca tctcctgctc ctgaaggatg cttcgctctt cggcgagggg | 660 |
| tggggcttca cacagggcga gatctctact tactacgacc gccagctcga gctgacagcg | 720 |
| aggtacacta attactgcga gacctggtac aacacggggc tggacaggct caggggaacc | 780 |
| aacacggagt cctggctccg ctaccaccag ttccgcaggg agatgactct ggtcgttctc | 840 |
| gatgtggtcg ccctgttccc atactacgac gtccgcctct acccaaccgg ctccaaccct | 900 |
| cagctgacaa gggaggtgta cactgaccct atcgtcttca cccaccagc taatgtgggg | 960 |
| ctctgcaggc gctggggaac caacccgtac aatacgttca gcgagctgga gaacgcgttc | 1020 |
| atccggccac tcatctgtt cgatcgcctc aactctctca ccatttccag caataggttc | 1080 |
| cctgtctcgt ctaacttcat ggactactgg tctggccaca cgctgaggcg gagctacctc | 1140 |
| aacgattcgg ctgtgcagga ggactcctac ggcctcatca ccacgacacg ggccaccatt | 1200 |
| aacccggggg tcgatggcac caaccggatc gagtcgacgg cggtggactt ccgctctgct | 1260 |
| ctcatcggga tttacggcgt taacagggct tccttcgtgc caggcgggct gttcaatggc | 1320 |

```
actaccagcc cagctaacgg cgggtgcagg gacctgtacg ataccaacga cgagctgcca    1380
ccagacgagt ccacaggctc atccactcat cgcctctcgc acgtcacatt cttctctttc    1440
cagactaatc aggccgggtc aatcgcgaac gctggctccg ttcccaccta cgtgtggacg    1500
cgcagggacg tcgatctgaa caacacgatc actccgaacc gcattacgca gctcccactg    1560
gtgaaggctt ctgctccagt ctcaggcacg acagttctga aggggcccgg cttcaccggc    1620
gggggcatcc tccggcgcac taccaatggg accttcggca cgctgagggt gaccgtcaac    1680
agcccactga cgcagcagta caggctccgc gtgaggttcg cttctacggg caatttctca    1740
atcaggctcc tgagggggg cgtgagcatt ggggacgtca ggctgggctc gacaatgaac    1800
cggggccagg agctgacata cgagagcttc ttcactcgcg agttcacgac aactggccca    1860
ttcaatccac ctttcacctt cacgcaggcc caggagatcc tcacagttaa cgctgagggc    1920
gtgtcgactg ggggcgagta ctacattgat aggatcgaga ttgttccagt gaacccagct    1980
agggaggctg aggaggacct ggaggctgcc aagaaggctg tggccagcct gttcacacgc    2040
actagggacg gcctccaggt caatgttacc gattaccagg tcgacagggc ggctaacctg    2100
gtttcatgcc tctccgatga gcagtactcc cacgacaaga agatgctcct ggaggccgtc    2160
cgggctgcta agcgcctgtc acgggagcgc aacctcctgc aggaccctga tttcaacacg    2220
atcaactcca ctgaggagaa tgggtggaag gccagcaacg gcgtgaccat ttcggagggg    2280
ggcccgttct tcaagggccg cgcgctccag ctggctagcg ctagggagaa ctaccctacg    2340
tacatctacc agaaggtcga tgcgtcggtt ctgaagccgt acacacgcta ccgcctcgac    2400
ggcttcgtga agtcctccca ggatctggag atcgacctca ttcaccatca aaggtccat    2460 ctggttaaga acgtgcccga caatctcgtc tccgatacct acagcgacgg gtcctgcagc    2520
ggaatcaacc gctgcgatga gcagcagcag gtggatatgc agctcgacgc cgagcatcac    2580
ccaatggact gctgcgaggc tgcccagacc cacgagttct cttcctacat caatacgggg    2640
gatctgaacg cctccgttga ccagggcatt tggggttgtgc tcaaagtgag gaccacggac    2700
gggtacgcta ccctgggcaa cctcgagctg gtggaggtcg ggccgctgag cggcgagtcg    2760
ctcgagaggg agcagaggga taacgctaag tggaatgctg agctgggcag gaagagggct    2820
gagaccgaca gggtctacct ggctgctaag caggcgatca atcacctctt cgtggattac    2880
caggaccagc agctgaaccc tgagatcggc ctcgctgaga ttaacgaggc ctctaatctg    2940
gtcaagtcga tctctggggt ttactcagat actctcctgc agatcccggg aattaactac    3000
gagatttaca ccgagctgtc cgaccggctc cagcaggctt cctacctcta cacgagccgc    3060
aacgccgtgc agaatgggga tttcaactcg ggcctggact cttggaacgc gacaactgat    3120
gcttctgtcc agcaggacgg ctcaacccat ttcctcgtgc tgtcacactg gacgctcag    3180 gtgtcccagc agatgagggt caacctgaat tgcaagtacg tcctcagggt tacggcgaag    3240
aaggtcgggg gcgggatgg ctacgtcaca atcagggacg gcgcgcatca ccaggagacc    3300
ctcacgttca atgcttgcga ctacgatgtc aacggcacat acgttaacga caattcctac    3360
atcactaagg aggtcgttttt ctaccccgag accaagcaca tgtgggttga ggtgtctgag    3420
tcggagggct cgttctacat tgatagcatt gagttcattg agacgcagga gtga         3474
```

<210> SEQ ID NO 7  
<211> LENGTH: 3522  
<212> TYPE: DNA  
<213> ORGANISM: Artificial Sequence  
<220> FEATURE:

-continued

<223> OTHER INFORMATION: Synthetic Cry Gene

<400> SEQUENCE: 7

```
atgaaccgga acaaccaggg cgagtacgag attattgatg cctccacttg cggctgctcc     60
tcagatgatg tcgtccagta cccactcgct cgcgacccga acgctgcttt ccagaacatg    120
aattacaagg actacctgaa gatgtctgac ggcgattacg tcgattcata cattaaccca    180
ggcctgtcca tcgggaggag ggacgtcacg ctcacaggcg tcgggatcgt tgctctcatt    240
gtgggcaccc tgggcggccc agttggcggg attgtgacgg gcctgatctc cagcctcctg    300
gggctcctgt ggccaagcaa cgacaatgat gtgtgggagg ccttcatggc gcagatcgag    360
gagctgattg agcagaggat cgctgaccag gtggtccgga acgccctgga caatctcacc    420
ggcctgaggg attactacaa ccagtacctc ctggctctcg aggagtggca ggagaggccc    480
aatgccgtga ggtctacgct ggtcttcaac cggttcgaga cgctccattc acacttcgtg    540
acatcaatgc catccttcgg cagcgggcct ggcagcgagc gctacgcggt tcagctcctg    600
accgtgtacg ctcaggctgc caacctgcac ctcctgctcc tgagggacgc tgatatctac    660
ggcgctcggt gggggctcag ggagtcccag atcgacctct acttcaacga gctgcagaat    720
cggacgcgcg attacacaaa ccattgcgtc acagcctaca acaatggcct ggaggagatc    780
agggggactt cgccagcttc ttggctgcgc taccaccagt tccggcgcga gaccacgctc    840
attgccctcg acctggtggc gatcttccca tactacaatg tcagggagta cccaattggc    900
gttaaccctc agctcacgcg ggacgtgtac acagatccga tcggcgtcac gttcaggcgg    960
gaggactggg agacaggcgt cgagtgcagg ccgtgggtta ataccccata catgtctttc   1020
tcagatctgg agaacgccat cattaggccg ccccatctct tcgagacgct ccggaatctg   1080
acgattcaca caggcaggta caacctggtc ggcggggcga ggttcatcga gggctgggtc   1140
gggcattccg ttactaatac caggctgggc aacagcactg tgttcaccag caattacggg   1200
tcgctcccac ctcggttcca ggtgttcaac ttcacgaatt tcgacgtcta ccagatcaac   1260
acacgggccg attcgacggg cacattccgc attccggggt tcgcggtcac tagggctcag   1320
ttcatccccg gcgggaccta ctccgtggct caccgcgacc caggcgcttg ccagcaggac   1380
tacgattcaa ttgaggagct gccctccctg gacccagatg agcctatcaa ccggtcctac   1440
agccatcgcc tctcacacgt caccctgtac aagtacactc tctccgacac cgattacggc   1500
gtgatcaatt acaccgacta cgggagcatg ccagcttacg tgtggacgca tcgcgacgtc   1560
gatctgacta acaccattac ggcggatagg atcacgcagc tcccgctggt gaaggcttcg   1620
acactccccg ccggcacaac tgttgtgaag gggcccggct tcaccggcgg ggacatcctg   1680
aggaggacca cgaatggcac gttcgggaca ctccacgtga gggtcaacag cccactgacc   1740
cagcagtaca ggctccgggt ccgcttcgct tcgacgggca acttctctat tagggtgctg   1800
aggggcggga catctatcgg cgacgctcgc ttcgggtcaa ctatgaacag gggccaggag   1860
ctgacttacg agtccttcgt gacccgcgag ttcacaacta ccggcccgtt caatccgccc   1920
ttcacattca ctcagaccca ggagatcctg actgtcaacg ctgagggcgt ttcgaccggc   1980
ggggagtact acatcgactc tattgagatc gttccagtga acccaaccag ggaggctgag   2040
gaggatctcg aggctgctaa gaaggccgtc gcgagcctgt tcacgaggac acgggacggc   2100
ctccaggtca atgttacgga ctaccaggtt gatagggctg ctaacctcgt gctgtgcctc   2160
tccgacgagc agtacgccca cgataagaag atgctcctgg aggcggtgag ggctgctaag   2220
aggctgagca gggagaggaa cctcctgcag gaccctgatt tcaacgagat caattctact   2280
```

```
gaggactcag gctggaagac cagcaacggg atcattatct cggagggcgg gccgttcttc    2340
aagggccggg ccctgcagct cgcttccgct cgcgagaact accctaccta catctaccag    2400
aaggtggact cgtctatgct gaagccgtac acgaggtaca agctcgacgg cttcgtgcag    2460
tcatcccagg atctcgagat tgagctgatc caccatcaca aggtgcacct cgtcaagaac    2520
gttccagaca atctggtcct cgacacctac cctgatggct cgtgcaacgg aatcaaccgc    2580
tgcgaggagc agcagatggt gaactctcag ctggagacgg agcataccc tatggactgc     2640 tgcgaggcct cacagactca tgagttcagc tcgtacatcc acaccggcga cctcaacgcg    2700
tctgtcgatc aggggatttg gtcgttctg aagatcagga cgacagacgg ctcggctacc     2760
ctcgggaacc tggagctggt ggaggtcggc ccctgtcag gggagtccct cgagagggag     2820
cagagggaca acgccaagtg gaatgctgag ctgggccgga agcgcgctga ggctgatcgc    2880
gtgtaccagg cgctaagca ggccatcaat cacctcttcg tcgactacca ggatcagcag     2940
ctgaaccctg aggttggcct cgcggagatc agcgaggctc ggaacctgat tgagtcgatc    3000
tctgacgtgt actgcgatgc cgtcctccgc attccgggaa tcaactacga gatgtacacg    3060
gagctgtcca caggctgca gcaggctgct tacctgtaca aagccgcaa cgcggtgcag       3120 aatggcgact tcaactccgg gctcgatagc tggaatgcta ctaccgacgc caccgttcag    3180
caggatggca acatgtactt cctggtgctc agccactggg acgcccaggt ttcgcagcag    3240
ttccgcgtgc agccaaattg caagtatgtg ctgagggtca cagcgaagaa ggtcgggaac    3300
ggcgacggct acgtgactat ccaggatggc gcgcatcacc gcgagactct gaccttcaat    3360
gcttgcgact acgatgttaa cggcacgcat gtgaacgaca attcctacat tacaaaggag    3420
ctggagttct acccgaagac tgagcacatg tgggttgagg tgagcgagac tgagggcacc    3480
ttctacatag attcgatcga gctgattgag acccaggagt ga                        3522
```

<210> SEQ ID NO 8
<211> LENGTH: 3540
<212> TYPE: DNA
<213> ORGANISM: Artificial Sequence
<220> FEATURE:
<223> OTHER INFORMATION: Synthetic Cry Gene

<400> SEQUENCE: 8

```
atgggggga agtctatgaa caggaacaac cagggcgagt cgagagattat tgatgcctcc     60 acatgcgggt gctccagcga cgacgtggtc cagtacccac tcgctcgcga ccctaacgct    120
gctttccaga acatgaatta caaggactac ctgaagatgt ccgacggcga ttacgtggat    180
agctacatta acccaggcct ctcgatcggg aggagggacg tcactctgac cggggttggc    240
atcgtggcgc tgattgttgg cacactcggc gggcctgtgg gcgggattgt cactggcctc    300
atctccagcc tcctggggct cctgtggcca tccaacgaca atgatgtctg ggaggcgttc    360
atggctcaga tcgaggagct gattgagcag cgcatcgcgg accaggtggt caggaacgct    420
ctcgacaatc tgaccggcct cagggattac tacaaccagt acctcctggc tctcgaggag    480
tggcaggaga ggccaaatgc cgtgcgctcc acgctcgttt tcaaccgctt cgagaccctg    540
cacagccatt tcgtgacgag catgccgtcg ttcgggtctg ccccgggtc ggagcgctac      600 gctgtgcagc tcctgaccgt ctacgcccag gctgccaacc tccacctcct gctcctgcgc    660
gacgctgata tctacggcgc caggtggggg ctcaggagga ccagatcga cctgtacttc     720 aacgagctgc agaatcggac acgcgattac actaaccact gcgtcaccgc ctacaacaat    780
```

```
ggcctcgagg agatcagggg gacgtcacca gcttcctggc tccgctacca ccagttccgg      840
agggagacca cgctgattgc gctcgacctg gtggctatct tccctacta caatgtgcgc      900 gagtacccga ttggcgtcaa cccccagctg accagggacg tttacaccga cccgatcggc      960
gtgacattca ggcgggagga ctgggagact ggcgtggagt gcaggccgtg ggtcaatacc     1020
ccatacatgt ctttctcaga cctcgagaac gccatcatta ggccgcccca cctgttcgag     1080
acgctgagga atctcaccat tcatacgggc aggtacaacc tggtcggcgg ggcgcgcttc     1140
atcgagggct gggttgggca ctcagtgacg aacacaaggc tcggcaattc cacagtgttc     1200
acttccaact acggcagcct gccacctcgg ttccaggttt tcaacttcac aaatttcgac     1260
gtgtaccaga tcaacactag ggccgattcg actggcacct tccggattcc agggttcgcc     1320
gttacccgcg cgcagttcat ccctggcggg acgtactccg tggctcaccg cgacccgggc     1380
gcttgccagc aggactacga tagcattgag gagctgccct cgctcgaccc agatgagcct     1440
atcaacaggt cctacagcca ccggctgtct catgtcaccc tctacaagta caccctgtca     1500
gacacggatt acgcgtgat caattacacc gactacgggt ccatgccagc ttacgtttgg     1560
acgcaccggg acgtggatct cacgaacaca attactgccg accgcatcac acagctccca     1620
ctggtgaagg ccagcactct gcctgcgggc acaactgttg tgaagggccc tgggttcacc     1680
ggcggggaca tcctcaggag gaccacgaat ggcaccttcg ggacgctgca tgtccgcgtt     1740
aactccccgc tcacacagca gtacaggctg cgggtgcgct tcgcttcgac tggcaacttc     1800
tctattcgcg tcctcagggg cgggacctcc atcggcgacg ctaggttcgg gagcacgatg     1860 aacagggggcc aggagctgac atacgagtcc ttcgtcacta gggagttcac aactaccggc     1920
ccgttcaatc cgcccttcac cttcacgcag acacaggaga ttctcaccgt taacgctgag     1980
ggcgtgagca cggcgggga gtactacatc gactcgatcg agattgtgcc agtcaaccca     2040
accagggagg ctgaggagga tctggaggct gctaagaagg ccgtggcgag cctcttcact     2100
aggacccggg acgcctgca ggttaatgtg acggactacc aggtcgatca ggccgcgaac     2160
ctggttagct gcctctcgga cgagcagtac ggctacgata agaagatgct cctggaggcc     2220
gtccgcgctg ctaagaggct ctcgagggag aggaacctcc tgcaggaccc cgatttcaac     2280
acaattaatt ctactgagga gaacggctgg aaggcctcta tgggggtgac catctcagag     2340
ggcgggccat tctacaaggg cagggcgctc cagctggctt cagctcggga gaactacccc     2400
acctacatct accagaaggt cgacgcctcc gagctgaagc catacacgcg ctaccgcctg     2460
gatggcttcg tgaagtcgtc tcaggacctg gagatcgatc tcattcacca tcacaaggtc     2520
cacctcgtta agaacgtgcc ggacaatctg gtctccgata cctaccccga cgattcgtgc     2580
tctggaatca acaggtgcca ggagcagcag atggtgaacg cccagctcga cacggagcat     2640
caccatccta tggactgctg cgaggcggct cagacccatg agttctcatc ctacatcgac     2700
acgggcgatc tcaacagctc ggtcgaccag gggatctggg cgattttcaa ggttaggacg     2760
acagatggct acgctaccct ggggaatctc gagctggtcg aggttggccc cctctctggg     2820
gagtcactgg agagggagca gagggacaac acaaagtggt ctgctgagct gggcaggaag     2880
cgggctgaga ctgaccgcgt ctaccaggat gccaagcagt ccatcaatca cctcttcgtg     2940
gactaccagg atcagcagct gaaccctgag attggcatgg ctgacatcat ggatgcccag     3000
aacctcgtcg cgtcaatctc cgacgtctac agcgatgcgg ttctgcagat cccgggcatt     3060
aattacgaga tctacacaga gctgtcgaac aggctccagc aggcgtcata cctctacacg     3120
tcccggaacg ctgtgcagaa tggcgacttc aacaatgggc tggattcgtg gaatgcgaca     3180
```

```
gctggcgcct ctgtgcagca ggacgggaac actcacttcc tcgtcctgtc tcattgggat    3240
gcccaggtct cacagcagtt ccgggttcag ccgaactgca agtatgtgct gcgcgttacc    3300
gctgagaaag tgggcggggg cgacggctac gtcacgatcc gcgatggggc tcaccatacg    3360
gagacactca ctttcaacgc ctgcgactac gatatcaatg gcacatacgt tactgacaac    3420
acctacctga cgaaggaggt catcttctac tcccacacag agcatatgtg ggtggaggtc    3480
aacgagactg agggcgcctt ccacatcgac agcattgagt tcgtggagac cgagaagtga    3540

<210> SEQ ID NO 9
<211> LENGTH: 3444
<212> TYPE: DNA
<213> ORGANISM: Artificial Sequence
<220> FEATURE:
<223> OTHER INFORMATION: Synthetic Cry Gene

<400> SEQUENCE: 9
atggacctgg atgggaataa gacagagaca gagaccgaga ttgtgaatgg gagcgagagc      60
agcattgacc cgagcagcgt ttcgtacgct gggaacaata gctactccag cgccctgaac     120
ctcaattcgt gccagaatag gggcatcgct cagtgggtta acacgctggg cggggctatt     180
gggcaggccg tgagcatcgg cacatctatc atttcactcc tggccgcgcc gacactcact     240
gggtctattt cactggcctt caatctcatc aggaggatgg ggaccggctc caacggctcg     300
tctatttccg acctgagcat ctgcgatctc ctgagcatca ttaacctgcg ggtttcgcag     360
gctgtgctca cgacgggat cgctgatttc aatggctccg ttgctgtgta cgacctgtac     420
ctccacgccc tgcgcagctg gaacaataac cctaacgctg ctactgctga ggagctgagg     480
acccgcttca ggatcgccga ttcggagttc gagaggattc tgacgagggg ctcgctcaca     540
catggcggct ccctcgcccg ccaggacgct caggtcctcc tgctcccgtc cttcgttaac     600
gcggcttacc tgcacctgct catcctccgc gatgcttcgc gctacggggc ctcttggggc     660
ctcttcaaca ccacgccgca tatcaattac cccgtgaggc tgcagcagct cattggcagc     720
tacacgcact actgcacaca ttggtacaac caggggctga atgagatccg gcagcgcggc     780
aacactgccg tgaattggct cgagttccac cgctaccgcc gcgacatgac gctgatggtc     840
ctcgatgtgg tctcgctgtt ctctgccctc gacacgatcc gctacccgaa cgctacagtt     900
gtgcagctca gccgcactgt ctacaccgat ccgattggct cgttaaccg cgggtcaggc     960 aataggctgt cctggttcga ctggaggaac caggcgaatt ctctctactct cgagtcagag    1020 atgccgaccc cctcatcccc actgagcctc aaccacatgt cgatcttcac tgggcctctg    1080
accctcccag tgtcccctaa cacgcatagg gcccgggtct ggtacggcaa ccagaatatg    1140
ttcacaactg ggtcacagaa ctccggccag accacgaact ctattcagaa tatctcaggc    1200
ctggagattt tccgcatcga ctctcaggcg tgcaatctca taacaattc atacggcgtg    1260 aacagggcg agttcttcca cggggctagc agggctcgc agcggtctgt ctaccaggga    1320
tacatccgcc agagcggcct ggacaaccct gtcgttatga atctgcagtc tttcctccca    1380
ggcgagaact cagccacccc tacggcgcag gattacaccc acattctgtc caacccggtt    1440
aatatcaggg gcgggctcag gcagattgtg gccgacaggg ctcctccgt ggtcgtttac    1500 ggctggacgc acaagtccct gagcaggagg tcactcgtgg ctccagacca gatcacccag    1560
gtcccagccg ttaaggcgtc cccttcttca cattgcacta tcattgccgg cccaggcttc    1620
accggcgggg acctggtgtc gctccagccc aacggccagc tcgtcatccc gttccaggtt    1680
```

| | |
|---|---|
| tctgcgcccg agacgaacta ccacattcgc atctgctacg tctcgacgtc tgattgcagc | 1740 |
| attaacacaa tctgcaatga cgagacgcat ctgtccacac tcccgagcac aacttccagc | 1800 |
| ctggagaacc tccagtgcaa tcacctgcat tacttcaacg tgggcacttt caagccaacc | 1860 |
| atcgactcga agctgacgct cgtcaacaca tctcctaacg ctaacatcat tatcgacaag | 1920 |
| atcgagttca tcccggtgga taccgcccag cagcagaacg aggacctcga ggccgcgaag | 1980 |
| aaggctgtcg cctccctgtt cacacgcact agggacggcc tccaggtcaa tgttaaggac | 2040 |
| taccaggtgg atcaggctgc caacctggtc tcatgcctct ccgacgagca gtacggctac | 2100 |
| gataagaaga tgctgctcga ggccgtgagg gctgctaaga ggctgagcag ggagaggaac | 2160 |
| ctgctccagg accccgattt caacacaatc aactcgaccg aggagaacgg gtggaaggcg | 2220 |
| tcaaatggcg tcaccatctc cgagggcggg ccattctaca agggcagggc tattcagctc | 2280 |
| gcgtctgctc gggagaacta ccccacatac atctaccaga aggtggatgc ctccgagctg | 2340 |
| aagccataca cccgctaccg cctcgacggc ttcgtcaagt cgtctcagga cctggagatt | 2400 |
| gatctcatcc accatcacaa ggtgcacctg gtcaagaact tccggacaa tctcgtgagc | 2460 |
| gatacgtacc ccgacgattc atgctccgga atcaacaggt gccaggagca gcagatggtc | 2520 |
| aacgcgcagc tggagaccga gcatcaccat ccgatggact gctgcgaggc tgctcagacg | 2580 |
| cacgagttct catcctacat cgacacaggg gatctgaaca gctcggtcga tcagggcatt | 2640 |
| tgggccatct tcaaggttag gaccacggac gggtacgcta ccctcggcaa cctggagctg | 2700 |
| gtggaggtcg ggccactgag cggcgagtcg ctcgagaggg agcagaggga caacactaag | 2760 |
| tggtccgctg agctgggccg caagagggct gagaccgacc gcgtctacca ggatgccaag | 2820 |
| cagagcatca atcacctgtt cgttgactac caggatcagc agctcaaccc cgagattggc | 2880 |
| atggcggaca tcatggatgc tcagaacctg gtggccagca tctcggacgt gtacagcgat | 2940 |
| gcggtcctcc agattccagg aatcaactac gagatctaca cggagctgtc gaacaggctc | 3000 |
| cagcaggcct cctacctgta cacaagccgg aacgcggtcc agaatgggga cttcaacaat | 3060 |
| ggcctcgatt catggaatgc tacggctggg gcttccgtgc agcaggatgg caacacacac | 3120 |
| ttcctggtcc tctcccattg ggacgcgcag gttagccagc agttccgcgt gcagccgaac | 3180 |
| tgcaagtatg tgctgagggt cactgctgag aaggttggcg ggggcgacgg ctacgtgacc | 3240 |
| atcagggacg atgcgcacca taccgagacg ctgacattca acgcttgcga ctacgacatc | 3300 |
| aacggcacct acgtgacaga caacacttac atcaccaagg aggtggtctt ccacccggag | 3360 |
| actcagcata tgtgggttga ggtgaacgag accgagggcg ccttccacct tgactccatc | 3420 |
| gagttcgtcg agaccgagaa gtga | 3444 |

<210> SEQ ID NO 10
<211> LENGTH: 3474
<212> TYPE: DNA
<213> ORGANISM: Artificial Sequence
<220> FEATURE:
<223> OTHER INFORMATION: Synthetic Cry Gene

<400> SEQUENCE: 10

| | |
|---|---|
| atgaacagga caaccagaa cgagtacgag attattgacg cccccccattg cggctgcccc | 60 |
| tccgacgacg atgtgaagta cccactggct agcgaccccca acgctgctct gcagaacatg | 120 |
| aattacaagg attacctcca gatgaccgac gaggattaca cggactcgta catcaacccca | 180 |
| tccctcagca tttcgggcag ggacgctgtc cagacagccc tgactgtggt cggccgcatc | 240 |
| ctcggggcgc tgggcgttcc cttctcaggc cagattgtgt ccttctacca gttcctcctg | 300 |

```
aataccctct ggccagtgaa cgacacggcg atctgggagg ctttcatgcg ccaggtggag    360
gagctggtca atcagcagat tacggagttc gccaggaacc aggctctcgc gcggctgcag    420
ggcctcgggg actccttcaa tgtctaccag aggagcctgc agaactggct cgccgaccgc    480
aacgatacca ggaatctctc cgttgtgcgc gcccagttca tcgcgctcga cctggatttc    540
gtgaatgcca ttcctctgtt cgctgtgaac ggccagcagg tcccgctcct gtccgtttac    600
gctcaggccg tgaacctgca tctcctgctc ctgaaggatg cttcgctctt cggcgagggg    660
tggggcttca cacagggcga gatctctact cactacgacc gccagctcga gctgacagcg    720
aggtacacta attactgcga gacctggtac aacacgggc tggacaggct caggggaacc     780
aacacggagt cctggctccg ctaccaccag ttccgcaggg agatgactct ggtcgttctc    840
gatgtggtcg ccctgttccc atactacgac gtccgcctct acccaaccgg ctccaaccct    900
cagctgacaa gggaggtgta cactgaccct atcgtcttca acccaccagc taatgtgggg    960
ctctgcaggc gctggggaac caacccgtac aatacgttca gcgagctgga gaacgcgttc   1020
atccggccac ctcatctgtt cgatcgcatc cagtctctct caatttccag caataggttc   1080
cctgtctcgt ctaacttcat ggactactgg tctggccaca cgctgaggcg gagctacctc   1140
aacgattcgg ctgtgcagga ggactcctac ggcctcatca ccacgacacg gccaccatt    1200
aacccgggg tcgatggcac caaccggatc gagtcgacgg cggtggactt ccgctctgct    1260
ctcatcggga tttacggcgt taacagggct tccttcgtgc aggcgggct gttcaatggc     1320
actaccagcc cagctaacgg cgggtgcagg gacctgtacg ataccaacga cgagctgcca    1380
ccagacgagt ccacaggctc atccactcat cgcctctcgc acgtcacatt cttctctttc    1440
cagactaatc aggccgggtc aatcgcgaac gctggctccg ttcccaccta cgtgtggacg    1500
cgcagggacg tcgatctgaa caacacgatc actccgaacc gcattacgca gctcccactg    1560
gtgaaggctt ctgctccagt ctcaggcacg acagttctga aggggcccgg cttcaccggc    1620
gggggcatcc tccggcgcac taccaatggg accttcggca cgctgagggt gaccgtcaac    1680
agcccactga cgcagcagta caggctccgc gtgaggttcg cttctacggg caatttctca    1740
atcaggctcc tgagggggg cgtgagcatt ggggacgtca ggctgggctc gacaatgaac    1800
cggggccagg agctgacata cgagagcttc ttcactcgcg agttcacgac aactggccca    1860
ttcaatccac ctttcacctt cacgcaggcc caggagatcc tcacagttaa cgctgagggc    1920
gtgtcgactg ggggcgagta ctacattgat aggatcgaga ttgttccagt gaacccagct    1980
agggaggctg aggaggacct ggaggctgcc aagaaggctg tggccagcct gttcacacgc    2040
actagggacg gcctccaggt caatgttacc gattaccagg tcgacagggc ggctaacctg    2100
gtttcatgcc tctccgatga gcagtactcc cacgacaaga agatgctcct ggaggccgtc    2160
cgggctgcta agcgcctgtc acgggagcgc aacctcctgc aggaccctga tttcaacacg    2220
atcaactcca ctgaggagaa tgggtggaag gccagcaacg gcgtgaccat ttcggagggg    2280
ggcccgttct tcaagggccg cgcgctccag ctggctagcg ctagggagaa ctaccctacg    2340
tacatctacc agaaggtcga tgcgtcggtt ctgaagccgt acacacgcta ccgcctcgac    2400
ggcttcgtga agtcctccca ggatctggag atcgacctca ttcaccatca aaggtccat    2460
ctggttaaga acgtgcccga caatctcgtc tccgataccct acagcgacgg gtcctgcagc    2520
ggaatcaacc gctgcgatga gcagcagcag gtggatatgc agctcgacgc cgagcatcac    2580
ccaatggact gctgcgaggc tgcccagacc cacgagttct cttcctacat caatacgggg    2640
```

-continued

| | |
|---|---|
| gatctgaacg cctccgttga ccagggcatt tgggttgtgc tcaaagtgag gaccacggac | 2700 |
| gggtacgcta ccctgggcaa cctcgagctg gtggaggtcg ggccgctgag cggcgagtcg | 2760 |
| ctcgagaggg agcagaggga taacgctaag tggaatgctg agctgggcag gaagagggct | 2820 |
| gagaccgaca gggtctacct ggctgctaag caggcgatca atcacctctt cgtggattac | 2880 |
| caggaccagc agctgaaccc tgagatcggc ctcgctgaga ttaacgaggc ctctaatctg | 2940 |
| gtcaagtcga tctctggggt ttactcagat actctcctgc agatcccggg aattaactac | 3000 |
| gagatttaca ccgagctgtc cgaccggctc cagcaggctt cctacctcta cacgagccgc | 3060 |
| aacgccgtgc agaatgggga tttcaactcg ggcctggact cttggaacgc gacaactgat | 3120 |
| gcttctgtcc agcaggacgg ctcaacccat ttcctcgtgc tgtcacactg ggacgctcag | 3180 |
| gtgtcccagc agatgagggt caacctgaat tgcaagtacg tcctcagggt tacggcgaag | 3240 |
| aaggtcgggg gcgggatgg ctacgtcaca atcagggacg gcgcgcatca ccaggagacc | 3300 |
| ctcacgttca atgcttgcga ctacgatgtc aacggcacat acgttaacga caattcctac | 3360 |
| atcactaagg aggtcgtttt ctaccccgag accaagcaca tgtgggttga ggtgtctgag | 3420 |
| tcggagggct cgttctacat tgatagcatt gagttcattg agacgcagga gtga | 3474 |

<210> SEQ ID NO 11
<211> LENGTH: 3522
<212> TYPE: DNA
<213> ORGANISM: Artificial Sequence
<220> FEATURE:
<223> OTHER INFORMATION: Synthetic Cry Gene

<400> SEQUENCE: 11

| | |
|---|---|
| atgaaccgga caaccaggg cgagtacgag attattgatg cctccacttg cggctgctcc | 60 |
| tcagatgatg tcgtccagta cccactcgct cgcgacccga acgctgcttt ccagaacatg | 120 |
| aattacaagg actacctgaa gatgtctgac ggcgattacg tcgattcata cattaaccca | 180 |
| ggcctgtcca tcgggaggag ggacgtcacg ctcacaggcg tcgggatcgt tgctctcatt | 240 |
| gtgggcaccc tgggcggccc agttggcggg attgtgacgg gcctgatctc cagcctcctg | 300 |
| gggctcctgt ggccaagcaa cgacaatgat gtgtgggagg ccttcatggc gcagatcgag | 360 |
| gagctgattg agcagaggat cgctgaccag gtggtccgga acgccctgga caatctcacc | 420 |
| ggcctgaggg attactacaa ccagtacctc ctggctctcg aggagtggca ggagaggccc | 480 |
| aatgccgtga ggtctacgct ggtcttcaac cggttcgaga cgctccattc acacttcgtg | 540 |
| acatcaatgc catccttcgg cagcgggcct ggcagcgagc gctacgcggt tcagctcctg | 600 |
| accgtgtacg ctcaggctgc caacctgcac ctcctgctcc tgagggacgc tgatatctac | 660 |
| ggcgctcggt gggggctcag ggagtcccag atcgacctct acttcaacga gctgcagaat | 720 |
| cggacgcgcg attacacaaa ccattgcgtc acagcctaca caatggcct ggaggagatc | 780 |
| aggggggactt cgccagcttc ttggctgcgc taccaccagt tccggcgcga gaccacgctc | 840 |
| attgccctcg acctggtggc gatcttccca tactacaatg tcaggagta cccaattggc | 900 |
| gttaaccctc agctcacgcg ggacgtgtac acagatccga tcggcgtcac gttcaggcgg | 960 |
| gaggactggg agacaggcgt cgagtgcagg ccgtgggtta atacccccata catgtctttc | 1020 |
| tcagatctgg agaacgccat cattaggccg ccccatctct tcgagacgct ccggaatctg | 1080 |
| acgattcaca caggcaggta caacctggtc ggcggggcga ggttcatcga gggctgggtc | 1140 |
| gggcattccg ttactaatac caggctgggc aacagcactg tgttcaccag caattacggg | 1200 |
| tcgctcccac ctcggttcca ggtgttcaac ttcacgaatt tcgacgtcta ccagatcaac | 1260 |

```
acacgggccg attcgacggg cacattccgc attccggggt tcgcggtcac tagggctcag    1320
ttcatccccg gcgggaccta ctccgtggct caccgcgacc caggcgcttg ccagcaggac    1380
tacgattcaa ttgaggagct gccctccctg gacccagatg agcctatcaa ccggtcctac    1440
agccatcgcc tctcacacgt caccctgtac aagtacactc tctccgacac cgattacggc    1500
gtgatcaatt acaccgacta cgggagcatg ccagcttacg tgtggacgca tcgcgacgtc    1560
gatctgacta acaccattac ggcggatagg atcacgcagc tcccgctggt gaaggcttcg    1620
acactccccg ccggcacaac tgttgtgaag gggcccggct tcaccggcgg ggacatcctg    1680
aggaggacca cgaatggcac gttcgggaca ctccacgtga gggtcaacag cccactgacc    1740
cagcagtaca ggctccgggt ccgcttcgct tcgacgggca acttctctat tagggtgctg    1800
aggggcggga catctatcgg cgacgctcgc ttcgggtcaa ctatgaacag ggggccaggag   1860
ctgacttacg agtccttcgt gacccgcgag ttcacaacta ccggcccgtt caatccgccc   1920
ttcacattca ctcagaccca ggagatcctg actgtcaacg ctgagggcgt ttcgaccggc   1980
ggggagtact acatcgactc tattgagatc gttccagtga acccaaccag ggaggctgag   2040
gaggatctcg aggctgctaa gaaggccgtc gcgagcctgt tcacgaggac acgggacggc   2100
ctccaggtca atgttacgga ctaccaggtt gatagggctg ctaacctcgt gctgtgcctc   2160
tccgacgagc agtacgccca cgataagaag atgctcctgg aggcggtgag ggctgctaag   2220
aggctgagca gggagaggaa cctcctgcag gaccctgatt tcaacgagat caattctact   2280
gaggactcag gctggaagac cagcaacggg atcattatct cggagggcgg gccgttcttc   2340
aagggccggg ccctgcagct cgcttccgct cgcgagaact accctaccta catctaccag   2400
aaggtggact cgtctatgct gaagccgtac acgaggtaca agctcgacgg cttcgtgcag   2460
tcatcccagg atctcgagat tgagctgatc caccatcaca aggtgcacct cgtcaagaac   2520
gttccagaca atctggtcct cgacacctac cctgatggct cgtgcaacgg aatcaaccgc   2580
tgcgaggagc agcagatggt gaactctcag ctggagacgg agcatcaccc tatggactgc   2640
tgcgaggcct cacagactca tgagttcagc tcgtacatcc acaccggcga cctcaacgcg   2700
tctgtcgatc agggggattttg ggtcgttctg aagatcagga cgacagacgg ctcggctacc   2760
ctcgggaacc tggagctggt ggaggtcggc cccctgtcag gggagtccct cgagagggag   2820
cagagggaca acgccaagtg gaatgctgag ctgggccgga agcgcgctga ggctgatcgc   2880
gtgtaccagg gcgctaagca ggccatcaat cacctcttcg tcgactacca ggatcagcag   2940
ctgaaccctg aggttggcct cgcggagatc agcgaggctc ggaacctgat tgagtcgatc   3000
tctgacgtgt actgcgatgc cgtcctccgc attccgggaa tcaactacga gatgtacacg   3060
gagctgtcca acaggctgca gcaggctgct tacctgtaca aagccgcaa cgcggtgcag   3120
aatggcgact tcaactccgg gctcgatagc tggaatgcta ctaccgacgc caccgttcag   3180
caggatggca acatgtactt cctggtgctc agccactggg acgcccaggt ttcgcagcag   3240
ttccgcgtgc agccaaattg caagtatgtg ctgagggtca cagcgaagaa ggtcgggaac   3300
ggcgacggct acgtgactat ccaggatggc gcgcatcacc gcgagactct gaccttcaat   3360
gcttgcgact acgatgttaa cggcacgcat gtgaacgaca attcctacct cacaaaggag   3420
ctggagttct acccgaagac tgagcacatg tgggttgagg tgagcgagac tgagggcacc   3480
ttctaccttg attcgatcga gctgattgag acccaggagt ga                      3522
```

<210> SEQ ID NO 12

-continued

<211> LENGTH: 3540
<212> TYPE: DNA
<213> ORGANISM: Artificial Sequence
<220> FEATURE:
<223> OTHER INFORMATION: Synthetic Cry Gene

<400> SEQUENCE: 12

```
atgggggga agtctatgaa caggaacaac cagggcgagt acgagattat tgatgcctcc      60
acatgcgggt gctccagcga cgacgtggtc cagtacccac tcgctcgcga ccctaacgct    120
gctttccaga acatgaatta caaggactac ctgaagatgt ccgacggcga ttacgtggat    180
agctacatta acccaggcct ctcgatcggg aggagggacg tcactctgac cggggttggc    240
atcgtggcgc tgattgttgg cacactcggc gggcctgtgg gcgggattgt cactggcctc    300
atctccagcc tcctggggct cctgtggcca tccaacgaca atgatgtctg ggaggcgttc    360
atggctcaga tcgaggagct gattgagcag cgcatcgcgg accaggtggt caggaacgct    420
ctcgacaatc tgaccggcct cagggattac tacaaccagt acctcctggc tctcgaggag    480
tggcaggaga ggccaaatgc cgtgcgctcc acgctcgttt tcaaccgctt cgagaccctg    540
cacagccatt tcgtgacgag catgccgtcg ttcgggtctg gccccgggtc ggagcgctac    600
gctgtgcagc tcctgaccgt ctacgcccag gctgccaacc tccacctcct gctcctgcgc    660
gacgctgata tctacggcgc caggtggggg ctcagggaga gccagatcga cctgtacttc    720
aacgagctgc agaatcggac acgcgattac actaaccact gcgtcaccgc ctacaacaat    780
ggcctcgagg agatcagggg gacgtcacca gcttcctggc tccgctacca ccagttccgg    840
agggagacca cgctgattgc gctcgacctg gtggctatct tcccctacta caatgtgcgc    900
gagtacccga ttggcgtcaa cccccagctg accagggacg tttacaccga cccgatcggc    960
gtgacattca ggcgggagga ctgggagact ggcgtggagt gcaggccgtg ggtcaatacc   1020
ccatacatgt ctttctcaga cctcgagaac gccatcatta ggccgcccca cctgttcgag   1080
acgctgagga atctcaccat tcatacgggc aggtacaacc tggtcggcgg ggcgcgcttc   1140
atcgagggct gggttgggca ctcagtgacg aacacaaggc tcggcaattc cacagtgttc   1200
acttccaact acggcagcct gccacctcgg ttccaggttt tcaacttcac aaatttcgac   1260
gtgtaccaga tcaacactag ggccgattcg actggcacct tccggattcc agggttcgcc   1320
gttacccgcg cgcagttcat ccctggcggg acgtactccg tggctcaccg cgacccgggc   1380
gcttgccagc aggactacga tagcattgag gagctgccct cgctcgaccc agatgagcct   1440
atcaacaggt cctacagcca ccggctgtct catgtcaccc tctacaagta caccctgtca   1500
gacacggatt acggcgtgat caattacacc gactacgggt ccatgccagc ttacgtttgg   1560
acgcaccggg acgtggatct cacgaacaca attactgccg accgcatcac acagctccca   1620
ctggtgaagg ccagcactct gcctgcgggc acaactgttg tgaagggccc tgggttcacc   1680
ggcggggaca tcctcaggag gaccacgaat ggcaccttcg ggacgctgca tgtccgcgtt   1740
aactccccgc tcacacagca gtacaggctg cgggtgcgct tcgcttcgac tggcaacttc   1800
tctattcgcg tcctcagggg cgggacctcc atcggcgacg ctaggttcgg gagcacgatg   1860
aacaggggcc aggagctgac atacgagtcc ttcgtcacta gggagttcac aactaccggc   1920
ccgttcaatc cgcccttcac cttcacgcag acacaggaga ttctcaccgt taacgctgag   1980
ggcgtgagca cgggcgggga gtactacatc gactcgatcg agattgtgcc agtcaaccca   2040
accagggagg ctgaggagga tctggaggct gctaagaagg ccgtggcgag cctcttcact   2100
aggacccggg acggcctgca ggttaatgtg acggactacc aggtcgatca ggccgcgaac   2160
```

-continued

```
ctggttagct gcctctcgga cgagcagtac ggctacgata agaagatgct cctggaggcc    2220
gtccgcgctg ctaagaggct ctcgagggag aggaacctcc tgcaggaccc cgatttcaac    2280
acaattaatt ctactgagga gaacggctgg aaggcctcta atggggtgac catctcagag    2340
ggcgggccat tctacaaggg cagggcgctc cagctggctt cagctcggga gaactacccc    2400
acctacatct accagaaggt cgacgcctcc gagctgaagc catacacgcg ctaccgcctg    2460
gatggcttcg tgaagtcgtc tcaggacctg agatcgatc tcattcacca tcacaaggtc     2520
cacctcgtta agaacgtgcc ggacaatctg gtctccgata cctaccccga cgattcgtgc    2580
tctggaatca acaggtgcca ggagcagcag atggtgaacg cccagctcga cgcggagcat    2640
caccatccta tggactgctg cgaggcggct cagacccatg agttctcatc ctacatcgac    2700
acgggcgatc tcaacagctc ggtcgaccag gggatctggg cgattttcaa ggttaggacg    2760
acagatggct acgctaccct ggggaatctc gagctggtcg aggttggccc cctctctggg    2820
gagtcactgg agagggagca gagggacaac acaaagtggt ctgctgagct gggcaggaag    2880
cgggctgaga ctgaccgcgt ctaccaggat gccaagcagt ccatcaatca cctcttcgtg    2940
gactaccagg atcagcagct gaaccctgag attggcatgg ctgacatcat ggatgcccag    3000
aacctcgtcg cgtcaatctc cgacgtctac agcgatgcgg ttctgcagat cccgggcatt    3060
aattacgaga tctacacaga gctgtcgaac aggctccagc aggcgtcata cctctacacg    3120
tcccggaacg ctgtgcagaa tggcgacttc aacaatgggc tggattcgtg gaatgcgaca    3180
gctggcgcct ctgtgcagca ggacgggaac actcacttcc tcgtcctgtc tcattgggat    3240
gcccaggtct cacagcagtt ccgggttcag ccgaactgca agtatgtgct gcgcgttacc    3300
gctgagaaag tgggcggggg cgacggctac gtcacgatcc gcgatggggc tcaccatacg    3360
gagacactca ctttcaacgc ctgcgactac gatatcaatg gcacatacgt tactgacaac    3420
acctacctga cgaaggaggt catcttctac tcccacacag agcatatgtg ggtggaggtc    3480
aacgagactg agggcgcctt ccacctcgac agccttgagt tcgtggagac cgagaagtga    3540
```

<210> SEQ ID NO 13
<211> LENGTH: 1147
<212> TYPE: PRT
<213> ORGANISM: Bacillus thuringiensis

<400> SEQUENCE: 13

```
Met Asp Leu Asp Gly Asn Lys Thr Glu Thr Glu Thr Glu Ile Val Asn
1               5                   10                  15

Gly Ser Glu Ser Ser Ile Asp Pro Ser Ser Val Ser Tyr Ala Gly Asn
            20                  25                  30

Asn Ser Tyr Ser Ser Ala Leu Asn Leu Asn Ser Cys Gln Asn Arg Gly
        35                  40                  45

Ile Ala Gln Trp Val Asn Thr Leu Gly Gly Ala Ile Gly Gln Ala Val
    50                  55                  60

Ser Ile Gly Thr Ser Ile Ile Ser Leu Leu Ala Ala Pro Thr Leu Thr
65                  70                  75                  80

Gly Ser Ile Ser Leu Ala Phe Asn Leu Ile Arg Arg Met Gly Thr Gly
                85                  90                  95

Ser Asn Gly Ser Ser Ile Ser Asp Leu Ser Ile Cys Asp Leu Leu Ser
            100                 105                 110

Ile Ile Asn Leu Arg Val Ser Gln Ala Val Leu Asn Asp Gly Ile Ala
        115                 120                 125
```

```
Asp Phe Asn Gly Ser Val Ala Val Tyr Asp Leu Tyr Leu His Ala Leu
    130                 135                 140

Arg Ser Trp Asn Asn Pro Asn Ala Ala Thr Ala Glu Glu Leu Arg
145                 150                 155                 160

Thr Arg Phe Arg Ile Ala Asp Ser Glu Phe Glu Arg Ile Leu Thr Arg
                165                 170                 175

Gly Ser Leu Thr His Gly Gly Ser Leu Ala Arg Gln Asp Ala Gln Val
                180                 185                 190

Leu Leu Leu Pro Ser Phe Val Asn Ala Ala Tyr Leu His Leu Leu Ile
            195                 200                 205

Leu Arg Asp Ala Ser Arg Tyr Gly Ala Ser Trp Gly Leu Phe Asn Thr
    210                 215                 220

Thr Pro His Ile Asn Tyr Pro Val Arg Leu Gln Gln Leu Ile Gly Ser
225                 230                 235                 240

Tyr Thr His Tyr Cys Thr His Trp Tyr Asn Gln Gly Leu Asn Glu Ile
                245                 250                 255

Arg Gln Arg Gly Asn Thr Ala Val Asn Trp Leu Glu Phe His Arg Tyr
                260                 265                 270

Arg Arg Asp Met Thr Leu Met Val Leu Asp Val Val Ser Leu Phe Ser
            275                 280                 285

Ala Leu Asp Thr Ile Arg Tyr Pro Asn Ala Thr Val Gln Leu Ser
    290                 295                 300

Arg Thr Val Tyr Thr Asp Pro Ile Gly Phe Val Asn Arg Gly Ser Gly
305                 310                 315                 320

Asn Arg Leu Ser Trp Phe Asp Trp Arg Asn Gln Ala Asn Phe Ser Thr
                325                 330                 335

Leu Glu Ser Glu Met Pro Thr Pro Ser Ser Pro Leu Ser Leu Asn His
                340                 345                 350

Met Ser Ile Phe Thr Gly Pro Leu Thr Leu Pro Val Ser Pro Asn Thr
            355                 360                 365

His Arg Ala Arg Val Trp Tyr Gly Asn Gln Asn Met Phe Thr Thr Gly
    370                 375                 380

Ser Gln Asn Ser Gly Gln Thr Thr Asn Ser Ile Gln Asn Ile Ser Gly
385                 390                 395                 400

Leu Glu Ile Phe Arg Ile Asp Ser Gln Ala Cys Asn Leu Asn Asn Asn
                405                 410                 415

Ser Tyr Gly Val Asn Arg Ala Glu Phe Phe His Gly Ala Ser Gln Gly
                420                 425                 430

Ser Gln Arg Ser Val Tyr Gln Gly Tyr Ile Arg Gln Ser Gly Leu Asp
            435                 440                 445

Asn Pro Val Val Met Asn Leu Gln Ser Phe Leu Pro Gly Glu Asn Ser
    450                 455                 460

Ala Thr Pro Thr Ala Gln Asp Tyr Thr His Ile Leu Ser Asn Pro Val
465                 470                 475                 480

Asn Ile Arg Gly Gly Leu Arg Gln Ile Val Ala Asp Arg Arg Ser Ser
                485                 490                 495

Val Val Val Tyr Gly Trp Thr His Lys Ser Leu Ser Arg Arg Ser Leu
                500                 505                 510

Val Ala Pro Asp Gln Ile Thr Gln Val Pro Ala Val Lys Ala Ser Pro
            515                 520                 525

Ser Ser His Cys Thr Ile Ile Ala Gly Pro Gly Phe Thr Gly Gly Asp
    530                 535                 540

Leu Val Ser Leu Gln Pro Asn Gly Gln Leu Val Ile Pro Phe Gln Val
```

-continued

```
        545                 550                 555                 560

Ser Ala Pro Glu Thr Asn Tyr His Ile Arg Ile Cys Tyr Val Ser Thr
                565                 570                 575

Ser Asp Cys Ser Ile Asn Thr Ile Cys Asn Asp Glu Thr His Leu Ser
                580                 585                 590

Thr Leu Pro Ser Thr Thr Ser Ser Leu Glu Asn Leu Gln Cys Asn His
                595                 600                 605

Leu His Tyr Phe Asn Val Gly Thr Phe Lys Pro Thr Ile Asp Ser Lys
                610                 615                 620

Leu Thr Leu Val Asn Thr Ser Pro Asn Ala Asn Ile Ile Asp Lys
625                 630                 635                 640

Ile Glu Phe Ile Pro Val Asp Thr Ala Gln Gln Gln Asn Glu Asp Leu
                645                 650                 655

Glu Ala Ala Lys Lys Ala Val Ala Ser Leu Phe Thr Arg Thr Arg Asp
                660                 665                 670

Gly Leu Gln Val Asn Val Lys Asp Tyr Gln Val Asp Gln Ala Ala Asn
                675                 680                 685

Leu Val Ser Cys Leu Ser Asp Glu Gln Tyr Gly Tyr Asp Lys Lys Met
                690                 695                 700

Leu Leu Glu Ala Val Arg Ala Ala Lys Arg Leu Ser Arg Glu Arg Asn
705                 710                 715                 720

Leu Leu Gln Asp Pro Asp Phe Asn Thr Ile Asn Ser Thr Glu Glu Asn
                725                 730                 735

Gly Trp Lys Ala Ser Asn Gly Val Thr Ile Ser Glu Gly Pro Phe
                740                 745                 750

Tyr Lys Gly Arg Ala Ile Gln Leu Ala Ser Ala Arg Glu Asn Tyr Pro
                755                 760                 765

Thr Tyr Ile Tyr Gln Lys Val Asp Ala Ser Glu Leu Lys Pro Tyr Thr
                770                 775                 780

Arg Tyr Arg Leu Asp Gly Phe Val Lys Ser Ser Gln Asp Leu Glu Ile
785                 790                 795                 800

Asp Leu Ile His His His Lys Val His Leu Val Lys Asn Val Pro Asp
                805                 810                 815

Asn Leu Val Ser Asp Thr Tyr Pro Asp Asp Ser Cys Ser Gly Ile Asn
                820                 825                 830

Arg Cys Gln Glu Gln Gln Met Val Asn Ala Gln Leu Glu Thr Glu His
                835                 840                 845

His His Pro Met Asp Cys Cys Glu Ala Ala Gln Thr His Glu Phe Ser
                850                 855                 860

Ser Tyr Ile Asp Thr Gly Asp Leu Asn Ser Ser Val Asp Gln Gly Ile
865                 870                 875                 880

Trp Ala Ile Phe Lys Val Arg Thr Thr Asp Gly Tyr Ala Thr Leu Gly
                885                 890                 895

Asn Leu Glu Leu Val Glu Val Gly Pro Leu Ser Gly Glu Ser Leu Glu
                900                 905                 910

Arg Glu Gln Arg Asp Asn Thr Lys Trp Ser Ala Glu Leu Gly Arg Lys
                915                 920                 925

Arg Ala Glu Thr Asp Arg Val Tyr Gln Asp Ala Lys Gln Ser Ile Asn
                930                 935                 940

His Leu Phe Val Asp Tyr Gln Asp Gln Gln Leu Asn Pro Glu Ile Gly
945                 950                 955                 960

Met Ala Asp Ile Met Asp Ala Gln Asn Leu Val Ala Ser Ile Ser Asp
                965                 970                 975
```

-continued

```
Val Tyr Ser Asp Ala Val Leu Gln Ile Pro Gly Ile Asn Tyr Glu Ile
                980                 985                 990

Tyr Thr Glu Leu Ser Asn Arg Leu Gln Gln Ala Ser Tyr Leu Tyr Thr
            995                1000                1005

Ser Arg Asn Ala Val Gln Asn Gly Asp Phe Asn Asn Gly Leu Asp
    1010                1015                1020

Ser Trp Asn Ala Thr Ala Gly Ala Ser Val Gln Gln Asp Gly Asn
    1025                1030                1035

Thr His Phe Leu Val Leu Ser His Trp Asp Ala Gln Val Ser Gln
    1040                1045                1050

Gln Phe Arg Val Gln Pro Asn Cys Lys Tyr Val Leu Arg Val Thr
    1055                1060                1065

Ala Glu Lys Val Gly Gly Gly Asp Gly Tyr Val Thr Ile Arg Asp
    1070                1075                1080

Asp Ala His His Thr Glu Thr Leu Thr Phe Asn Ala Cys Asp Tyr
    1085                1090                1095

Asp Ile Asn Gly Thr Tyr Val Thr Asp Asn Thr Tyr Leu Thr Lys
    1100                1105                1110

Glu Val Val Phe His Pro Glu Thr Gln His Met Trp Val Glu Val
    1115                1120                1125

Asn Glu Thr Glu Gly Ala Phe His Ile Asp Ser Ile Glu Phe Val
    1130                1135                1140

Glu Thr Glu Lys
    1145

<210> SEQ ID NO 14
<211> LENGTH: 1157
<212> TYPE: PRT
<213> ORGANISM: Bacillus thuringiensis

<400> SEQUENCE: 14

Met Asn Arg Asn Asn Gln Asn Glu Tyr Glu Ile Ile Asp Ala Pro His
1               5                   10                  15

Cys Gly Cys Pro Ser Asp Asp Val Lys Tyr Pro Leu Ala Ser Asp
            20                  25                  30

Pro Asn Ala Ala Leu Gln Asn Met Asn Tyr Lys Asp Tyr Leu Gln Met
        35                  40                  45

Thr Asp Glu Asp Tyr Thr Asp Ser Tyr Ile Asn Pro Ser Leu Ser Ile
    50                  55                  60

Ser Gly Arg Asp Ala Val Gln Thr Ala Leu Thr Val Val Gly Arg Ile
65                  70                  75                  80

Leu Gly Ala Leu Gly Val Pro Phe Ser Gly Gln Ile Val Ser Phe Tyr
                85                  90                  95

Gln Phe Leu Leu Asn Thr Leu Trp Pro Val Asn Asp Thr Ala Ile Trp
            100                 105                 110

Glu Ala Phe Met Arg Gln Val Glu Glu Leu Val Asn Gln Gln Ile Thr
        115                 120                 125

Glu Phe Ala Arg Asn Gln Ala Leu Ala Arg Leu Gln Gly Leu Gly Asp
    130                 135                 140

Ser Phe Asn Val Tyr Gln Arg Ser Leu Gln Asn Trp Leu Ala Asp Arg
145                 150                 155                 160

Asn Asp Thr Arg Asn Leu Ser Val Val Arg Ala Gln Phe Ile Ala Leu
                165                 170                 175

Asp Leu Asp Phe Val Asn Ala Ile Pro Leu Phe Ala Val Asn Gly Gln
```

```
                180             185             190
    Gln Val Pro Leu Leu Ser Val Tyr Ala Gln Ala Val Asn Leu His Leu
                195             200             205
    Leu Leu Leu Lys Asp Ala Ser Leu Phe Gly Glu Gly Trp Gly Phe Thr
                210             215             220
    Gln Gly Glu Ile Ser Thr Tyr Tyr Asp Arg Gln Leu Glu Leu Thr Ala
    225             230             235             240
    Arg Tyr Thr Asn Tyr Cys Glu Thr Trp Tyr Asn Thr Gly Leu Asp Arg
                    245             250             255
    Leu Arg Gly Thr Asn Thr Glu Ser Trp Leu Arg Tyr His Gln Phe Arg
                260             265             270
    Arg Glu Met Thr Leu Val Val Leu Asp Val Val Ala Leu Phe Pro Tyr
                275             280             285
    Tyr Asp Val Arg Leu Tyr Pro Thr Gly Ser Asn Pro Gln Leu Thr Arg
            290             295             300
    Glu Val Tyr Thr Asp Pro Ile Val Phe Asn Pro Pro Ala Asn Val Gly
    305             310             315             320
    Leu Cys Arg Arg Trp Gly Thr Asn Pro Tyr Asn Thr Phe Ser Glu Leu
                    325             330             335
    Glu Asn Ala Phe Ile Arg Pro Pro His Leu Phe Asp Arg Leu Asn Ser
                340             345             350
    Leu Thr Ile Ser Ser Asn Arg Phe Pro Val Ser Ser Asn Phe Met Asp
                355             360             365
    Tyr Trp Ser Gly His Thr Leu Arg Arg Ser Tyr Leu Asn Asp Ser Ala
            370             375             380
    Val Gln Glu Asp Ser Tyr Gly Leu Ile Thr Thr Thr Arg Ala Thr Ile
    385             390             395             400
    Asn Pro Gly Val Asp Gly Thr Asn Arg Ile Glu Ser Thr Ala Val Asp
                    405             410             415
    Phe Arg Ser Ala Leu Ile Gly Ile Tyr Gly Val Asn Arg Ala Ser Phe
                420             425             430
    Val Pro Gly Gly Leu Phe Asn Gly Thr Thr Ser Pro Ala Asn Gly Gly
                435             440             445
    Cys Arg Asp Leu Tyr Asp Thr Asn Asp Glu Leu Pro Pro Asp Glu Ser
            450             455             460
    Thr Gly Ser Ser Thr His Arg Leu Ser His Val Thr Phe Phe Ser Phe
    465             470             475             480
    Gln Thr Asn Gln Ala Gly Ser Ile Ala Asn Ala Gly Ser Val Pro Thr
                    485             490             495
    Tyr Val Trp Thr Arg Arg Asp Val Asp Leu Asn Asn Thr Ile Thr Pro
                500             505             510
    Asn Arg Ile Thr Gln Leu Pro Leu Val Lys Ala Ser Ala Pro Val Ser
                515             520             525
    Gly Thr Thr Val Leu Lys Gly Pro Gly Phe Thr Gly Gly Gly Ile Leu
            530             535             540
    Arg Arg Thr Thr Asn Gly Thr Phe Gly Thr Leu Arg Val Thr Val Asn
    545             550             555             560
    Ser Pro Leu Thr Gln Gln Tyr Arg Leu Arg Val Arg Phe Ala Ser Thr
                    565             570             575
    Gly Asn Phe Ser Ile Arg Leu Leu Arg Gly Gly Val Ser Ile Gly Asp
                580             585             590
    Val Arg Leu Gly Ser Thr Met Asn Arg Gly Gln Glu Leu Thr Tyr Glu
                595             600             605
```

-continued

Ser Phe Phe Thr Arg Glu Phe Thr Thr Thr Gly Pro Phe Asn Pro Pro
610                     615                     620

Phe Thr Phe Thr Gln Ala Gln Glu Ile Leu Thr Val Asn Ala Glu Gly
625                     630                     635                 640

Val Ser Thr Gly Gly Glu Tyr Tyr Ile Asp Arg Ile Glu Ile Val Pro
                645                     650                     655

Val Asn Pro Ala Arg Glu Ala Glu Glu Asp Leu Glu Ala Ala Lys Lys
                660                     665                     670

Ala Val Ala Ser Leu Phe Thr Arg Thr Arg Asp Gly Leu Gln Val Asn
        675                     680                     685

Val Thr Asp Tyr Gln Val Asp Arg Ala Ala Asn Leu Val Ser Cys Leu
        690                     695                     700

Ser Asp Glu Gln Tyr Ser His Asp Lys Lys Met Leu Leu Glu Ala Val
705                     710                     715                 720

Arg Ala Ala Lys Arg Leu Ser Arg Glu Arg Asn Leu Leu Gln Asp Pro
                725                     730                     735

Asp Phe Asn Thr Ile Asn Ser Thr Glu Glu Asn Gly Trp Lys Ala Ser
                740                     745                     750

Asn Gly Val Thr Ile Ser Glu Gly Gly Pro Phe Phe Lys Gly Arg Ala
        755                     760                     765

Leu Gln Leu Ala Ser Ala Arg Glu Asn Tyr Pro Thr Tyr Ile Tyr Gln
770                     775                     780

Lys Val Asp Ala Ser Val Leu Lys Pro Tyr Thr Arg Tyr Arg Leu Asp
785                     790                     795                 800

Gly Phe Val Lys Ser Ser Gln Asp Leu Glu Ile Asp Leu Ile His His
                805                     810                     815

His Lys Val His Leu Val Lys Asn Val Pro Asp Asn Leu Val Ser Asp
                820                     825                     830

Thr Tyr Ser Asp Gly Ser Cys Ser Gly Ile Asn Arg Cys Asp Glu Gln
        835                     840                     845

Gln Gln Val Asp Met Gln Leu Asp Ala Glu His His Pro Met Asp Cys
        850                     855                     860

Cys Glu Ala Ala Gln Thr His Glu Phe Ser Ser Tyr Ile Asn Thr Gly
865                     870                     875                 880

Asp Leu Asn Ala Ser Val Asp Gln Gly Ile Trp Val Val Leu Lys Val
                885                     890                     895

Arg Thr Thr Asp Gly Tyr Ala Thr Leu Gly Asn Leu Glu Leu Val Glu
                900                     905                     910

Val Gly Pro Leu Ser Gly Glu Ser Leu Glu Arg Glu Gln Arg Asp Asn
        915                     920                     925

Ala Lys Trp Asn Ala Glu Leu Gly Arg Lys Arg Ala Glu Thr Asp Arg
        930                     935                     940

Val Tyr Leu Ala Ala Lys Gln Ala Ile Asn His Leu Phe Val Asp Tyr
945                     950                     955                 960

Gln Asp Gln Gln Leu Asn Pro Glu Ile Gly Leu Ala Glu Ile Asn Glu
                965                     970                     975

Ala Ser Asn Leu Val Lys Ser Ile Ser Gly Val Tyr Ser Asp Thr Leu
                980                     985                     990

Leu Gln Ile Pro Gly Ile Asn Tyr Glu Ile Tyr Thr Glu Leu Ser Asp
        995                     1000                    1005

Arg Leu Gln Gln Ala Ser Tyr Leu Tyr Thr Ser Arg Asn Ala Val
    1010                    1015                    1020

```
Gln Asn Gly Asp Phe Asn Ser Gly Leu Asp Ser Trp Asn Ala Thr
    1025                1030                1035

Thr Asp Ala Ser Val Gln Gln Asp Gly Ser Thr His Phe Leu Val
    1040                1045                1050

Leu Ser His Trp Asp Ala Gln Val Ser Gln Gln Met Arg Val Asn
    1055                1060                1065

Leu Asn Cys Lys Tyr Val Leu Arg Val Thr Ala Lys Lys Val Gly
    1070                1075                1080

Gly Gly Asp Gly Tyr Val Thr Ile Arg Asp Gly Ala His His Gln
    1085                1090                1095

Glu Thr Leu Thr Phe Asn Ala Cys Asp Tyr Asp Val Asn Gly Thr
    1100                1105                1110

Tyr Val Asn Asp Asn Ser Tyr Ile Thr Lys Glu Val Val Phe Tyr
    1115                1120                1125

Pro Glu Thr Lys His Met Trp Val Glu Val Ser Glu Ser Glu Gly
    1130                1135                1140

Ser Phe Tyr Ile Asp Ser Ile Glu Phe Ile Glu Thr Gln Glu
    1145                1150                1155

<210> SEQ ID NO 15
<211> LENGTH: 1173
<212> TYPE: PRT
<213> ORGANISM: Bacillus thuringiensis

<400> SEQUENCE: 15

Met Asn Arg Asn Asn Gln Gly Glu Tyr Glu Ile Ile Asp Ala Ser Thr
1               5                   10                  15

Cys Gly Cys Ser Ser Asp Asp Val Val Gln Tyr Pro Leu Ala Arg Asp
                20                  25                  30

Pro Asn Ala Ala Phe Gln Asn Met Asn Tyr Lys Asp Tyr Leu Lys Met
            35                  40                  45

Ser Asp Gly Asp Tyr Val Asp Ser Tyr Ile Asn Pro Gly Leu Ser Ile
        50                  55                  60

Gly Arg Arg Asp Val Thr Leu Thr Gly Val Gly Ile Val Ala Leu Ile
65                  70                  75                  80

Val Gly Thr Leu Gly Gly Pro Val Gly Gly Ile Val Thr Gly Leu Ile
                85                  90                  95

Ser Ser Leu Leu Gly Leu Leu Trp Pro Ser Asp Asn Asp Val Trp
            100                 105                 110

Glu Ala Phe Met Ala Gln Ile Glu Glu Leu Ile Glu Gln Arg Ile Ala
            115                 120                 125

Asp Gln Val Val Arg Asn Ala Leu Asp Asn Leu Thr Gly Leu Arg Asp
        130                 135                 140

Tyr Tyr Asn Gln Tyr Leu Leu Ala Leu Glu Glu Trp Gln Glu Arg Pro
145                 150                 155                 160

Asn Ala Val Arg Ser Thr Leu Val Phe Asn Arg Phe Glu Thr Leu His
                165                 170                 175

Ser His Phe Val Thr Ser Met Pro Ser Phe Gly Ser Gly Pro Gly Ser
            180                 185                 190

Glu Arg Tyr Ala Val Gln Leu Leu Thr Val Tyr Ala Gln Ala Ala Asn
        195                 200                 205

Leu His Leu Leu Leu Leu Arg Asp Ala Asp Ile Tyr Gly Ala Arg Trp
    210                 215                 220

Gly Leu Arg Glu Ser Gln Ile Asp Leu Tyr Phe Asn Glu Leu Gln Asn
225                 230                 235                 240
```

```
Arg Thr Arg Asp Tyr Thr Asn His Cys Val Thr Ala Tyr Asn Asn Gly
                245                 250                 255

Leu Glu Glu Ile Arg Gly Thr Ser Pro Ala Ser Trp Leu Arg Tyr His
            260                 265                 270

Gln Phe Arg Arg Glu Thr Thr Leu Ile Ala Leu Asp Leu Val Ala Ile
        275                 280                 285

Phe Pro Tyr Tyr Asn Val Arg Glu Tyr Pro Ile Gly Val Asn Pro Gln
    290                 295                 300

Leu Thr Arg Asp Val Tyr Thr Asp Pro Ile Gly Val Thr Phe Arg Arg
305                 310                 315                 320

Glu Asp Trp Glu Thr Gly Val Glu Cys Arg Pro Trp Val Asn Thr Pro
                325                 330                 335

Tyr Met Ser Phe Ser Asp Leu Glu Asn Ala Ile Ile Arg Pro Pro His
            340                 345                 350

Leu Phe Glu Thr Leu Arg Asn Leu Thr Ile His Thr Gly Arg Tyr Asn
        355                 360                 365

Leu Val Gly Gly Ala Arg Phe Ile Glu Gly Trp Val Gly His Ser Val
    370                 375                 380

Thr Asn Thr Arg Leu Gly Asn Ser Thr Val Phe Thr Ser Asn Tyr Gly
385                 390                 395                 400

Ser Leu Pro Pro Arg Phe Gln Val Phe Asn Phe Thr Asn Phe Asp Val
                405                 410                 415

Tyr Gln Ile Asn Thr Arg Ala Asp Ser Thr Gly Thr Phe Arg Ile Pro
            420                 425                 430

Gly Phe Ala Val Thr Arg Ala Gln Phe Ile Pro Gly Thr Tyr Ser
        435                 440                 445

Val Ala His Arg Asp Pro Gly Ala Cys Gln Gln Asp Tyr Asp Ser Ile
    450                 455                 460

Glu Glu Leu Pro Ser Leu Asp Pro Asp Glu Pro Ile Asn Arg Ser Tyr
465                 470                 475                 480

Ser His Arg Leu Ser His Val Thr Leu Tyr Lys Tyr Thr Leu Ser Asp
                485                 490                 495

Thr Asp Tyr Gly Val Ile Asn Tyr Thr Asp Tyr Gly Ser Met Pro Ala
            500                 505                 510

Tyr Val Trp Thr His Arg Asp Val Asp Leu Thr Asn Thr Ile Thr Ala
        515                 520                 525

Asp Arg Ile Thr Gln Leu Pro Leu Val Lys Ala Ser Thr Leu Pro Ala
    530                 535                 540

Gly Thr Thr Val Val Lys Gly Pro Gly Phe Thr Gly Gly Asp Ile Leu
545                 550                 555                 560

Arg Arg Thr Thr Asn Gly Thr Phe Gly Thr Leu His Val Arg Val Asn
                565                 570                 575

Ser Pro Leu Thr Gln Gln Tyr Arg Leu Arg Val Arg Phe Ala Ser Thr
            580                 585                 590

Gly Asn Phe Ser Ile Arg Val Leu Arg Gly Gly Thr Ser Ile Gly Asp
        595                 600                 605

Ala Arg Phe Gly Ser Thr Met Asn Arg Gly Gln Glu Leu Thr Tyr Glu
    610                 615                 620

Ser Phe Val Thr Arg Glu Phe Thr Thr Thr Gly Pro Phe Asn Pro Pro
625                 630                 635                 640

Phe Thr Phe Thr Gln Thr Gln Glu Ile Leu Thr Val Asn Ala Glu Gly
                645                 650                 655
```

```
Val Ser Thr Gly Gly Glu Tyr Tyr Ile Asp Ser Ile Glu Ile Val Pro
            660                 665                 670

Val Asn Pro Thr Arg Glu Ala Glu Asp Leu Glu Ala Ala Lys Lys
        675                 680                 685

Ala Val Ala Ser Leu Phe Thr Arg Thr Arg Asp Gly Leu Gln Val Asn
    690                 695                 700

Val Thr Asp Tyr Gln Val Asp Arg Ala Ala Asn Leu Val Leu Cys Leu
705                 710                 715                 720

Ser Asp Glu Gln Tyr Ala His Asp Lys Lys Met Leu Leu Glu Ala Val
                725                 730                 735

Arg Ala Ala Lys Arg Leu Ser Arg Glu Arg Asn Leu Leu Gln Asp Pro
            740                 745                 750

Asp Phe Asn Glu Ile Asn Ser Thr Glu Asp Ser Gly Trp Lys Thr Ser
        755                 760                 765

Asn Gly Ile Ile Ile Ser Glu Gly Pro Phe Phe Lys Gly Arg Ala
    770                 775                 780

Leu Gln Leu Ala Ser Ala Arg Glu Asn Tyr Pro Thr Tyr Ile Tyr Gln
785                 790                 795                 800

Lys Val Asp Ser Ser Met Leu Lys Pro Tyr Thr Arg Tyr Lys Leu Asp
                805                 810                 815

Gly Phe Val Gln Ser Gln Asp Leu Glu Ile Glu Leu Ile His His
            820                 825                 830

His Lys Val His Leu Val Lys Asn Val Pro Asp Asn Leu Val Leu Asp
            835                 840                 845

Thr Tyr Pro Asp Gly Ser Cys Asn Gly Ile Asn Arg Cys Glu Glu Gln
    850                 855                 860

Gln Met Val Asn Ser Gln Leu Glu Thr Glu His His Pro Met Asp Cys
865                 870                 875                 880

Cys Glu Ala Ser Gln Thr His Glu Phe Ser Ser Tyr Ile His Thr Gly
            885                 890                 895

Asp Leu Asn Ala Ser Val Asp Gln Gly Ile Trp Val Val Leu Lys Ile
        900                 905                 910

Arg Thr Thr Asp Gly Ser Ala Thr Leu Gly Asn Leu Glu Leu Val Glu
    915                 920                 925

Val Gly Pro Leu Ser Gly Glu Ser Leu Glu Arg Glu Gln Arg Asp Asn
930                 935                 940

Ala Lys Trp Asn Ala Glu Leu Gly Arg Lys Arg Ala Glu Ala Asp Arg
945                 950                 955                 960

Val Tyr Gln Gly Ala Lys Gln Ala Ile Asn His Leu Phe Val Asp Tyr
            965                 970                 975

Gln Asp Gln Gln Leu Asn Pro Glu Val Gly Leu Ala Glu Ile Ser Glu
        980                 985                 990

Ala Arg Asn Leu Ile Glu Ser Ile Ser Asp Val Tyr Cys Asp Ala Val
    995                 1000                1005

Leu Arg Ile Pro Gly Ile Asn Tyr Glu Met Tyr Thr Glu Leu Ser
    1010                1015                1020

Asn Arg Leu Gln Gln Ala Ala Tyr Leu Tyr Thr Ser Arg Asn Ala
    1025                1030                1035

Val Gln Asn Gly Asp Phe Asn Ser Gly Leu Asp Ser Trp Asn Ala
    1040                1045                1050

Thr Thr Asp Ala Thr Val Gln Gln Asp Gly Asn Met Tyr Phe Leu
    1055                1060                1065

Val Leu Ser His Trp Asp Ala Gln Val Ser Gln Gln Phe Arg Val
```

```
    1070                1075                1080

Gln Pro  Asn Cys Lys Tyr Val  Leu Arg Val Thr Ala  Lys Lys Val
    1085                1090                1095

Gly Asn  Gly Asp Gly Tyr Val  Thr Ile Gln Asp Gly  Ala His His
    1100                1105                1110

Arg Glu  Thr Leu Thr Phe Asn  Ala Cys Asp Tyr Asp  Val Asn Gly
    1115                1120                1125

Thr His  Val Asn Asp Asn Ser  Tyr Ile Thr Lys Glu  Leu Glu Phe
    1130                1135                1140

Tyr Pro  Lys Thr Glu His Met  Trp Val Glu Val Ser  Glu Thr Glu
    1145                1150                1155

Gly Thr  Phe Tyr Ile Asp Ser  Ile Glu Leu Ile Glu  Thr Gln Glu
    1160                1165                1170

<210> SEQ ID NO 16
<211> LENGTH: 1179
<212> TYPE: PRT
<213> ORGANISM: Bacillus thuringiensis

<400> SEQUENCE: 16

Met Gly Gly Lys Ser Met Asn Arg Asn Asn Gln Gly Glu Tyr Glu Ile
1               5                   10                  15

Ile Asp Ala Ser Thr Cys Gly Cys Ser Ser Asp Asp Val Val Gln Tyr
            20                  25                  30

Pro Leu Ala Arg Asp Pro Asn Ala Ala Phe Gln Asn Met Asn Tyr Lys
        35                  40                  45

Asp Tyr Leu Lys Met Ser Asp Gly Asp Tyr Val Asp Ser Tyr Ile Asn
    50                  55                  60

Pro Gly Leu Ser Ile Gly Arg Arg Asp Val Thr Leu Thr Gly Val Gly
65                  70                  75                  80

Ile Val Ala Leu Ile Val Gly Thr Leu Gly Gly Pro Val Gly Gly Ile
                85                  90                  95

Val Thr Gly Leu Ile Ser Ser Leu Leu Gly Leu Leu Trp Pro Ser Asn
            100                 105                 110

Asp Asn Asp Val Trp Glu Ala Phe Met Ala Gln Ile Glu Glu Leu Ile
        115                 120                 125

Glu Gln Arg Ile Ala Asp Gln Val Val Arg Asn Ala Leu Asp Asn Leu
    130                 135                 140

Thr Gly Leu Arg Asp Tyr Tyr Asn Gln Tyr Leu Leu Ala Leu Glu Glu
145                 150                 155                 160

Trp Gln Glu Arg Pro Asn Ala Val Arg Ser Thr Leu Val Phe Asn Arg
                165                 170                 175

Phe Glu Thr Leu His Ser His Phe Val Thr Ser Met Pro Ser Phe Gly
            180                 185                 190

Ser Gly Pro Gly Ser Glu Arg Tyr Ala Val Gln Leu Leu Thr Val Tyr
        195                 200                 205

Ala Gln Ala Ala Asn Leu His Leu Leu Leu Leu Arg Asp Ala Asp Ile
    210                 215                 220

Tyr Gly Ala Arg Trp Gly Leu Arg Glu Ser Gln Ile Asp Leu Tyr Phe
225                 230                 235                 240

Asn Glu Leu Gln Asn Arg Thr Arg Asp Tyr Thr Asn His Cys Val Thr
                245                 250                 255

Ala Tyr Asn Asn Gly Leu Glu Glu Ile Arg Gly Thr Ser Pro Ala Ser
            260                 265                 270
```

```
Trp Leu Arg Tyr His Gln Phe Arg Arg Glu Thr Thr Leu Ile Ala Leu
            275                 280                 285

Asp Leu Val Ala Ile Phe Pro Tyr Tyr Asn Val Arg Glu Tyr Pro Ile
        290                 295                 300

Gly Val Asn Pro Gln Leu Thr Arg Asp Val Tyr Thr Asp Pro Ile Gly
305                 310                 315                 320

Val Thr Phe Arg Arg Glu Asp Trp Glu Thr Gly Val Glu Cys Arg Pro
                325                 330                 335

Trp Val Asn Thr Pro Tyr Met Ser Phe Ser Asp Leu Glu Asn Ala Ile
                340                 345                 350

Ile Arg Pro Pro His Leu Phe Glu Thr Leu Arg Asn Leu Thr Ile His
                355                 360                 365

Thr Gly Arg Tyr Asn Leu Val Gly Gly Ala Arg Phe Ile Glu Gly Trp
        370                 375                 380

Val Gly His Ser Val Thr Asn Thr Arg Leu Gly Asn Ser Thr Val Phe
385                 390                 395                 400

Thr Ser Asn Tyr Gly Ser Leu Pro Pro Arg Phe Gln Val Phe Asn Phe
                405                 410                 415

Thr Asn Phe Asp Val Tyr Gln Ile Asn Thr Arg Ala Asp Ser Thr Gly
            420                 425                 430

Thr Phe Arg Ile Pro Gly Phe Ala Val Thr Arg Ala Gln Phe Ile Pro
        435                 440                 445

Gly Gly Thr Tyr Ser Val Ala His Arg Asp Pro Gly Ala Cys Gln Gln
        450                 455                 460

Asp Tyr Asp Ser Ile Glu Glu Leu Pro Ser Leu Asp Pro Asp Glu Pro
465                 470                 475                 480

Ile Asn Arg Ser Tyr Ser His Arg Leu Ser His Val Thr Leu Tyr Lys
                485                 490                 495

Tyr Thr Leu Ser Asp Thr Asp Tyr Gly Val Ile Asn Tyr Thr Asp Tyr
                500                 505                 510

Gly Ser Met Pro Ala Tyr Val Trp Thr His Arg Asp Val Asp Leu Thr
        515                 520                 525

Asn Thr Ile Thr Ala Asp Arg Ile Thr Gln Leu Pro Leu Val Lys Ala
530                 535                 540

Ser Thr Leu Pro Ala Gly Thr Thr Val Val Lys Gly Pro Gly Phe Thr
545                 550                 555                 560

Gly Gly Asp Ile Leu Arg Arg Thr Thr Asn Gly Thr Phe Gly Thr Leu
                565                 570                 575

His Val Arg Val Asn Ser Pro Leu Thr Gln Gln Tyr Arg Leu Arg Val
                580                 585                 590

Arg Phe Ala Ser Thr Gly Asn Phe Ser Ile Arg Val Leu Arg Gly Gly
        595                 600                 605

Thr Ser Ile Gly Asp Ala Arg Phe Gly Ser Thr Met Asn Arg Gly Gln
        610                 615                 620

Glu Leu Thr Tyr Glu Ser Phe Val Thr Arg Glu Phe Thr Thr Thr Gly
625                 630                 635                 640

Pro Phe Asn Pro Pro Phe Thr Phe Thr Gln Thr Gln Glu Ile Leu Thr
                645                 650                 655

Val Asn Ala Glu Gly Val Ser Thr Gly Gly Glu Tyr Tyr Ile Asp Ser
            660                 665                 670

Ile Glu Ile Val Pro Val Asn Pro Thr Arg Glu Ala Glu Glu Asp Leu
        675                 680                 685

Glu Ala Ala Lys Lys Ala Val Ala Ser Leu Phe Thr Arg Thr Arg Asp
```

```
                690             695             700
    Gly Leu Gln Val Asn Val Thr Asp Tyr Gln Val Asp Gln Ala Ala Asn
    705                 710                 715                 720
    Leu Val Ser Cys Leu Ser Asp Glu Gln Tyr Gly Tyr Asp Lys Lys Met
                    725                 730                 735
    Leu Leu Glu Ala Val Arg Ala Ala Lys Arg Leu Ser Arg Glu Arg Asn
                    740                 745                 750
    Leu Leu Gln Asp Pro Asp Phe Asn Thr Ile Asn Ser Thr Glu Glu Asn
                    755                 760                 765
    Gly Trp Lys Ala Ser Asn Gly Val Thr Ile Ser Glu Gly Gly Pro Phe
    770                 775                 780
    Tyr Lys Gly Arg Ala Leu Gln Leu Ala Ser Ala Arg Glu Asn Tyr Pro
    785                 790                 795                 800
    Thr Tyr Ile Tyr Gln Lys Val Asp Ala Ser Glu Leu Lys Pro Tyr Thr
                    805                 810                 815
    Arg Tyr Arg Leu Asp Gly Phe Val Lys Ser Ser Gln Asp Leu Glu Ile
                    820                 825                 830
    Asp Leu Ile His His His Lys Val His Leu Val Lys Asn Val Pro Asp
                    835                 840                 845
    Asn Leu Val Ser Asp Thr Tyr Pro Asp Asp Ser Cys Ser Gly Ile Asn
    850                 855                 860
    Arg Cys Gln Glu Gln Gln Met Val Asn Ala Gln Leu Glu Thr Glu His
    865                 870                 875                 880
    His His Pro Met Asp Cys Cys Glu Ala Ala Gln Thr His Glu Phe Ser
                    885                 890                 895
    Ser Tyr Ile Asp Thr Gly Asp Leu Asn Ser Ser Val Asp Gln Gly Ile
                    900                 905                 910
    Trp Ala Ile Phe Lys Val Arg Thr Thr Asp Gly Tyr Ala Thr Leu Gly
                    915                 920                 925
    Asn Leu Glu Leu Val Glu Val Gly Pro Leu Ser Gly Glu Ser Leu Glu
    930                 935                 940
    Arg Glu Gln Arg Asp Asn Thr Lys Trp Ser Ala Glu Leu Gly Arg Lys
    945                 950                 955                 960
    Arg Ala Glu Thr Asp Arg Val Tyr Gln Asp Ala Lys Gln Ser Ile Asn
                    965                 970                 975
    His Leu Phe Val Asp Tyr Gln Asp Gln Gln Leu Asn Pro Glu Ile Gly
                    980                 985                 990
    Met Ala Asp Ile Met Asp Ala Gln Asn Leu Val Ala Ser Ile Ser Asp
                    995                 1000                1005
    Val Tyr Ser Asp Ala Val Leu Gln Ile Pro Gly Ile Asn Tyr Glu
                    1010                1015                1020
    Ile Tyr Thr Glu Leu Ser Asn Arg Leu Gln Gln Ala Ser Tyr Leu
                    1025                1030                1035
    Tyr Thr Ser Arg Asn Ala Val Gln Asn Gly Asp Phe Asn Asn Gly
                    1040                1045                1050
    Leu Asp Ser Trp Asn Ala Thr Ala Gly Ala Ser Val Gln Gln Asp
                    1055                1060                1065
    Gly Asn Thr His Phe Leu Val Leu Ser His Trp Asp Ala Gln Val
                    1070                1075                1080
    Ser Gln Gln Phe Arg Val Gln Pro Asn Cys Lys Tyr Val Leu Arg
                    1085                1090                1095
    Val Thr Ala Glu Lys Val Gly Gly Gly Asp Gly Tyr Val Thr Ile
                    1100                1105                1110
```

```
Arg Asp Gly Ala His His Thr Glu Thr Leu Thr Phe Asn Ala Cys
1115                1120                1125

Asp Tyr Asp Ile Asn Gly Thr Tyr Val Thr Asp Asn Thr Tyr Leu
1130                1135                1140

Thr Lys Glu Val Ile Phe Tyr Ser His Thr Glu His Met Trp Val
1145                1150                1155

Glu Val Asn Glu Thr Glu Gly Ala Phe His Ile Asp Ser Ile Glu
1160                1165                1170

Phe Val Glu Thr Glu Lys
1175

<210> SEQ ID NO 17
<211> LENGTH: 1147
<212> TYPE: PRT
<213> ORGANISM: Artificial Sequence
<220> FEATURE:
<223> OTHER INFORMATION: Mutant BT-0044

<400> SEQUENCE: 17

Met Asp Leu Asp Gly Asn Lys Thr Glu Thr Glu Thr Glu Ile Val Asn
1               5                   10                  15

Gly Ser Glu Ser Ser Ile Asp Pro Ser Ser Val Ser Tyr Ala Gly Asn
                20                  25                  30

Asn Ser Tyr Ser Ser Ala Leu Asn Leu Asn Ser Cys Gln Asn Arg Gly
            35                  40                  45

Ile Ala Gln Trp Val Asn Thr Leu Gly Gly Ala Ile Gly Gln Ala Val
50                  55                  60

Ser Ile Gly Thr Ser Ile Ile Ser Leu Leu Ala Ala Pro Thr Leu Thr
65                  70                  75                  80

Gly Ser Ile Ser Leu Ala Phe Asn Leu Ile Arg Arg Met Gly Thr Gly
                85                  90                  95

Ser Asn Gly Ser Ser Ile Ser Asp Leu Ser Ile Cys Asp Leu Leu Ser
            100                 105                 110

Ile Ile Asn Leu Arg Val Ser Gln Ala Val Leu Asn Asp Gly Ile Ala
        115                 120                 125

Asp Phe Asn Gly Ser Val Ala Val Tyr Asp Leu Tyr Leu His Ala Leu
    130                 135                 140

Arg Ser Trp Asn Asn Pro Asn Ala Ala Thr Ala Glu Glu Leu Arg
145                 150                 155                 160

Thr Arg Phe Arg Ile Ala Asp Ser Glu Phe Glu Arg Ile Leu Thr Arg
                165                 170                 175

Gly Ser Leu Thr His Gly Gly Ser Leu Ala Arg Gln Asp Ala Gln Val
            180                 185                 190

Leu Leu Leu Pro Ser Phe Val Asn Ala Ala Tyr Leu His Leu Ile
        195                 200                 205

Leu Arg Asp Ala Ser Arg Tyr Gly Ala Ser Trp Gly Leu Phe Asn Thr
    210                 215                 220

Thr Pro His Ile Asn Tyr Pro Val Arg Leu Gln Gln Leu Ile Gly Ser
225                 230                 235                 240

Tyr Thr His Tyr Cys Thr His Trp Tyr Asn Gln Gly Leu Asn Glu Ile
                245                 250                 255

Arg Gln Arg Gly Asn Thr Ala Val Asn Trp Leu Glu Phe His Arg Tyr
            260                 265                 270

Arg Arg Asp Met Thr Leu Met Val Leu Asp Val Val Ser Leu Phe Ser
        275                 280                 285
```

```
Ala Leu Asp Thr Ile Arg Tyr Pro Asn Ala Thr Val Val Gln Leu Ser
        290                 295                 300

Arg Thr Val Tyr Thr Asp Pro Ile Gly Phe Val Asn Arg Gly Ser Gly
305                 310                 315                 320

Asn Arg Leu Ser Trp Phe Asp Trp Arg Asn Gln Ala Asn Phe Ser Thr
                325                 330                 335

Leu Glu Ser Glu Met Pro Thr Pro Ser Ser Pro Leu Ser Leu Asn His
            340                 345                 350

Met Ser Ile Phe Thr Gly Pro Leu Thr Leu Pro Val Ser Pro Asn Thr
        355                 360                 365

His Arg Ala Arg Val Trp Tyr Gly Asn Gln Asn Met Phe Thr Thr Gly
    370                 375                 380

Ser Gln Asn Ser Gly Gln Thr Thr Asn Ser Ile Gln Asn Ile Ser Gly
385                 390                 395                 400

Leu Glu Ile Phe Arg Ile Asp Ser Gln Ala Cys Asn Leu Asn Asn Asn
                405                 410                 415

Ser Tyr Gly Val Asn Arg Ala Glu Phe Phe His Gly Ala Ser Gln Gly
                420                 425                 430

Ser Gln Arg Ser Val Tyr Gln Gly Tyr Ile Arg Gln Ser Gly Leu Asp
            435                 440                 445

Asn Pro Val Val Met Asn Leu Gln Ser Phe Leu Pro Gly Glu Asn Ser
450                 455                 460

Ala Thr Pro Thr Ala Gln Asp Tyr Thr His Ile Leu Ser Asn Pro Val
465                 470                 475                 480

Asn Ile Arg Gly Gly Leu Arg Gln Ile Val Ala Asp Arg Arg Ser Ser
                485                 490                 495

Val Val Val Tyr Gly Trp Thr His Lys Ser Leu Ser Arg Arg Ser Leu
            500                 505                 510

Val Ala Pro Asp Gln Ile Thr Gln Val Pro Ala Val Lys Ala Ser Pro
            515                 520                 525

Ser Ser His Cys Thr Ile Ile Ala Gly Pro Gly Phe Thr Gly Gly Asp
530                 535                 540

Leu Val Ser Leu Gln Pro Asn Gly Gln Leu Val Ile Pro Phe Gln Val
545                 550                 555                 560

Ser Ala Pro Glu Thr Asn Tyr His Ile Arg Ile Cys Tyr Val Ser Thr
                565                 570                 575

Ser Asp Cys Ser Ile Asn Thr Ile Cys Asn Asp Glu Thr His Leu Ser
            580                 585                 590

Thr Leu Pro Ser Thr Thr Ser Ser Leu Glu Asn Leu Gln Cys Asn His
        595                 600                 605

Leu His Tyr Phe Asn Val Gly Thr Phe Lys Pro Thr Ile Asp Ser Lys
    610                 615                 620

Leu Thr Leu Val Asn Thr Ser Pro Asn Ala Asn Ile Ile Asp Lys
625                 630                 635                 640

Ile Glu Phe Ile Pro Val Asp Thr Ala Gln Gln Asn Glu Asp Leu
                645                 650                 655

Glu Ala Ala Lys Lys Ala Val Ala Ser Leu Phe Thr Arg Thr Arg Asp
            660                 665                 670

Gly Leu Gln Val Asn Val Lys Asp Tyr Gln Val Asp Gln Ala Ala Asn
        675                 680                 685

Leu Val Ser Cys Leu Ser Asp Glu Gln Tyr Gly Tyr Asp Lys Lys Met
    690                 695                 700
```

```
Leu Leu Glu Ala Val Arg Ala Ala Lys Arg Leu Ser Arg Glu Arg Asn
705                 710                 715                 720

Leu Leu Gln Asp Pro Asp Phe Asn Thr Ile Asn Ser Thr Glu Asn
            725                 730                 735

Gly Trp Lys Ala Ser Asn Gly Val Thr Ile Ser Glu Gly Gly Pro Phe
                740                 745                 750

Tyr Lys Gly Arg Ala Ile Gln Leu Ala Ser Ala Arg Glu Asn Tyr Pro
            755                 760                 765

Thr Tyr Ile Tyr Gln Lys Val Asp Ala Ser Glu Leu Lys Pro Tyr Thr
            770                 775                 780

Arg Tyr Arg Leu Asp Gly Phe Val Lys Ser Ser Gln Asp Leu Glu Ile
785                 790                 795                 800

Asp Leu Ile His His His Lys Val His Leu Val Lys Asn Val Pro Asp
                805                 810                 815

Asn Leu Val Ser Asp Thr Tyr Pro Asp Asp Ser Cys Ser Gly Ile Asn
            820                 825                 830

Arg Cys Gln Glu Gln Gln Met Val Asn Ala Gln Leu Glu Thr Glu His
            835                 840                 845

His His Pro Met Asp Cys Cys Glu Ala Ala Gln Thr His Glu Phe Ser
850                 855                 860

Ser Tyr Ile Asp Thr Gly Asp Leu Asn Ser Ser Val Asp Gln Gly Ile
865                 870                 875                 880

Trp Ala Ile Phe Lys Val Arg Thr Thr Asp Gly Tyr Ala Thr Leu Gly
                885                 890                 895

Asn Leu Glu Leu Val Glu Val Gly Pro Leu Ser Gly Glu Ser Leu Glu
            900                 905                 910

Arg Glu Gln Arg Asp Asn Thr Lys Trp Ser Ala Glu Leu Gly Arg Lys
            915                 920                 925

Arg Ala Glu Thr Asp Arg Val Tyr Gln Asp Ala Lys Gln Ser Ile Asn
930                 935                 940

His Leu Phe Val Asp Tyr Gln Asp Gln Gln Leu Asn Pro Glu Ile Gly
945                 950                 955                 960

Met Ala Asp Ile Met Asp Ala Gln Asn Leu Val Ala Ser Ile Ser Asp
                965                 970                 975

Val Tyr Ser Asp Ala Val Leu Gln Ile Pro Gly Ile Asn Tyr Glu Ile
            980                 985                 990

Tyr Thr Glu Leu Ser Asn Arg Leu Gln Gln Ala Ser Tyr Leu Tyr Thr
            995                 1000                1005

Ser Arg Asn Ala Val Gln Asn Gly Asp Phe Asn Asn Gly Leu Asp
    1010                1015                1020

Ser Trp Asn Ala Thr Ala Gly Ala Ser Val Gln Gln Asp Gly Asn
    1025                1030                1035

Thr His Phe Leu Val Leu Ser His Trp Asp Ala Gln Val Ser Gln
    1040                1045                1050

Gln Phe Arg Val Gln Pro Asn Cys Lys Tyr Val Leu Arg Val Thr
    1055                1060                1065

Ala Glu Lys Val Gly Gly Gly Asp Gly Tyr Val Thr Ile Arg Asp
    1070                1075                1080

Asp Ala His His Thr Glu Thr Leu Thr Phe Asn Ala Cys Asp Tyr
    1085                1090                1095

Asp Ile Asn Gly Thr Tyr Val Thr Asp Asn Thr Tyr Ile Thr Lys
    1100                1105                1110

Glu Val Val Phe His Pro Glu Thr Gln His Met Trp Val Glu Val
```

```
                1115                1120                1125

Asn Glu  Thr Glu Gly Ala Phe  His Leu Asp Ser Ile  Glu Phe Val
         1130                1135                1140

Glu Thr  Glu Lys
         1145

<210> SEQ ID NO 18
<211> LENGTH: 1157
<212> TYPE: PRT
<213> ORGANISM: Artificial Sequence
<220> FEATURE:
<223> OTHER INFORMATION: Mutant BT-0051

<400> SEQUENCE: 18

Met Asn Arg Asn Asn Gln Asn Glu Tyr Glu Ile Ile Asp Ala Pro His
1               5                   10                  15

Cys Gly Cys Pro Ser Asp Asp Val Lys Tyr Pro Leu Ala Ser Asp
            20                  25                  30

Pro Asn Ala Ala Leu Gln Asn Met Asn Tyr Lys Asp Tyr Leu Gln Met
        35                  40                  45

Thr Asp Glu Asp Tyr Thr Asp Ser Tyr Ile Asn Pro Ser Leu Ser Ile
50                  55                  60

Ser Gly Arg Asp Ala Val Gln Thr Ala Leu Thr Val Val Gly Arg Ile
65                  70                  75                  80

Leu Gly Ala Leu Gly Val Pro Phe Ser Gly Gln Ile Val Ser Phe Tyr
                85                  90                  95

Gln Phe Leu Leu Asn Thr Leu Trp Pro Val Asn Asp Thr Ala Ile Trp
            100                 105                 110

Glu Ala Phe Met Arg Gln Val Glu Glu Leu Val Asn Gln Gln Ile Thr
        115                 120                 125

Glu Phe Ala Arg Asn Gln Ala Leu Ala Arg Leu Gln Gly Leu Gly Asp
130                 135                 140

Ser Phe Asn Val Tyr Gln Arg Ser Leu Gln Asn Trp Leu Ala Asp Arg
145                 150                 155                 160

Asn Asp Thr Arg Asn Leu Ser Val Val Arg Ala Gln Phe Ile Ala Leu
                165                 170                 175

Asp Leu Asp Phe Val Asn Ala Ile Pro Leu Phe Ala Val Asn Gly Gln
            180                 185                 190

Gln Val Pro Leu Leu Ser Val Tyr Ala Gln Ala Val Asn Leu His Leu
        195                 200                 205

Leu Leu Leu Lys Asp Ala Ser Leu Phe Gly Glu Gly Trp Gly Phe Thr
210                 215                 220

Gln Gly Glu Ile Ser Thr His Tyr Asp Arg Gln Leu Glu Leu Thr Ala
225                 230                 235                 240

Arg Tyr Thr Asn Tyr Cys Glu Thr Trp Tyr Asn Thr Gly Leu Asp Arg
                245                 250                 255

Leu Arg Gly Thr Asn Thr Glu Ser Trp Leu Arg Tyr His Gln Phe Arg
            260                 265                 270

Arg Glu Met Thr Leu Val Val Leu Asp Val Val Ala Leu Phe Pro Tyr
        275                 280                 285

Tyr Asp Val Arg Leu Tyr Pro Thr Gly Ser Asn Pro Gln Leu Thr Arg
290                 295                 300

Glu Val Tyr Thr Asp Pro Ile Val Phe Asn Pro Pro Ala Asn Val Gly
305                 310                 315                 320

Leu Cys Arg Arg Trp Gly Thr Asn Pro Tyr Asn Thr Phe Ser Glu Leu
```

```
                    325                 330                 335
Glu Asn Ala Phe Ile Arg Pro Pro His Leu Phe Asp Arg Ile Gln Ser
                340                 345                 350
Leu Ser Ile Ser Ser Asn Arg Phe Pro Val Ser Ser Asn Phe Met Asp
                355                 360                 365
Tyr Trp Ser Gly His Thr Leu Arg Arg Ser Tyr Leu Asn Asp Ser Ala
            370                 375                 380
Val Gln Glu Asp Ser Tyr Gly Leu Ile Thr Thr Thr Arg Ala Thr Ile
385                 390                 395                 400
Asn Pro Gly Val Asp Gly Thr Asn Arg Ile Glu Ser Thr Ala Val Asp
                405                 410                 415
Phe Arg Ser Ala Leu Ile Gly Ile Tyr Gly Val Asn Arg Ala Ser Phe
                420                 425                 430
Val Pro Gly Gly Leu Phe Asn Gly Thr Thr Ser Pro Ala Asn Gly Gly
                435                 440                 445
Cys Arg Asp Leu Tyr Asp Thr Asn Asp Glu Leu Pro Pro Asp Glu Ser
            450                 455                 460
Thr Gly Ser Ser Thr His Arg Leu Ser His Val Thr Phe Phe Ser Phe
465                 470                 475                 480
Gln Thr Asn Gln Ala Gly Ser Ile Ala Asn Ala Gly Ser Val Pro Thr
                485                 490                 495
Tyr Val Trp Thr Arg Arg Asp Val Asp Leu Asn Asn Thr Ile Thr Pro
                500                 505                 510
Asn Arg Ile Thr Gln Leu Pro Leu Val Lys Ala Ser Ala Pro Val Ser
                515                 520                 525
Gly Thr Thr Val Leu Lys Gly Pro Gly Phe Thr Gly Gly Ile Leu
                530                 535                 540
Arg Arg Thr Thr Asn Gly Thr Phe Gly Thr Leu Arg Val Thr Val Asn
545                 550                 555                 560
Ser Pro Leu Thr Gln Gln Tyr Arg Leu Arg Val Arg Phe Ala Ser Thr
                565                 570                 575
Gly Asn Phe Ser Ile Arg Leu Leu Arg Gly Gly Val Ser Ile Gly Asp
                580                 585                 590
Val Arg Leu Gly Ser Thr Met Asn Arg Gly Gln Glu Leu Thr Tyr Glu
            595                 600                 605
Ser Phe Phe Thr Arg Glu Phe Thr Thr Thr Gly Pro Phe Asn Pro Pro
            610                 615                 620
Phe Thr Phe Thr Gln Ala Gln Glu Ile Leu Thr Val Asn Ala Glu Gly
625                 630                 635                 640
Val Ser Thr Gly Gly Glu Tyr Tyr Ile Asp Arg Ile Glu Ile Val Pro
                645                 650                 655
Val Asn Pro Ala Arg Glu Ala Glu Glu Asp Leu Glu Ala Ala Lys Lys
                660                 665                 670
Ala Val Ala Ser Leu Phe Thr Arg Thr Arg Asp Gly Leu Gln Val Asn
            675                 680                 685
Val Thr Asp Tyr Gln Val Asp Arg Ala Ala Asn Leu Val Ser Cys Leu
            690                 695                 700
Ser Asp Glu Gln Tyr Ser His Asp Lys Lys Met Leu Leu Glu Ala Val
705                 710                 715                 720
Arg Ala Ala Lys Arg Leu Ser Arg Glu Arg Asn Leu Leu Gln Asp Pro
                725                 730                 735
Asp Phe Asn Thr Ile Asn Ser Thr Glu Glu Asn Gly Trp Lys Ala Ser
            740                 745                 750
```

-continued

Asn Gly Val Thr Ile Ser Glu Gly Gly Pro Phe Phe Lys Gly Arg Ala
        755                 760                 765

Leu Gln Leu Ala Ser Ala Arg Glu Asn Tyr Pro Thr Tyr Ile Tyr Gln
    770                 775                 780

Lys Val Asp Ala Ser Val Leu Lys Pro Tyr Thr Arg Tyr Arg Leu Asp
785                 790                 795                 800

Gly Phe Val Lys Ser Ser Gln Asp Leu Glu Ile Asp Leu Ile His His
                805                 810                 815

His Lys Val His Leu Val Lys Asn Val Pro Asp Asn Leu Val Ser Asp
            820                 825                 830

Thr Tyr Ser Asp Gly Ser Cys Ser Gly Ile Asn Arg Cys Asp Glu Gln
        835                 840                 845

Gln Gln Val Asp Met Gln Leu Asp Ala Glu His His Pro Met Asp Cys
    850                 855                 860

Cys Glu Ala Ala Gln Thr His Glu Phe Ser Ser Tyr Ile Asn Thr Gly
865                 870                 875                 880

Asp Leu Asn Ala Ser Val Asp Gln Gly Ile Trp Val Val Leu Lys Val
                885                 890                 895

Arg Thr Thr Asp Gly Tyr Ala Thr Leu Gly Asn Leu Glu Leu Val Glu
            900                 905                 910

Val Gly Pro Leu Ser Gly Glu Ser Leu Glu Arg Glu Gln Arg Asp Asn
        915                 920                 925

Ala Lys Trp Asn Ala Glu Leu Gly Arg Lys Arg Ala Glu Thr Asp Arg
    930                 935                 940

Val Tyr Leu Ala Ala Lys Gln Ala Ile Asn His Leu Phe Val Asp Tyr
945                 950                 955                 960

Gln Asp Gln Gln Leu Asn Pro Glu Ile Gly Leu Ala Glu Ile Asn Glu
                965                 970                 975

Ala Ser Asn Leu Val Lys Ser Ile Ser Gly Val Tyr Ser Asp Thr Leu
            980                 985                 990

Leu Gln Ile Pro Gly Ile Asn Tyr Glu Ile Tyr Thr Glu Leu Ser Asp
        995                 1000                1005

Arg Leu Gln Gln Ala Ser Tyr Leu Tyr Thr Ser Arg Asn Ala Val
    1010                1015                1020

Gln Asn Gly Asp Phe Asn Ser Gly Leu Asp Ser Trp Asn Ala Thr
    1025                1030                1035

Thr Asp Ala Ser Val Gln Gln Asp Gly Ser Thr His Phe Leu Val
    1040                1045                1050

Leu Ser His Trp Asp Ala Gln Val Ser Gln Gln Met Arg Val Asn
    1055                1060                1065

Leu Asn Cys Lys Tyr Val Leu Arg Val Thr Ala Lys Lys Val Gly
    1070                1075                1080

Gly Gly Asp Gly Tyr Val Thr Ile Arg Asp Gly Ala His His Gln
    1085                1090                1095

Glu Thr Leu Thr Phe Asn Ala Cys Asp Tyr Asp Val Asn Gly Thr
    1100                1105                1110

Tyr Val Asn Asp Asn Ser Tyr Ile Thr Lys Glu Val Val Phe Tyr
    1115                1120                1125

Pro Glu Thr Lys His Met Trp Val Glu Val Ser Glu Ser Glu Gly
    1130                1135                1140

Ser Phe Tyr Ile Asp Ser Ile Glu Phe Ile Glu Thr Gln Glu
    1145                1150                1155

<210> SEQ ID NO 19
<211> LENGTH: 1173
<212> TYPE: PRT
<213> ORGANISM: Artificial Sequence
<220> FEATURE:
<223> OTHER INFORMATION: Mutant BT-0068

<400> SEQUENCE: 19

Met Asn Arg Asn Asn Gln Gly Glu Tyr Glu Ile Ile Asp Ala Ser Thr
1               5                   10                  15

Cys Gly Cys Ser Ser Asp Asp Val Val Gln Tyr Pro Leu Ala Arg Asp
            20                  25                  30

Pro Asn Ala Ala Phe Gln Asn Met Asn Tyr Lys Asp Tyr Leu Lys Met
        35                  40                  45

Ser Asp Gly Asp Tyr Val Asp Ser Tyr Ile Asn Pro Gly Leu Ser Ile
    50                  55                  60

Gly Arg Arg Asp Val Thr Leu Thr Gly Val Gly Ile Val Ala Leu Ile
65                  70                  75                  80

Val Gly Thr Leu Gly Gly Pro Val Gly Gly Ile Val Thr Gly Leu Ile
                85                  90                  95

Ser Ser Leu Leu Gly Leu Leu Trp Pro Ser Asn Asp Asn Asp Val Trp
            100                 105                 110

Glu Ala Phe Met Ala Gln Ile Glu Glu Leu Ile Glu Gln Arg Ile Ala
        115                 120                 125

Asp Gln Val Val Arg Asn Ala Leu Asp Asn Leu Thr Gly Leu Arg Asp
    130                 135                 140

Tyr Tyr Asn Gln Tyr Leu Leu Ala Leu Glu Glu Trp Gln Glu Arg Pro
145                 150                 155                 160

Asn Ala Val Arg Ser Thr Leu Val Phe Asn Arg Phe Glu Thr Leu His
                165                 170                 175

Ser His Phe Val Thr Ser Met Pro Ser Phe Gly Ser Gly Pro Gly Ser
            180                 185                 190

Glu Arg Tyr Ala Val Gln Leu Leu Thr Val Tyr Ala Gln Ala Ala Asn
        195                 200                 205

Leu His Leu Leu Leu Leu Arg Asp Ala Asp Ile Tyr Gly Ala Arg Trp
    210                 215                 220

Gly Leu Arg Glu Ser Gln Ile Asp Leu Tyr Phe Asn Glu Leu Gln Asn
225                 230                 235                 240

Arg Thr Arg Asp Tyr Thr Asn His Cys Val Thr Ala Tyr Asn Asn Gly
                245                 250                 255

Leu Glu Glu Ile Arg Gly Thr Ser Pro Ala Ser Trp Leu Arg Tyr His
            260                 265                 270

Gln Phe Arg Arg Glu Thr Thr Leu Ile Ala Leu Asp Leu Val Ala Ile
        275                 280                 285

Phe Pro Tyr Tyr Asn Val Arg Glu Tyr Pro Ile Gly Val Asn Pro Gln
    290                 295                 300

Leu Thr Arg Asp Val Tyr Thr Asp Pro Ile Gly Val Thr Phe Arg Arg
305                 310                 315                 320

Glu Asp Trp Glu Thr Gly Val Glu Cys Arg Pro Trp Val Asn Thr Pro
                325                 330                 335

Tyr Met Ser Phe Ser Asp Leu Glu Asn Ala Ile Ile Arg Pro Pro His
            340                 345                 350

Leu Phe Glu Thr Leu Arg Asn Leu Thr Ile His Thr Gly Arg Tyr Asn
        355                 360                 365

```
Leu Val Gly Gly Ala Arg Phe Ile Glu Gly Trp Val Gly His Ser Val
    370                 375                 380
Thr Asn Thr Arg Leu Gly Asn Ser Thr Val Phe Thr Ser Asn Tyr Gly
385                 390                 395                 400
Ser Leu Pro Pro Arg Phe Gln Val Phe Asn Phe Thr Asn Phe Asp Val
                405                 410                 415
Tyr Gln Ile Asn Thr Arg Ala Asp Ser Thr Gly Thr Phe Arg Ile Pro
                420                 425                 430
Gly Phe Ala Val Thr Arg Ala Gln Phe Ile Pro Gly Gly Thr Tyr Ser
            435                 440                 445
Val Ala His Arg Asp Pro Gly Ala Cys Gln Gln Asp Tyr Asp Ser Ile
450                 455                 460
Glu Glu Leu Pro Ser Leu Asp Pro Asp Glu Pro Ile Asn Arg Ser Tyr
465                 470                 475                 480
Ser His Arg Leu Ser His Val Thr Leu Tyr Lys Tyr Thr Leu Ser Asp
                485                 490                 495
Thr Asp Tyr Gly Val Ile Asn Tyr Thr Asp Tyr Gly Ser Met Pro Ala
                500                 505                 510
Tyr Val Trp Thr His Arg Asp Val Asp Leu Thr Asn Thr Ile Thr Ala
            515                 520                 525
Asp Arg Ile Thr Gln Leu Pro Leu Val Lys Ala Ser Thr Leu Pro Ala
530                 535                 540
Gly Thr Thr Val Val Lys Gly Pro Gly Phe Thr Gly Gly Asp Ile Leu
545                 550                 555                 560
Arg Arg Thr Thr Asn Gly Thr Phe Gly Thr Leu His Val Arg Val Asn
                565                 570                 575
Ser Pro Leu Thr Gln Gln Tyr Arg Leu Arg Val Arg Phe Ala Ser Thr
                580                 585                 590
Gly Asn Phe Ser Ile Arg Val Leu Arg Gly Gly Thr Ser Ile Gly Asp
            595                 600                 605
Ala Arg Phe Gly Ser Thr Met Asn Arg Gly Gln Glu Leu Thr Tyr Glu
            610                 615                 620
Ser Phe Val Thr Arg Glu Phe Thr Thr Thr Gly Pro Phe Asn Pro Pro
625                 630                 635                 640
Phe Thr Phe Thr Gln Thr Gln Glu Ile Leu Thr Val Asn Ala Glu Gly
                645                 650                 655
Val Ser Thr Gly Gly Glu Tyr Tyr Ile Asp Ser Ile Glu Ile Val Pro
                660                 665                 670
Val Asn Pro Thr Arg Glu Ala Glu Asp Leu Glu Ala Ala Lys Lys
                675                 680                 685
Ala Val Ala Ser Leu Phe Thr Arg Thr Arg Asp Gly Leu Gln Val Asn
            690                 695                 700
Val Thr Asp Tyr Gln Val Asp Arg Ala Ala Asn Leu Val Leu Cys Leu
705                 710                 715                 720
Ser Asp Glu Gln Tyr Ala His Asp Lys Lys Met Leu Leu Glu Ala Val
                725                 730                 735
Arg Ala Ala Lys Arg Leu Ser Arg Glu Arg Asn Leu Leu Gln Asp Pro
                740                 745                 750
Asp Phe Asn Glu Ile Asn Ser Thr Glu Asp Ser Gly Trp Lys Thr Ser
                755                 760                 765
Asn Gly Ile Ile Ile Ser Glu Gly Gly Pro Phe Phe Lys Gly Arg Ala
            770                 775                 780
Leu Gln Leu Ala Ser Ala Arg Glu Asn Tyr Pro Thr Tyr Ile Tyr Gln
```

```
             785                 790                 795                 800
Lys Val Asp Ser Ser Met Leu Lys Pro Tyr Thr Arg Tyr Lys Leu Asp
                805                 810                 815
Gly Phe Val Gln Ser Ser Gln Asp Leu Glu Ile Glu Leu Ile His His
                820                 825                 830
His Lys Val His Leu Val Lys Asn Val Pro Asp Asn Leu Val Leu Asp
                835                 840                 845
Thr Tyr Pro Asp Gly Ser Cys Asn Gly Ile Asn Arg Cys Glu Glu Gln
        850                 855                 860
Gln Met Val Asn Ser Gln Leu Glu Thr Glu His His Pro Met Asp Cys
865                 870                 875                 880
Cys Glu Ala Ser Gln Thr His Glu Phe Ser Ser Tyr Ile His Thr Gly
                885                 890                 895
Asp Leu Asn Ala Ser Val Asp Gln Gly Ile Trp Val Val Leu Lys Ile
                900                 905                 910
Arg Thr Thr Asp Gly Ser Ala Thr Leu Gly Asn Leu Glu Leu Val Glu
        915                 920                 925
Val Gly Pro Leu Ser Gly Glu Ser Leu Glu Arg Glu Gln Arg Asp Asn
    930                 935                 940
Ala Lys Trp Asn Ala Glu Leu Gly Arg Lys Arg Ala Glu Ala Asp Arg
945                 950                 955                 960
Val Tyr Gln Gly Ala Lys Gln Ala Ile Asn His Leu Phe Val Asp Tyr
                965                 970                 975
Gln Asp Gln Gln Leu Asn Pro Glu Val Gly Leu Ala Glu Ile Ser Glu
            980                 985                 990
Ala Arg Asn Leu Ile Glu Ser Ile  Ser Asp Val Tyr Cys  Asp Ala Val
        995                 1000                1005
Leu Arg Ile Pro Gly Ile Asn Tyr Glu Met Tyr Thr  Glu Leu Ser
    1010                1015                1020
Asn Arg Leu Gln Gln Ala Ala Tyr Leu Tyr Thr Ser  Arg Asn Ala
    1025                1030                1035
Val Gln Asn Gly Asp Phe Asn Ser Gly Leu Asp Ser  Trp Asn Ala
    1040                1045                1050
Thr Thr Asp Ala Thr Val Gln Gln Asp Gly Asn Met  Tyr Phe Leu
    1055                1060                1065
Val Leu Ser His Trp Asp Ala Gln Val Ser Gln Gln Phe Arg Val
    1070                1075                1080
Gln Pro Asn Cys Lys Tyr Val Leu Arg Val Thr Ala Lys Lys Val
    1085                1090                1095
Gly Asn Gly Asp Gly Tyr Val Thr Ile Gln Asp Gly Ala His His
    1100                1105                1110
Arg Glu Thr Leu Thr Phe Asn Ala Cys Asp Tyr Asp Val Asn Gly
    1115                1120                1125
Thr His Val Asn Asp Asn Ser Tyr Ile Thr Lys Glu Leu Glu Phe
    1130                1135                1140
Tyr Pro Lys Thr Glu His Met Trp Val Glu Val Ser Glu Thr Glu
    1145                1150                1155
Gly Thr Phe Tyr Ile Asp Ser Ile Glu Leu Ile Glu Thr Gln Glu
    1160                1165                1170

<210> SEQ ID NO 20
<211> LENGTH: 1179
<212> TYPE: PRT
<213> ORGANISM: Artificial Sequence
```

```
<220> FEATURE:
<223> OTHER INFORMATION: Mutant BT-0128

<400> SEQUENCE: 20

Met Gly Gly Lys Ser Met Asn Arg Asn Asn Gln Gly Glu Tyr Glu Ile
1               5                   10                  15

Ile Asp Ala Ser Thr Cys Gly Cys Ser Ser Asp Val Val Gln Tyr
            20                  25                  30

Pro Leu Ala Arg Asp Pro Asn Ala Ala Phe Gln Asn Met Asn Tyr Lys
            35                  40                  45

Asp Tyr Leu Lys Met Ser Asp Gly Asp Tyr Val Asp Ser Tyr Ile Asn
            50                  55                  60

Pro Gly Leu Ser Ile Gly Arg Arg Asp Val Thr Leu Thr Gly Val Gly
65                  70                  75                  80

Ile Val Ala Leu Ile Val Gly Thr Leu Gly Pro Val Gly Gly Ile
                85                  90                  95

Val Thr Gly Leu Ile Ser Ser Leu Leu Gly Leu Leu Trp Pro Ser Asn
                100                 105                 110

Asp Asn Asp Val Trp Glu Ala Phe Met Ala Gln Ile Glu Glu Leu Ile
            115                 120                 125

Glu Gln Arg Ile Ala Asp Gln Val Val Arg Asn Ala Leu Asp Asn Leu
            130                 135                 140

Thr Gly Leu Arg Asp Tyr Tyr Asn Gln Tyr Leu Leu Ala Leu Glu Glu
145                 150                 155                 160

Trp Gln Glu Arg Pro Asn Ala Val Arg Ser Thr Leu Val Phe Asn Arg
                165                 170                 175

Phe Glu Thr Leu His Ser His Phe Val Thr Ser Met Pro Ser Phe Gly
                180                 185                 190

Ser Gly Pro Gly Ser Glu Arg Tyr Ala Val Gln Leu Leu Thr Val Tyr
            195                 200                 205

Ala Gln Ala Ala Asn Leu His Leu Leu Leu Arg Asp Ala Asp Ile
            210                 215                 220

Tyr Gly Ala Arg Trp Gly Leu Arg Glu Ser Gln Ile Asp Leu Tyr Phe
225                 230                 235                 240

Asn Glu Leu Gln Asn Arg Thr Arg Asp Tyr Thr Asn His Cys Val Thr
                245                 250                 255

Ala Tyr Asn Asn Gly Leu Glu Glu Ile Arg Gly Thr Ser Pro Ala Ser
            260                 265                 270

Trp Leu Arg Tyr His Gln Phe Arg Arg Glu Thr Thr Leu Ile Ala Leu
            275                 280                 285

Asp Leu Val Ala Ile Phe Pro Tyr Tyr Asn Val Arg Glu Tyr Pro Ile
            290                 295                 300

Gly Val Asn Pro Gln Leu Thr Arg Asp Val Tyr Thr Asp Pro Ile Gly
305                 310                 315                 320

Val Thr Phe Arg Arg Glu Asp Trp Glu Thr Gly Val Glu Cys Arg Pro
                325                 330                 335

Trp Val Asn Thr Pro Tyr Met Ser Phe Ser Asp Leu Glu Asn Ala Ile
                340                 345                 350

Ile Arg Pro Pro His Leu Phe Glu Thr Leu Arg Asn Leu Thr Ile His
            355                 360                 365

Thr Gly Arg Tyr Asn Leu Val Gly Gly Ala Arg Phe Ile Glu Gly Trp
370                 375                 380

Val Gly His Ser Val Thr Asn Thr Arg Leu Gly Asn Ser Thr Val Phe
385                 390                 395                 400
```

-continued

Thr Ser Asn Tyr Gly Ser Leu Pro Pro Arg Phe Gln Val Phe Asn Phe
                    405                 410                 415
Thr Asn Phe Asp Val Tyr Gln Ile Asn Thr Arg Ala Asp Ser Thr Gly
                420                 425                 430
Thr Phe Arg Ile Pro Gly Phe Ala Val Thr Arg Ala Gln Phe Ile Pro
            435                 440                 445
Gly Gly Thr Tyr Ser Val Ala His Arg Asp Pro Gly Ala Cys Gln Gln
        450                 455                 460
Asp Tyr Asp Ser Ile Glu Glu Leu Pro Ser Leu Asp Pro Asp Glu Pro
465                 470                 475                 480
Ile Asn Arg Ser Tyr Ser His Arg Leu Ser His Val Thr Leu Tyr Lys
                485                 490                 495
Tyr Thr Leu Ser Asp Thr Asp Tyr Gly Val Ile Asn Tyr Thr Asp Tyr
                500                 505                 510
Gly Ser Met Pro Ala Tyr Val Trp Thr His Arg Asp Val Asp Leu Thr
            515                 520                 525
Asn Thr Ile Thr Ala Asp Arg Ile Thr Gln Leu Pro Leu Val Lys Ala
        530                 535                 540
Ser Thr Leu Pro Ala Gly Thr Val Val Lys Gly Pro Gly Phe Thr
545                 550                 555                 560
Gly Gly Asp Ile Leu Arg Arg Thr Thr Asn Gly Thr Phe Gly Thr Leu
                565                 570                 575
His Val Arg Val Asn Ser Pro Leu Thr Gln Gln Tyr Arg Leu Arg Val
                580                 585                 590
Arg Phe Ala Ser Thr Gly Asn Phe Ser Ile Arg Val Leu Arg Gly Gly
                595                 600                 605
Thr Ser Ile Gly Asp Ala Arg Phe Gly Ser Thr Met Asn Arg Gly Gln
            610                 615                 620
Glu Leu Thr Tyr Glu Ser Phe Val Thr Arg Glu Phe Thr Thr Thr Gly
625                 630                 635                 640
Pro Phe Asn Pro Pro Phe Thr Phe Thr Gln Thr Gln Glu Ile Leu Thr
                645                 650                 655
Val Asn Ala Glu Gly Val Ser Thr Gly Gly Glu Tyr Tyr Ile Asp Ser
                660                 665                 670
Ile Glu Ile Val Pro Val Asn Pro Thr Arg Glu Ala Glu Glu Asp Leu
            675                 680                 685
Glu Ala Ala Lys Lys Ala Val Ala Ser Leu Phe Thr Arg Thr Arg Asp
        690                 695                 700
Gly Leu Gln Val Asn Val Thr Asp Tyr Gln Val Asp Gln Ala Ala Asn
705                 710                 715                 720
Leu Val Ser Cys Leu Ser Asp Glu Gln Tyr Gly Tyr Asp Lys Lys Met
                725                 730                 735
Leu Leu Glu Ala Val Arg Ala Ala Lys Arg Leu Ser Arg Glu Arg Asn
                740                 745                 750
Leu Leu Gln Asp Pro Asp Phe Asn Thr Ile Asn Ser Thr Glu Glu Asn
            755                 760                 765
Gly Trp Lys Ala Ser Asn Gly Val Thr Ile Ser Glu Gly Gly Pro Phe
        770                 775                 780
Tyr Lys Gly Arg Ala Leu Gln Leu Ala Ser Ala Arg Glu Asn Tyr Pro
785                 790                 795                 800
Thr Tyr Ile Tyr Gln Lys Val Asp Ala Ser Glu Leu Lys Pro Tyr Thr
                805                 810                 815

-continued

```
Arg Tyr Arg Leu Asp Gly Phe Val Lys Ser Ser Gln Asp Leu Glu Ile
            820                 825                 830

Asp Leu Ile His His His Lys Val His Leu Val Lys Asn Val Pro Asp
        835                 840                 845

Asn Leu Val Ser Asp Thr Tyr Pro Asp Asp Ser Cys Ser Gly Ile Asn
    850                 855                 860

Arg Cys Gln Glu Gln Gln Met Val Asn Ala Gln Leu Glu Thr Glu His
865                 870                 875                 880

His His Pro Met Asp Cys Cys Glu Ala Ala Gln Thr His Glu Phe Ser
                885                 890                 895

Ser Tyr Ile Asp Thr Gly Asp Leu Asn Ser Ser Val Asp Gln Gly Ile
            900                 905                 910

Trp Ala Ile Phe Lys Val Arg Thr Thr Asp Gly Tyr Ala Thr Leu Gly
        915                 920                 925

Asn Leu Glu Leu Val Glu Val Gly Pro Leu Ser Gly Glu Ser Leu Glu
    930                 935                 940

Arg Glu Gln Arg Asp Asn Thr Lys Trp Ser Ala Glu Leu Gly Arg Lys
945                 950                 955                 960

Arg Ala Glu Thr Asp Arg Val Tyr Gln Asp Ala Lys Gln Ser Ile Asn
                965                 970                 975

His Leu Phe Val Asp Tyr Gln Asp Gln Gln Leu Asn Pro Glu Ile Gly
            980                 985                 990

Met Ala Asp Ile Met Asp Ala Gln  Asn Leu Val Ala Ser  Ile Ser Asp
        995                 1000                 1005

Val Tyr Ser Asp Ala Val Leu  Gln Ile Pro Gly Ile  Asn Tyr Glu
    1010                1015                 1020

Ile Tyr  Thr Glu Leu Ser Asn  Arg Leu Gln Gln Ala  Ser Tyr Leu
    1025                1030                 1035

Tyr Thr  Ser Arg Asn Ala Val  Gln Asn Gly Asp Phe  Asn Asn Gly
    1040                1045                 1050

Leu Asp  Ser Trp Asn Ala Thr  Ala Gly Ala Ser Val  Gln Gln Asp
    1055                1060                 1065

Gly Asn  Thr His Phe Leu Val  Leu Ser His Trp Asp  Ala Gln Val
    1070                1075                 1080

Ser Gln  Gln Phe Arg Val Gln  Pro Asn Cys Lys Tyr  Val Leu Arg
    1085                1090                 1095

Val Thr  Ala Glu Lys Val Gly  Gly Gly Asp Gly Tyr  Val Thr Ile
    1100                1105                 1110

Arg Asp  Gly Ala His His Thr  Glu Thr Leu Thr Phe  Asn Ala Cys
    1115                1120                 1125

Asp Tyr  Asp Ile Asn Gly Thr  Tyr Val Thr Asp Asn  Thr Tyr Leu
    1130                1135                 1140

Thr Lys  Glu Val Ile Phe Tyr  Ser His Thr Glu His  Met Trp Val
    1145                1150                 1155

Glu Val  Asn Glu Thr Glu Gly  Ala Phe His Leu Asp  Ser Leu Glu
    1160                1165                 1170

Phe Val  Glu Thr Glu Lys
    1175

<210> SEQ ID NO 21
<211> LENGTH: 26
<212> TYPE: DNA
<213> ORGANISM: Artificial Sequence
<220> FEATURE:
<223> OTHER INFORMATION: OAR2613a Forward Primer
```

```
<400> SEQUENCE: 21
aaacatgaac cgaaataatc aaaatg                                         26

<210> SEQ ID NO 22
<211> LENGTH: 22
<212> TYPE: DNA
<213> ORGANISM: Artificial Sequence
<220> FEATURE:
<223> OTHER INFORMATION: OAR2615a Reverse Primer

<400> SEQUENCE: 22
atccgtccct tgtgcgtgta aa                                             22

<210> SEQ ID NO 23
<211> LENGTH: 30
<212> TYPE: DNA
<213> ORGANISM: Artificial Sequence
<220> FEATURE:
<223> OTHER INFORMATION: OAR2611a-F forward primer

<400> SEQUENCE: 23
gtttaaacat gaatcgaaat aatcaaaatg                                     30

<210> SEQ ID NO 24
<211> LENGTH: 29
<212> TYPE: DNA
<213> ORGANISM: Artificial Sequence
<220> FEATURE:
<223> OTHER INFORMATION: OAR2612a-R reverse primer

<400> SEQUENCE: 24
ggcgcgccct actcttgtgt ttcaataaa                                      29

<210> SEQ ID NO 25
<211> LENGTH: 29
<212> TYPE: DNA
<213> ORGANISM: Artificial Sequence
<220> FEATURE:
<223> OTHER INFORMATION: OAR2768-F forward primer

<400> SEQUENCE: 25
gtttaaacat gaatcaaaat aaacacgga                                      29

<210> SEQ ID NO 26
<211> LENGTH: 31
<212> TYPE: DNA
<213> ORGANISM: Artificial Sequence
<220> FEATURE:
<223> OTHER INFORMATION: OAR2769-R reverse primer

<400> SEQUENCE: 26
ggcgcgcctt actgttgggt ttccatgaac t                                   31
```

COMPOSITIONS AND METHODS FOR CONTOLLING PLANT PESTS

RELATED APPLICATION INFORMATION

This application is a divisional of co-pending U.S. application Ser. No. 15/534,074, filed Jun. 8, 2017, which is a 371 of International Application No. PCT/US2015/63610, filed Dec. 3, 2015, which claims priority to U.S. Provisional Application No. 62/090,899, filed Dec. 12, 2014, all of which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "80668-US-REG-ORG-D-1_SeqList.txt", created on Dec. 5, 2014, and having a size of 135 kilobytes and is filed concurrently with the specification. The sequence listing contained in this ASCII formatted document is part of the specification and is herein incorporated by reference in its entirety.

FIELD OF THE INVENTION

This invention relates to pesticidal proteins and the nucleic acid molecules that encode them, as well as compositions and methods for controlling plant pests.

BACKGROUND

*Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions comprising *Bacillus thuringiensis* strains or their insecticidal proteins can be used as environmentally-acceptable insecticides to control agricultural insect pests or insect vectors of a variety of human or animal diseases.

Crystal (Cry) proteins from *Bacillus thuringiensis* have potent insecticidal activity against predominantly lepidopteran, dipteran, and coleopteran larvae. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus Thuringiensis* family tree. In Advanced Engineered Pesticides. Marcel Dekker, Inc., New York, N.Y.). These proteins were originally classified as CryI to CryVI based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as CryIA, CryIB, CryIC, etc. Even more closely related proteins within each division were given names such as CryIC(a), CryIC(b), etc. The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each toxin is assigned a unique name incorporating a primary rank (an Arabic number), a secondary rank (an uppercase letter), a tertiary rank (a lowercase letter), and a quaternary rank (another Arabic number). In the current classification, Roman numerals have been exchanged for Arabic numerals in the primary rank. For example, "CryIA(a)" under the older nomenclature is now "Cry1Aa" under the current nomenclature.

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for lepidopteran-active Cry proteins and 60-80 kDa for coleopteran-active Cry proteins. Protoxins are converted into mature toxic fragments (approximately 60-70 kDa N terminal region) by gut proteases in the target pest. Many of these proteins are quite toxic to specific target insects, but harmless to plants and other non-targeted organisms.

Cry proteins generally have five conserved sequence domains, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain III typically consists of two antiparallel beta-sheets in 'jelly-roll' formation (de Maagd et al., 2001, supra). Domains II and III are involved in receptor recognition and binding, and are therefore considered determinants of toxin specificity.

Numerous commercially valuable plants, including common agricultural crops, are susceptible to attack by plant pests including insect and nematode pests, causing substantial reductions in crop yield and quality. For example, plant pests are a major factor in the loss of the world's important agricultural crops. About $8 billion are lost every year in the United States alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or compliment to chemical pesticides. The genes coding for some of these Cry proteins have been isolated and their expression in heterologous hosts such as transgenic plants have been shown to provide another tool for the control of economically important insect pests.

Good insect control can thus be reached, but certain chemicals can sometimes also affect non-target beneficial insects and certain biologicals have a very narrow spectrum of activity. In addition, the continued use of certain chemical and biological control methods heightens the chance for insect pests to develop resistance to such control measures. This has been partially alleviated by various resistance management practices, but there remains a need to discover new and effective pest control agents that provide an economic benefit to farmers and that are environmentally acceptable. Particularly needed are control agents that are targeted to a wider spectrum of economically important insect pests and that efficiently control insect strains that are or could become resistant to existing insect control agents.

SUMMARY

In view of these needs, it is an object of the present invention to provide new pest control agents by providing novel genes and pesticidal proteins that may be used to control a variety of plant pests.

The invention provides compositions and methods for conferring pesticidal activity to bacteria, plants, plant cells, tissues and seeds. In particular, chimeric genes comprising novel polynucleotides that encode Cry proteins isolated from *Bacillus thuringiensis* (Bt) and sequences substantially identical thereto, whose expression results in proteins with toxicity to economically important insect pests, particularly insect pests that infest plants, are provided. The invention is further drawn to the novel Cry proteins resulting from the expression of the nucleic acid sequences, and to compositions and formulations containing the Cry proteins, which are toxic to insects by inhibiting the ability of insect pests to survive, grow and reproduce, or of limiting insect-related damage or loss to crop plants. Cry proteins of the invention include native Cry proteins and mutant Cry proteins that have one or more amino acid substitutions, additions or deletions. Examples of mutant Cry proteins includes without limitation those that are mutated to have a broader spectrum of activity than their native Cry protein counterparts or those mutated to introduce an epitope to generate antibodies that differentially recognize the mutated protein from the native protein. The novel Cry proteins of the invention are highly active against insect pests. For example, the Cry proteins of the invention can be used to control one or more economically important insects pests such as black cutworm (*Agrotis ipsilon*), European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia fumacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and the like.

The invention also provides synthetic polynucleotides that encode the Cry proteins of the invention and have one or more codons optimized for expression in transgenic organisms such as bacteria and plants.

The invention is further drawn to expression cassettes and recombinant vectors comprising a polynucleotide that encodes a Cry protein of the invention. The invention also provides transformed bacteria, plants, plant cells, tissues, and seeds comprising a chimeric gene, or an expression cassette or a recombinant vector which comprise a polynucleotide encoding a Cry protein of the invention.

The invention is also drawn to methods of using the polynucleotides, for example in DNA constructs or chimeric genes or expression cassettes or recombinant vectors for transformation and expression in organisms, including microorganisms and plants. The nucleotide or amino acid sequences may be synthetic sequences that have been designed for expression in an organism including, but not limited to, a microorganism or a plant or in making hybrid toxins with enhanced pesticidal activity. The invention is further drawn to methods of making the Cry proteins and to methods of using the nucleic acid sequences, for example in microorganisms to control insects or in transgenic plants to confer protection from insect damage, and to methods of using the Cry proteins, and compositions and formulations comprising the Cry proteins, for example applying the Cry proteins or compositions or formulations to insect-infested areas, or to prophylactically treat insect-susceptible areas or plants to confer protection against the insect pests. The nucleotide or amino acid sequences may be synthetic sequences that have been designed for expression in an organism including, but not limited to, a microorganism or a plant.

The compositions and methods of the invention are useful for the production of organisms that are toxic to insects, specifically bacteria and plants. These organisms and compositions derived from them are desirable for agricultural purposes. The compositions of the invention are also useful for generating altered or improved Cry proteins that have pesticidal activity, or for detecting the presence of Cry protein or nucleic acids in products or organisms.

These and other features, aspects, and advantages of the invention will become better understood with reference to the following detailed description and claims.

BRIEF DESCRIPTION OF THE SEQUENCES IN THE SEQUENCE LISTING

SEQ ID NO: 1 represents a nucleotide sequence encoding a BT-0044 protein.

SEQ ID NO: 2 represents a nucleotide sequence encoding a BT-0051 protein.

SEQ ID NO: 3 represents a nucleotide sequence encoding a BT-0068 protein.

SEQ ID NO: 4 represents a nucleotide sequence encoding a BT-0128 protein.

SEQ ID NO: 5 represents a codon optimized sequence encoding a BT-0044 protein.

SEQ ID NO: 6 represents a codon optimized sequence encoding a BT-0051 protein.

SEQ ID NO:7 represents a codon optimized sequence encoding a BT-0068 protein.

SEQ ID NO:8 represents a codon optimized sequence encoding a BT-0128 protein.

SEQ ID NO:9 represents a nucleotide sequence encoding a mutant BT-0044 protein.

SEQ ID NO:10 represents a nucleotide sequence encoding a mutant BT-0051 protein.

SEQ ID NO:11 represents a nucleotide sequence encoding a mutant BT-0068 protein.

SEQ ID NO:12 represents a nucleotide sequence encoding a mutant BT-0128 protein.

SEQ ID NO:13 represents an amino acid sequence of a BT-0044 protein.

SEQ ID NO:14 represents an amino acid sequence of a BT-0051 protein.

SEQ ID NO:15 represents an amino acid sequence of a BT-0068 protein.

SEQ ID NO:16 represents an amino acid sequence of a BT-0128 protein.

SEQ ID NO:17 represents an amino acid sequence of a mutant BT-0044 protein.

SEQ ID NO:18 represents an amino acid sequence of a mutant BT-0051 protein.

SEQ ID NO:19 represents an amino acid sequence of a mutant BT-0068 protein.

SEQ ID NO:20 represents an amino acid sequence of a mutant BT-0128 protein.

SEQ ID NOS:21-26 represent primers useful in the invention.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. It is also to be understood that the terminology used herein is for the purpose of describing particular embodiments only, and is not intended to limit the scope of the present invention.

Definitions

As used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

By "activity" of a toxic Cry protein of the invention is meant that the toxic protein functions as an orally active insect control agent, has a toxic effect, or is able to disrupt or deter insect feeding, which may or may not cause death of the insect. When a toxic protein of the invention is delivered to the insect, the result is typically death of the insect, or the insect does not feed upon the source that makes the toxic protein available to the insect.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

To "control" insects means to inhibit, through a toxic effect, the ability of insect pests to survive, grow, feed, and/or reproduce, or to limit insect-related damage or loss in crop plants or to protect the yield potential of a crop when grown in the presence of insect pests. To "control" insects may or may not mean killing the insects, although it preferably means killing the insects.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of variant Cry proteins are aligned with each other, the amino acids that "correspond to" certain enumerated positions in the variant or homolog protein are those that align with these positions in a reference protein but that are not necessarily in these exact numerical positions relative to the particular reference amino acid sequence of the invention. For example, if SEQ ID NO:13 is the reference sequence and is aligned with SEQ ID NO:15, the Asn4 of SEQ ID NO:15 "corresponds to" Asn6 of SEQ ID NO:13.

To "deliver" a composition or toxic protein means that the composition or toxic protein comes in contact with an insect, resulting in a toxic effect and control of the insect. The composition or toxic protein can be delivered in many recognized ways, e.g., orally by ingestion by the insect or by contact with the insect via transgenic plant expression, formulated protein composition(s), sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

"Effective insect-controlling amount" means that concentration of toxic protein that inhibits, through a toxic effect, the ability of insects to survive, grow, feed and/or reproduce, or to limit insect-related damage or loss in crop plants or protects the yield potential of a crop when grown in the presence of insect pests. "Effective insect-controlling amount" may or may not mean killing the insects, although it preferably means killing the insects.

"Expression cassette" as used herein means a nucleic acid molecule capable of directing expression of at least one polynucleotide of interest in an appropriate host cell, comprising a promoter operably linked to the polynucleotide of interest which is operably linked to a termination signal. An "expression cassette" also typically comprises additional polynucleotides required for proper translation of the polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit consisting of a polynucleotide that occupies a specific location on a chromosome or plasmid and that contains the genetic instruction for a particular characteristic or trait in an organism.

A "gut protease" is a protease naturally found in the digestive tract of an insect. This protease is usually involved in the digestion of ingested proteins.

The term "heterologous" when used in reference to a gene or nucleic acid refers to a gene encoding a factor that is not in its natural environment (i.e., has been altered by the hand of man). For example, a heterologous gene may include a gene from one species introduced into another species. A heterologous gene may also include a gene native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Homologous recombination" is the exchange ("crossing over") of DNA fragments between two DNA molecules or chromatids of paired chromosomes in a region of identical polynucleotides. A "recombination event" is herein understood to mean a meiotic crossing-over.

A nucleic acid sequence is "isocoding" with a reference nucleic acid sequence when the nucleic acid sequence encodes a polypeptide having the same amino acid sequence as the polypeptide encoded by the reference nucleic acid sequence.

The term "isolated" nucleic acid molecule, polynucleotide or toxin is a nucleic acid molecule, polynucleotide or toxic protein that no longer exists in its natural environment. An isolated nucleic acid molecule, polynucleotide or toxin of the invention may exist in a purified form or may exist in a recombinant host such as in a transgenic bacterial cell or a transgenic plant.

A "nucleic acid molecule" is single- or double-stranded DNA or RNA that can be isolated from any source. In the context of the present invention, the nucleic acid molecule is preferably a segment of DNA.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

As used herein "pesticidal," insecticidal," and the like, refer to the ability of a Cry protein of the invention to control a pest organism or an amount of a Cry protein that can control a pest organism as defined herein. Thus, a pesticidal Cry protein can kill or inhibit the ability of a pest organism (e.g., insect pest) to survive, grow, feed, and/or reproduce.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"Polynucleotide of interest" refers to any polynucleotide which, when transferred to an organism, e.g. a plant, confers upon the organism a desired characteristic such as antibiotic resistance, virus resistance, insect resistance, disease resistance, or resistance to other pests, herbicide tolerance, improved nutritional value, improved performance in an industrial process, production of commercially valuable enzymes or metabolites or altered reproductive capability.

The term "promoter" refers to a polynucleotide, usually upstream (5') of its coding polynucleotide, which controls the expression of the coding polynucleotide by providing the recognition for RNA polymerase and other factors required for proper transcription.

A "protoplast" is an isolated plant cell without a cell wall or with only parts of the cell wall.

As used herein, the term "recombinant" refers to a form of nucleic acid (e.g. DNA or RNA) and/or protein and/or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, and/or a nucleic acid molecule that is artificially synthesized and comprises a polynucleotide that deviates from the polynucleotide that would normally exist in nature, and/or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA and/or protein molecule in that organism. As used herein, a "recombinant plant" is a plant that would not normally exist in nature, is the result of human intervention, and contains a transgene and/or heterologous nucleic acid molecule incorporated into its genome. As a result of such genomic alteration, the recombinant plant is distinctly different from the related wild-type plant.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

The term "identical" or "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, Md. 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising bases and/or structural features that are not present in the natural sequence. For example, an artificial sequence encoding a Cry protein of the invention that resembles more closely the G+C content and the normal codon distribution of dicot and/or monocot plant genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; l), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

This invention provides compositions and methods for controlling harmful plant pests. Particularly, the invention relates to Cry proteins that are toxic to plant pests and to polynucleotides that comprise nucleotide sequences that encode the Cry proteins, and to the making and using of the polynucleotides and Cry proteins to control plant pests.

Accordingly, in some embodiments, a chimeric gene is provided that comprises a heterologous promoter operably linked to a polynucleotide comprising a nucleotide sequence that encodes a protein toxic to at least black cutworm (*Agrotis ipsilon*), wherein the nucleotide sequence (a) has at least 80% (e.g. 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:1-4; or (b) encodes a protein comprising an amino acid sequence that has at least 80% (e.g. 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:13-16; or (c) is a synthetic sequence of (a) or (b) that has codons optimized for expression in a transgenic organism.

In other embodiments, the heterologous promoter is a plant-expressible promoter. For example, without limitation, the plant-expressible promoter can be selected from the group consisting of ubiquitin, cmp, corn TrpA, bacteriophage T3 gene 9 5' UTR, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

In additional embodiments, the protein encoded by the chimeric gene is additionally toxic to one or more insect species selected from the group consisting of European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia fumacalis*), cotton bollworm (*Helicoverpa armigera*), striped stem borer (*Chilo suppressalis*), pink stem borer (*Sesamia calamistis*) and rice leaffolder (Cnaphalocrocis *medinalis*).

In further embodiments, the polynucleotide comprises a nucleotide sequence that has at least 80% to at least 99% sequence identity with SEQ ID NO:1, or has at least 80% to at least 99% sequence identity with SEQ ID NO:2, or has at least 80% to at least 99% sequence identity with SEQ ID NO:3, or has at least 80% to at least 99% sequence identity with SEQ ID NO:4.

In other embodiments, the polynucleotide comprises a nucleotide sequence that encodes a protein comprising an amino acid sequence that has at least 80% to at least 99% sequence identity with any one of SEQ ID NOS:13-16.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:13.

In further embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:14.

In still further embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:15.

In other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:16.

In some embodiments, the chimeric gene of the invention comprises a poly nucleotide comprising a synthetic sequence of a nucleotide sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% with any of SEQ ID NOS:5-12, wherein the synthetic sequence has codons optimized for expression is a transgenic organism. In other embodiments, the chimeric gene of the invention comprises a nucleic acid molecule comprising a synthetic sequence of a nucleotide sequence that encodes a protein comprising an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any of SEQ ID NOS:13-20, wherein the synthetic sequence has codons optimized for expression is a transgenic organism. In further embodiments, the transgenic organism is a transgenic bacteria or a transgenic plant.

In some embodiments, the invention provides a synthetic polynucleotide comprising, consisting essentially of or consisting of a nucleotide sequence that encodes a protein that is active against at least black cutworm (*Agrotis ipsilon*), wherein the nucleotide sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:5-12.

In other embodiments, the invention provides a synthetic polynucleotide comprising, consisting essentially of or consisting of a nucleotide sequence that encodes a protein that is active against at least black cutworm (*Agrotis ipsilon*), wherein the nucleotide sequence encodes an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:13-20.

In some embodiments, the invention provides a synthetic polynucleotide comprising, consisting essentially of or consisting of a nucleotide sequence having at least one codon optimized for expression in a transgenic organism and encoding a protein toxic to at least black cutworm (*Agrotis ipsilon*) and corn earworm (*Helicoverpa zea*), wherein the protein comprises an amino acid sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity to SEQ ID NO:13 and the amino acid sequence at positions corresponding to amino acid positions 40-44 of SEQ ID NO:13 is NLNSC. In additional embodiments, the polynucleotide comprises, consists essentially of or consists of SEQ ID NO: 5 or SEQ ID NO:9. In further embodiments, the amino acid sequence comprises, consists essentially of or consists of SEQ ID NO:13 or SEQ ID NO:17.

According to some embodiments, the invention provides an isolated protein that is toxic to at least black cutworm (*Agrotis ipsilon*), wherein the protein comprises, consists essentially of or consists of (a) an amino acid sequence that has at least 80% sequence identity to at least 99% sequence identity with an amino acid sequence represented by any one of SEQ ID NOs:13-20 or (b) an amino acid sequence that is encoded by a nucleotide sequence that has at least 80% sequence identity to at least 99% sequence identity with a nucleotide sequence represented by any one of SEQ ID NOs:5-12.

In other embodiments, the isolated protein comprises, consists essentially of or consists of an amino acid sequence that has at least 80% to at least 99% sequence identity with any one of SEQ ID NOS:13-16. In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:13.

In other embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:14.

In further embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:15.

In still further embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:16.

In some embodiments, the amino acid sequence comprises, consists essentially of or consists of any one of SEQ ID NOs:13-20.

Antibodies raised in response to immune challenge by a native or mutant BT-0044, BT-0051, BT-0068 and BT-0128 and the like or related proteins of the present invention may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988) and as in Goding (1986). The present invention encompasses insecticidal proteins that cross-react with antibodies raised against one or more of the insecticidal Cry proteins of the present invention.

The antibodies produced in the present invention are also useful in immunoassays for determining the amount or presence of a native or mutant BT-0044, BT-0051, BT-0068 and BT-0128 or related protein in a biological sample. Such assays are also useful in quality-controlled production of compositions containing one or more of the toxic proteins of the present invention or related toxic proteins. In addition, the antibodies can be used to assess the efficacy of recombinant production of one or more of the proteins of the present invention or a related protein, as well as for screening expression libraries for the presence of a nucleotide sequence encoding one or more of the proteins of the invention or related protein coding sequences. Antibodies are useful also as affinity ligands for purifying and/or isolating any one or more of the proteins of the present invention and related proteins. The proteins of the present invention and proteins containing related antigenic epitopes may be obtained by over expressing full or partial lengths of a sequence encoding all or part of a protein of the present invention or a related protein in a preferred host cell.

It is recognized that DNA sequences that encode a native Cry protein of the invention may be altered by various methods, and that these alterations may result in DNA sequences encoding proteins with amino acid sequences different than that encoded by a native Cry protein of the invention. This protein may be altered in various ways including amino acid substitutions, deletions, truncations, and insertions of one or more amino acids of any of SEQ ID NOs:13-16, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a native Cry protein can be prepared by mutations in a polynucleotide that encodes the protein. This may also be accomplished by one of several forms of mutagenesis and/or in directed evolution. In some aspects, the changes encoded in the amino acid sequence will not substantially affect the function of the protein. Such variants will possess the desired insecticidal activity. In one embodiment of the invention, nucleotide sequences represented by SEQ ID NOs: 1-4 are altered to introduce amino acid substitutions in the encoded protein. In some embodiments, the resulting mutant protein is encoded by a synthetic mutant polynucleotide comprising a nucleotide sequence represented by any one of SEQ ID NOs:9-12. In other embodiments, the mutant proteins comprise, consist essentially of or consist of an amino acid sequence represented by any one of SEQ ID NOs:17-20.

It is understood that the ability of an insecticidal protein to confer insecticidal activity may be improved by the use of such techniques upon the compositions of this invention. For example, one may express a Cry protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the Cry protein mutations in a non-mutagenic strain, and identify mutated genes with insecticidal activity, for example by performing an assay to test for insecticidal activity. Generally, the protein is mixed and used in feeding assays. See, for example Marrone et al. (1985) J. of Economic Entomology 78:290-293. Such assays can include contacting plants with one or more pests and determining the plant's ability to survive and/or cause the death of the pests. Examples of mutations that result in increased toxicity are found in Schnepf et al. (1998) Microbiol. Mol. Biol. Rev. 62:775-806.

Alternatively, alterations may be made to an amino acid sequence of the invention at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

A Cry protein of the invention can also be mutated to introduce an epitope to generate antibodies that recognize the mutated protein. Therefore, in some embodiments, the invention provides a mutated Cry protein, wherein an amino acid substitution in a native Cry protein produces a mutant Cry protein having an antigenic region that allows the mutant Cry protein to be distinguished from the native Cry protein in a protein detection assay. In other embodiment, the invention provides a mutated Cry protein of the invention wherein the amino acid sequence comprises an amino acid substitution in a region corresponding to amino acids 342-354 of SEQ ID NO:6. In other embodiments, the amino acid sequence comprises an amino acid substitution at position 342, 343, 344, 345, 346, 347, 348, 349, 350, 351, 352, 353 or 354 of SEQ ID NO:6. In still other embodiments, the amino acid sequence comprises an amino acid substitution at an amino acid position corresponding to amino acids 350, 351 and 354 of SEQ ID NO:6. In further embodiments, the amino acid sequence comprises an amino acid substitution at amino acid positions 350, 351 and 354 of SEQ ID NO:6. In still further embodiments, the amino acid corresponding to position 350 is substituted with an isoleucine (I), the amino acid corresponding position 351 is substituted with a glutamine (Q) and the amino acid corresponding to position 354 is substituted with a serine (S). In other embodiments, the leucine (L) at position 350 of SEQ ID NO:6 is substituted with a isoleucine (I), the asparagine (N) at position 351 of SEQ ID NO:6 is substituted with a glutamine (Q) and the threonine (T) at position 354 of SEQ ID NO:6 is substituted with a serine (S). In other embodiments, the native Cry protein comprises an amino acid sequence represented by any one of SEQ ID NO:13-16. In still other embodiments, the native Cry protein comprises an amino acid sequence represented by SEQ ID NO:6 and the mutant protein comprises an amino acid sequence represented by SEQ ID NO:18.

In some embodiments, the invention provides an antibody that specifically recognizes an epitope of a mutant Cry protein of the invention, wherein the epitope comprises an amino acid sequence with one or more substitutions in the amino acids corresponding to amino acids 342-354 of SEQ ID NO:6. In other embodiments, the epitope comprises an amino acid sequence with one or more substitutions in amino acids 342-354 of SEQ ID NO:6. In still other embodiments, the epitope comprises amino acids 342-354 of SEQ ID NO:18.

In some embodiments, the invention provides a method of making an antibody that differentially recognizes a mutated Cry protein from the native Cry protein from which the mutated Cry protein is derived, the method comprising the steps of substituting amino acids in an antigenic loop of a native Cry protein and raising antibodies that specifically recognize the mutated antigenic loop in the mutated Cry protein and does not recognize the native Cry protein. In one embodiment, the antigenic loop is identified in non-conserved regions outside of domain I of the native Cry protein. In another embodiment, the antigenic loop is not a loop involved in the Cry protein's insect gut receptor recognition or involved in the protease activation of the Cry protein. In another embodiment, the antigenic loop comprises an amino acid sequence that corresponds to amino acids 341-354 of SEQ ID NO:6. In yet another embodiment, the antigenic loop comprises amino acids 342-354 of SEQ ID NO:6.

Variant nucleotide and amino acid sequences of the present invention also encompass sequences derived from mutagenic and recombinogenic procedures such as DNA shuffling. With such a procedure, one or more different toxic protein coding regions can be used to create a new toxic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

Domain swapping or shuffling is another mechanism for generating altered Cry proteins of the invention. Domains may be swapped between Cry proteins, resulting in hybrid or chimeric toxic proteins with improved pesticidal activity or target spectrum. Methods for generating recombinant proteins and testing them for pesticidal activity are well known in the art (see, for example, Naimov et al. (2001) Appl. Environ. Microbiol. 67:5328-5330; de Maagd et al. (1996) Appl. Environ. Microbiol. 62:1537-1543; Ge et al. (1991) J. Biol. Chem. 266:17954-17958; Schnepf et al. (1990) J. Biol. Chem. 265:20923-20930; Rang et al. 91999) Appl. Environ. Microbiol. 65:2918-2925).

In some embodiments, the invention provides a recombinant vector comprising a polynucleotide, a nucleic acid molecule, an expression cassette or a chimeric gene of the invention. In other embodiments, the vector is further defined as a plasmid, cosmid, phagemid, artificial chromosome, phage or viral vector. Certain vectors for use in transformation of plants and other organisms are known in the art.

Thus, some embodiments of the invention are directed to expression cassettes designed to express the polynucleotides and nucleic acid molecules of the invention. As used herein, "expression cassette" means a nucleic acid molecule having at least a control sequence operatively linked to a nucleotide sequence of interest. In this manner, for example, plant promoters operably linked to the nucleotide sequences to be expressed are provided in expression cassettes for expression in a plant, plant part and/or plant cell.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the invention, an expression cassette of this invention also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, termination signals, and polyadenylation signal sequences.

In some embodiments, an expression cassette of the invention also can include nucleotide sequences that encode other desired traits. Such nucleotide sequences can be stacked with any combination of nucleotide sequences to create plants, plant parts or plant cells having the desired phenotype. Stacked combinations can be created by any method including, but not limited to, cross breeding plants by any conventional methodology, or by genetic transformation (i.e. molecular stacking). If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

The expression cassette also can include a coding sequence for one or more polypeptides for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). It is recognized that the amount of production of pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) insecticidal proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants and/or plant parts into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In one embodiment, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) Appl. Microbiol. Biotechnol. 49:718).

In another embodiment, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like. In one embodiment, the α-amylase is the synthetic α-amylase, Amy797E, described is U.S. Pat. No. 8,093,453, herein incorporated by reference in its entirety.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

In some embodiments, the invention provides a transgenic non-human host cell comprising a polynucleotide, a nucleic acid molecule, a chimeric gene, an expression cassette or a recombinant vector of the invention. The transgenic non-human host cell can include, but is not limited to, a plant cell, a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc,* or *Alcaligenes*. Thus, for example, as biological insect control agents, the Cry proteins of the invention can be produced by expression of the chimeric gene encoding the Cry proteins of the invention in a bacterial cell. For example, in one embodiment, a *Bacillus thuringiensis* cell comprising a chimeric gene of the invention is provided.

In further embodiments, the invention provides a plant cell that is a dicot plant cell or a monocot plant cell. In additional embodiments, the dicot plant cell is selected from the group consisting of a soybean cell, sunflower cell, tomato cell, cole crop cell, cotton cell, sugar beet cell and tobacco cell. In further embodiments, the monocot cell is selected from the group consisting of a barley cell, maize cell, oat cell, rice cell, sorghum cell, sugar cane cell and wheat cell. In some embodiments, the invention provides a plurality of dicot cells or monocot cells expressing a toxic protein of the invention encoded by a chimeric gene of the invention. In other embodiments the plurality of cells are juxtaposed to form an apoplast and are grown in natural sunlight.

In another embodiment of the invention, a toxic protein of the invention is expressed in a higher organism, for example, a plant. In this case, transgenic plants expressing effective amounts of the toxic protein protect themselves from plant pests such as insect pests. When the insect starts feeding on such a transgenic plant, it also ingests the expressed toxin. This can deter the insect from further biting into the plant tissue or may even harm or kill the insect. A polynucleotide of the invention is inserted into an expression cassette, which is then stably integrated in the genome of the plant. In another embodiment, the polynucleotide is included in a non-pathogenic self-replicating virus. Plants transformed in accordance with the invention may be monocots or dicots and include, but are not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, *papaya*, mango, banana, and specialty plants, such as *Arabidopsis*, and woody plants such as coniferous and deciduous trees. Preferably, plants of the of the invention are crop plants such as maize, sorghum, wheat, sunflower, tomato, crucifers, peppers, potato, cotton, rice, soybean, sugar beet, sugarcane, tobacco, barley, oilseed rape, and the like.

Once a desired polynucleotide has been transformed into a particular plant species, it may be propagated in that species or moved into other varieties of the same species, particularly including commercial varieties, using traditional breeding techniques.

A polynucleotide of the invention is expressed in transgenic plants, thus causing the biosynthesis of the corresponding Cry protein in the transgenic plants. In this way, transgenic plants with enhanced yield protection in the presence of insect pressure are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, high expression in plants, for example corn plants, is best achieved from coding sequences that have at least about 35% GC content, or at least about 45%, or at least about 50%, or at least about 60%. Microbial nucleotide sequences that have low GC contents may express poorly in plants due to the existence of ATTTA motifs that may destabilize messages, and AATAAA motifs that may cause inappropriate polyadenylation. Although certain gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described for example in U.S. Pat. Nos. 5,625,136; 5,500,365 and 6,013,523.

In some embodiments, the invention provides synthetic genes made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are represented by any one of SEQ ID NOs: 13-20. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part synthetic optimized sequence.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

The novel cry protein coding sequences of the invention, either as their native sequence or as synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Examples of constitutive promoters useful in the invention include the CaMV 35S and 19S promoters (Fraley et al., U.S. Pat. No. 5,352,605, incorporated herein by reference). Additionally, a promoter is derived from any one of several of the actin genes, which are expressed in most cell types. The promoter expression cassettes described by McElroy et al. (Mol. Gen. Genet. 231: 150-160 (1991)) can be easily modified for the expression of the novel toxin gene and are particularly suitable for use in monocotyledonous hosts. Yet another constitutive promoter is derived from ubiquitin, which is another gene product known to accumulate in many cell types. A ubiquitin promoter has been cloned from several species for use in transgenic plants, for example, sunflower (Binet et al., 1991. Plant Science 79: 87-94), maize (Christensen et al., 1989. Plant Molec. Biol. 12: 619-632), and *arabidopsis* (Norris et al. 1993. Plant Molec. Biol. 21:895-906). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel cry protein coding sequences of the invention in plants, particularly maize, are those that direct expression in root, pith, leaf or pollen. Such promoters are disclosed in U.S. Pat. No. 5,625,136, herein incorporated by reference in its entirety. Other tissue specific promoters useful in the present invention include the cotton rubisco promoter disclosed in U.S. Pat. No. 6,040,504; the rice sucrose synthase promoter disclosed in U.S. Pat. No. 5,604,121; and the cestrum yellow leaf curling virus promoter disclosed in U.S. Pat. No. 7,166,770, all incorporated by reference in their entirety. Chemically inducible promoters useful for directing the expression of the novel toxin gene in plants are disclosed in U.S. Pat. No. 5,614,395 herein incorporated by reference in its entirety.

The nucleotide sequences of this invention can also be expressed under the regulation of promoters that are chemically regulated. This enables the Cry proteins of the invention to be synthesized only when the crop plants are treated with the inducing chemicals. Examples of such technology for chemical induction of gene expression is detailed in the published application EP 0 332 104 and U.S. Pat. No. 5,614,395. In one embodiment, the chemically regulated promoter is the tobacco PR-la promoter.

Another category of promoters useful in the invention is that which is wound inducible. Numerous promoters have been described which are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Non-limiting examples of promoters that cause tissue specific expression patterns that are useful in the invention include green tissue specific, root specific, stem specific, and/or flower specific. Promoters suitable for expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition to the selection of a suitable promoter, constructs for expression of an insecticidal toxin in plants require an appropriate transcription terminator to be operably linked downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adh1 and bronze1) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Plant Transformation

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., *Biotechnology* 4:1093-1096 (1986)). For both direct gene transfer and *Agrobacterium*-mediated transfer, transformation is usually (but not necessarily) undertaken with a selectable marker that may be a positive selection (Phosphomannose Isomerase), provide resistance to an antibiotic (kanamycin, hygromycin or methotrexate) or a herbicide (glyphosate or glufosinate). However, the choice of selectable marker is not critical to the invention.

Agrobacterium-mediated transformation is a commonly used method for transforming plants, in particular, dicot plants, because of its high efficiency of transformation and because of its broad utility with many different species. Agrobacterium-mediated transformation typically involves transfer of the binary vector carrying the foreign DNA of interest to an appropriate Agrobacterium strain that may depend on the complement of vir genes carried by the host Agrobacterium strain either on a co-resident Ti plasmid or chromosomally (Uknes et al. (1993) *Plant Cell* 5:159-169). The transfer of the recombinant binary vector to Agrobacterium can be accomplished by a triparental mating procedure using *Escherichia coli* carrying the recombinant binary vector, a helper *E. coli* strain that carries a plasmid that is able to mobilize the recombinant binary vector to the target Agrobacterium strain. Alternatively, the recombinant binary vector can be transferred to Agrobacterium by nucleic acid transformation (Hagen & Willmitzer (1988) *Nucleic Acids Res.* 16:9877).

Transformation of a plant by recombinant Agrobacterium usually involves co-cultivation of the Agrobacterium with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In another embodiment, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) *Proc. Natl. Acad. Sci. USA* 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin can be utilized as selectable markers for transformation (Svab, Z., Hajdukiewicz, P., and Maliga, P. (1990) *Proc. Natl. Acad. Sci. USA* 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells and/or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Further, as is well known in the art, intact transgenic plants can be regenerated from transformed plant cells, plant tissue culture and/or cultured protoplasts using any of a variety of known techniques. Plant regeneration from plant cells, plant tissue culture and/or cultured protoplasts is described, for example, in Evans et al. (*Handbook of Plant Cell Cultures, Vol.* 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)).

Additionally, the genetic properties engineered into the transgenic seeds and plants, plant parts, and/or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part and/or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotide is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Additional embodiments of the invention include harvested products produced from the transgenic plants and/or parts thereof of the invention, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention, wherein said seed or other plant part comprises a nucleic acid molecule/polynucleotide/nucleotide sequence of this invention.

In other embodiments, the invention provides an extract from a transgenic seed and/or a transgenic plant of the invention, wherein the extract comprises a nucleic acid molecule, a polynucleotide, a nucleotide sequence or a toxic protein of the invention. Extracts from plants or plant parts can be made according to procedures well known in the art (See, de la Torre et al., *Food, Agric. Environ.* 2(1):84-89 (2004); Guidet, *Nucleic Acids Res.* 22(9): 1772-1773 (1994); Lipton et al., *Food Agric. Immun.* 12:153-164 (2000)).

Insecticidal Compositions

In some embodiments, the invention provides an insecticidal composition comprising a Cry protein of the invention in an agriculturally acceptable carrier. As used herein an "agriculturally-acceptable carrier" can include natural or synthetic, organic or inorganic material which is combined with the active component to facilitate its application to the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. Another agriculturally acceptable carrier may be a transgenic plant or plant part.

In further embodiments, the insecticidal composition comprises a transgenic bacterial cell of the invention, wherein the bacterial cell comprises a chimeric gene of the invention. For example, such an insecticidal composition can be prepared by desiccation, lyophilization, homogenization, extraction, filtration, centrifugation, sedimentation, or concentration of a culture of *Bacillus thuringiensis* cells comprising a polynucleotide of the invention. In additional embodiments, the composition comprises from about 1% to about 99% by weight of the Cry protein of the invention.

The Cry proteins of the invention can be used in combination with other pest control agents to increase pest target range or for the prevention and/or management of insect resistance. Therefore, in some embodiments, the invention provides a composition that controls one or more plant pests, wherein the composition comprises a first Cry protein of the invention and a second pest control agent different from the first Cry protein. In other embodiments, the composition is a formulation for topical application to a plant. In still other embodiments, the composition is a transgenic plant. In further embodiments, the composition is a combination of a formulation topically applied to a transgenic plant. In one embodiment, the formulation comprises the first Cry protein of the invention when the transgenic plant comprises the second pest control agent. In another embodiment, the formulation comprises the second pest control agent when the transgenic plant comprises the first Cry protein of the invention.

In some embodiments, the second pest control agent can be an agent selected from the group consisting of a chemical pesticide, a *Bacillus thuringiensis* (Bt) insecticidal protein, a Xenorhabdus insecticidal protein, a *Photorhabdus* insecticidal protein, a *Brevibacillus laterosporus* insecticidal protein, a *Bacillus sphaericus* insecticidal protein, a protease inhibitors (both serine and cysteine types), lectins, alpha-amylase, peroxidase and cholesterol oxidase.

In other embodiments, the second pest control agent is a chemical pesticide selected from the group consisting of pyrethroids, carbamates, neonicotinoids, neuronal sodium channel blockers, insecticidal macrocyclic lactones, .gamma.-aminobutyric acid (GABA) antagonists, insecticidal ureas and juvenile hormone mimics. In another embodiment, the chemical pesticide is selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In another embodiment, the chemical pesticide is selected from the group consisting of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from the group consisting of Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa, Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa and Cry73Aa.

In further embodiments, the second pest control agent is a Vip3 vegetative insecticidal protein selected from the group consisting of Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2 and Vip3Bb3.

In still further embodiments, the first Cry protein of the invention and the second pest control agent are co-expressed in a transgenic plant. This co-expression of more than one pesticidal principle in the same transgenic plant can be achieved by genetically engineering a plant to contain and express all the genes necessary. Alternatively, a plant, Parent 1, can be genetically engineered for the expression of the Cry protein of the invention. A second plant, Parent 2, can be genetically engineered for the expression of the second pest control agent. By crossing Parent 1 with Parent 2, progeny plants are obtained which express all the genes introduced into Parents 1 and 2.

In additional embodiments, a method of producing a protein toxic to at least black cutworm (*Agrotis ipsilon*) is provided, the method comprising: culturing a transgenic non-human host cell that comprises polynucleotide or a chimeric gene or nucleic acid molecule or a recombinant vector of the invention under conditions in which the host produces a protein toxic to at least black cutworm (*Agrotis ipsilon*). In some embodiments, the transgenic non-human host cell is a plant cell. In one embodiment, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In other embodiments, the produced protein has insecticidal activity against at least one additional insect, wherein the additional insect is selected from the group consisting of European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) or rice leaffolder (Cnaphalocrocis *medinalis*), and any combination thereof.

In other embodiments, the chimeric gene comprises any of SEQ ID NOs:1-4. In still other embodiments, the produced protein comprises an amino acid sequence of any of SEQ ID NOs: 13-16.

In some embodiments, the chimeric gene comprises a nucleotide sequence that is codon optimized for expression in a plant. In other embodiments, the chimeric gene comprises any of SEQ ID NOs:5-12. In further embodiments, the produced protein comprises an amino acid sequence of any of SEQ ID NOs:13-20.

In further embodiments, the invention provides a method of producing a pest-resistant (e.g., an insect-resistant) transgenic plant, comprising: introducing into a plant a polynucleotide, a chimeric gene, a recombinant vector, an expression cassette or a nucleic acid molecule of the invention comprising a nucleotide sequence that encodes a Cry protein of the invention, wherein the nucleotide sequence is expressed in the plant, thereby conferring to the plant resistance to at least European corn borer, and producing a pest-resistant (e.g., an insect-resistant) transgenic plant. In some embodiments, a pest-resistant transgenic plant is resistant to at least black cutworm (*Agrotis ipsilon*) as compared to a control plant lacking the polynucleotide, chimeric gene, recombinant vector, expression cassette or nucleic acid molecule of the invention. In some embodiments, the introducing is achieved by transforming the plant. In other embodiments, the introducing is achieved by crossing a first plant comprising the chimeric gene, recombinant vector, expression cassette or nucleic acid molecule of the invention with a different second plant.

In some embodiments, a transgenic plant of the invention that is resistant to at least black cutworm (*Agrotis ipsilon*) is further resistant to at one additional insect, wherein the additional insect includes, but is not limited to, European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia* fumacalis), cotton bollworm (*Helicoverpa armigera*), striped stem borer (*Chilo suppressalis*), pink stem borer (*Sesamia calamistis*) or rice leaffolder (Cnaphalocrocis *medinalis*), and any combination thereof.

In further embodiments, a method of controlling at least black cutworm (*Agrotis ipsilon*) insects is provided, the method comprising delivering to the insects an effective amount of a Cry protein of the invention. To be effective, the Cry protein is first orally ingested by the insect. However, the Cry protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; (5) via injection into the insect; or (6) any other art-recognized protein delivery system. Thus, any method of oral delivery to an insect can be used to deliver the toxic Cry proteins of the invention. In some particular embodiments, the Cry protein of the invention is delivered orally to an insect, wherein the insect ingests one or more parts of a transgenic plant.

In other embodiments, the Cry protein of the invention is delivered orally to an insect, wherein the insect ingests one or more parts of a plant sprayed with a composition comprising the Cry proteins of the invention. Delivering the compositions of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

In some embodiments, the invention encompasses a method of providing a farmer with a means of controlling a lepidopteran insect pest, the method comprising supplying or selling to the farmer plant material such as a seed, the plant material comprising a polynucleotide, chimeric gene, expression cassette or a recombinant vector capable of expressing a Cry protein of the invention, as described above.

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

EXAMPLES

Example 1. Identification of Active Bt Strains

*Bacillus thuringiensis* isolates were cultured from spores present in current collections and maintained on T3+penicillin agar plates. Each isolate was grown aerobically in 24-well deep blocks for about 10 days at 28° C. until sporulation, which was verified by staining with Coomasie blue/acetic acid and visualization with a microscope. After sporulation both the soluble and insoluble fractions were tested for activity against lepidopteran species of interest. Fractions were tested in a surface contamination bioassay, where the fractions were overlaid onto a multispecies artificial diet. Each isolate was screened against at least four lepidopteran species, including *Helicoverpa zea* (corn earworm), *Agrotis ipsilon* (black cutworm), *Ostrinia nubilalis* (European corn borer), and *Spodoptera frugiperda* (fall armyworm) with a sample size of 12 neonate larvae. The duration of each assay was about 7 days at room temperature; the plates were scored for mortality as well as larval growth inhibition. Observed mortality at an increase of 30% over the negative control was considered active. Based on the initial insect testing, strains C0633, C2080, M0262 and M1455 were selected for further analysis.

Example 2: Isolation and Sequencing of Bt Genes

Fosmid Genomic Library Construction: For some Bt strains that were identified in Example 1, genes encoding the putatively active proteins were isolated using a fosmid library method described in Park et al. (FEMS Microbiol. Lett. 284:28-34 (2008). The fosmid library was constructed using a CopyControl™ Fosmid Library Production Kit (Epicentre, Madison, Wis.) according to the manufacturer's protocol. Briefly, purified DNA from each Bt strain (approximately 0.5 µg) was treated enzymatically to end repair the blunt ends, and was then ligated into the fosmid vector pCC1FOS (Epicentre). After in vitro packaging into lambda phages and infection of *Escherichia coli* (*E. coli*) EPI300-T1®, the bacterial cells were plated on Luria-Bertani (LB) that contained 12.5 µg/ml chloramphenicol. The plates were incubated at about 37° C. for 24 h before the selection of colonies. Transfected *E. coli* colonies were transferred to 96-well plates that contained 150 µl of chloramphenicol-containing LB medium and were incubated at 37° C. for 24 h.

Colony Hybridization Screen: A fosmid library was plated at a density of 300 cfu per 100×15 mm L-agar plus 15 µg/ml chloramphenicol plate. A total of 3000 fosmids were plated. The filter hybridizations were performed using Immobilon-Ny+87 mm filter circles (EMD Millipore, Billerica, Mass.). Colony lifts were completed as follows: filters were placed on plates for about 5 min, then using forceps, filters were lifted from the agar surface and placed colony side up on Whatman filter paper soaked with 0.5 M NaOH for 5 min. Colony filters were then placed on Whatman filter paper soaked in 2×SSC for 5 min. DNA was immobilized to the membrane with a UV Stratalinker® set at 2000×100 µJ (Stratagene, Inc., La Jolla, Calif.). The filters are then air dried on Whatman filter paper. Filters were pre-hybridized and hybridized in 250 mM NaPO$_4$, pH 7.0, 7% SDS, 1% BSA at 65° C. as described by the supplier. Hybridization filters were washed in 2×SSC, 0.5% SDS for 30 min at 65° C., followed by 0.2×SSC, 0.2% SDS for 30 min at 65° C. Filters were exposed to X-ray film (Kodak® BIOMAX® XAR, Fisher Scientific, Pittsburgh, Pa.) overnight with intensifying screens at −80° C. Positive colonies were patched to L agar with plus 15 µg/ml chloramphenicol.

Hybridization Probes: PCR primers were designed to amplify a 720 bp fragment of a cry9B-like gene from the genomic DNA of a Bt strain designated C0633. The primer pair included a forward primer designated OAR2613a having the sequence AAACATGAACCGAAATAAT-CAAAATG (SEQ ID NO:21) and a reverse primer designated OAR2615a having the sequence ATCCGTCCCTTGTGCGTGTAAA (SEQ ID NO:22). The PCR reaction was run under the following cycle conditions: [94° C., 5 min], 12×[94° C., 30 sec, 57° C. to 51° C., dropping 0.5° C. per cycle, 30 sec, 72° C. 2.5 min], and 35×[94° C., 30 sec, 52° C., 30 sec, 72° C., 2.5 min]. The reaction contained 1× One Taq® buffer (New England Biolabs, Beverly, Mass.), 200 um dNTP, 80 ng DNA, 2.5U One Taq® DNA polymerase, 50 ng each primer and sterile distilled water to 50 µl total reaction.

The resulting amplicon was separated on 1% agarose TAE gel containing ethidium bromide. The amplicon was viewed under UV light and cut out of the gel. The DNA was isolated using a gel extraction kit as described by the supplier (Qiagen, Valencia, Calif.). Probes were labeled with EasyTide (αt-32P) dCTP 3000 Ci/mmol (Perkin Elmer, Waltham, Mass.) using Rediprime II random prime labeling system (GE Healthcare, Pittsburgh, Pa.). Unincorporated nucleotides were removed using Micro Bio-Spin 30 Chromatography columns (Biorad, Hercules, Calif.). Probes were heated at 95° C. for 5 min before addition to hybridization solution.

Bt Gene Sequencing: DNA preps for 2-4 independent clones are prepped following the manufacturer's instructions (Qiagen). Sequencing reactions with primers designed to both strands of the predicted nucleotide sequence of interest were carried out using the BigDye™ Terminator Kit (Applied Biosystems, Foster City, Calif.) according to manufacturer's instructions. Reaction products were electrophoresed on ABI373 or ABI377 sequencing instruments. All sequencing data are analyzed using the Phred/Phrap/Consed software package (University of Washington) to an error ratio equal to or less than $10^{-4}$ at the consensus sequence level. The sequence was assembled with the program Sequencher™ (Version 4.7, Gene Codes Corp., Ann Arbor, Mich.). Each gene was sequenced to 4× coverage.

Example 3. Bt Gene Cloning and Synthesis

Cry9-specific primer pairs were designed to facilitate the identification and cloning of cry9-type genes. Primer pairs were designed to hybridize to a 5' end of a cry9-type gene with the addition of a PmeI restriction site and to a 3' end with the addition of an AscI restriction site. The primer pair used to amplify a 5' end included a forward primer having the sequence (SEQ ID NO: 23)
GTTTAAACATGAATCGAAATAATCAAAATG and a reverse primer having the sequence (SEQ ID NO: 24)
GGCGCGCCCTACTCTTGTGTTTCAATAAA.

The primer pair used to amplify a 3' end included a forward primer having the sequence (SEQ ID NO: 25)
GTTTAAACATGAATCAAAATAAACACGGA and a reverse primer having the sequence (SEQ ID NO: 26)
GGCGCGCCTTACTGTTGGGTTTCCATGAACT.

The inserted restriction sites are underlined in the respective primers. The PCR reactions were carried out using the following cycle conditions: [94° C., 5 min] and 30×[94° C., 30 sec, 45° C., 30 sec, 72° C., 3.5 min]. The reaction contained 1× OneTaq buffer, 200 um dNTP, 80 ng DNA, 2.5U OneTaq DNA polymerase (New England Biolabs), 50 ng each primer and sterile distilled water to 50 µl total reaction.

The resulting amplicon was cloned into the TOPO pCR 4.0 vector as described by the supplier (Life Technologies). Isolated plasmid DNA was digested with PmeI and AscI as described by the supplier (New England Biolabs).

The PmeI/AscI fragment was cloned into a shuttle vector designated pCIB5634' designed for expression in both *E. coli* and *B. thuringiensis*. The pCIB5634' vector was digested with PmeI and AscI. The digested vector and the gene fragment were purified by running on a 1% agarose Tris Acetate EDTA buffer based gel. The fragments were cutout from the gel and cleaned up using the QIAGEN gel extraction kit as described by the supplier. The fragments were ligated together using a ligation kit from New England Biolabs as described by the supplier. The ligation reaction was transformed into TOP10 cells (Life Technologies) as described by the supplier and plated on L-agar containing 100 mg/ml ampicillin. Plasmid DNA was isolated from a single colony and the identified clone was sequenced again to 2× coverage to confirm the correct sequence.

Some Bt genes that were selected for recombinant production but were not directly cloned out of genomic DNA were submitted to third party vendors for whole gene synthesis. These synthesized Bt genes were sub-cloned into the above-described shuttle vectors for subsequent expression and testing for further biological activity.

Example 4. Genome Assembly and Analysis

Some Bt genes of the invention were identified using a whole genome sequencing approach. Briefly, *Bacillus* DNA was sheared using a Covaris S2 ultrasonic device (Covaris, Inc., Woburn, Mass.) with the program DNA_400 bp set at duty cycle: 10%; intensity: 4; cycles/burst: 200. The DNA was treated with the NEBNext® Ultra™ End Repair/dA-tailing module (New England Biolabs, Inc. Ipswich, Mass.). Bioscience indexes 1-57 adapters (1-27 Brazil, 28-57 USA, UK and Switzerland) were ligated using NEB Quick Ligation™ as described by the supplier (New England Biolabs, Inc. Ipswich, Mass.). Ligations were cleaned up using Agencourt AMPure XP beads as described by the supplier (Beckman Coulter, Inc., Indianapolis, Ind.).

The library was size fractionated as follows: A 50 uL sample was mixed with 45 ul 75% bead mix (25% AMPure beads plus 75% NaCl/PEG solution TekNova cat # P4136). The mix was stirred and placed on magnetic rack. The resulting supernatant was transferred to a new well and 45 ul 50% bead mix (50% AMPure beads plus 50% NaCl/PEG solution TekNova cat # P4136) was added. This mix was stirred and placed on a magnetic rack. The resulting supernatant was removed and the beads were washed with 80% ethanol. 25 uL of elution buffer (EB) buffer was added and the mix placed on a magnetic rack. The final resulting supernatant was removed and placed in 1.5 mL tube. This method yielded libraries in the 525 DNA base pairs (bp) (insert plus adapter) size range.

The sized DNA library was amplified using KAPA Biosystem HiFi Hot Start (Kapa Biosystems, Inc., Wilmington, Mass.) using the following cycle conditions: [98° C., 45 s]; 12×[98° C., 15 s, 60° C., 30 s, 72° C., 30 s]; [72° C., 1 min]. Each reaction contained: 5 ul DNA library, 1 uL Bioscience universal primer (25 uM), 18 uL sterile water, 1 uL Bioscience indexed primer (25 uM), 25 ul 2×KAPA HiFi polymerase.

Libraries were run on the Agilent 2100 Bioanalyzer (Agilent Technologies, Santa Clara, Calif.) using High Sensitivity chips to determine the library size range and average insert size. All libraries were processed for paired end (PE) sequencing (100 cycles per read; 12-24 libraries per lane) on a HiSeq 2500 sequencing system using standard manufacturer's sequencing protocols (Illumina, Inc., San Diego, Calif.).

A *Bacillus* computational analysis tool was developed in order to identify and characterize likely toxin genes for prioritization of leads for further laboratory testing.

The genome assembly and analysis as well as the genomic library analysis described above led to the identification of four Cry9-like genes in the *Bacillus thuringiensis* strains with toxicity to at least black cutworm (*Agrotis ipsilon*). Identifying characteristics of the Cry9-like genes and proteins are shown in Table 1.

TABLE 1

Cry9-like genes identified in *Bacillus thuringiensis* strains.

| Strain | Gene/Protein Name | Molecular Weight (kD) | Nucleotide SEQ ID NO: | Amino Acid SEQ ID NO: |
|---|---|---|---|---|
| C2080 | BT0044 | 127.4 | 1 | 13 |
| C0633 | BT0051 | 129.6 | 2 | 14 |
| M0262 | BT0068 | 132.3 | 3 | 15 |
| M1455 | BT0128 | 132.7 | 4 | 16 |

Example 5. Homology of BT0044, BT0051, BT0068 and BT0128 to Known Bt Cry Proteins A search of protein databases with the amino acid sequences of the proteins of the invention reveal that they are homologous to known insecticidal proteins. Comparison of the amino acid sequences of the proteins of the invention to the non-redundant (nr) database maintained by the NCBI using the BLAST algorithm revealed the following proteins as having the strongest block of amino acid identity to the sequences of the invention (Table 2).

An equal amount of protein in solution was applied to the surface of an artificial insect diet (Bioserv, Inc., Frenchtown, N.J.) in 24 well plates. After the diet surface dried, larvae of the insect species being tested were added to each well. The

TABLE 2

Percent identity of Cry proteins of the invention with known Cry proteins.

| | Percent Identity | | | | | | | | |
|---|---|---|---|---|---|---|---|---|---|
| | Cry9Aa1 | Cry9Ba1 | Cry9Bb1 | Cry9Ca1 | Cry9Da1 | Cry9Db1 | Cry9Ea1 | CryFa1 | CryGa1 |
| 0044 | 73 | 56 | 50 | 52 | 53 | 52 | 52 | 50 | 47 |
| 0051 | 56 | 62 | 61 | 98 | 69 | 68 | 70 | 64 | 35 |
| 0068 | 54 | 70 | 77 | 69 | 66 | 68 | 69 | 62 | 36 |
| 0128 | 60 | 76 | 71 | 69 | 66 | 67 | 68 | 62 | 35 |

Example 6. Bt Protein Expression in Recombinant Host Cells

*Bacillus* Expression. Genes of interest were expressed in an acrystalliferous *Bacillus* strain with no observable coleopteran or lepidopteran activity via the pCIB5634' expression vector described above, which contains an appropriate Cry protein promoter and erythromycin resistance marker. Constructs were transformed into the host strain via electroporation and subsequent selection on erythromycin containing agar plates. These recombinant strains were grown to sporulation phase in T3 media at 28° C. for 4-5 days. Cell pellets were harvested and washed iteratively before solubilization in high pH carbonate buffer (50 mM) containing 2 mM DTT.

*E. coli* Expression. Genes of interest were expressed in various *E. coli* strains using the pET28a or pET29a vectors (EMD Millipore). Constructs were transformed by electroporation and subsequent selection on kanamycin-containing agar plates. These recombinant strains were grown and expression induced using IPTG induction at 28° C. Cells were resuspended in high pH carbonate buffer (50 mM) containing 2 mM DTT and then broken using a Microfluidics LV-1 homogenizer.

Expression Analysis. Resulting cell lysates (from either host) were then clarified via centrifugation and samples were analyzed for purity via SDS-PAGE and electropherogram (BioRad Experion). Total protein concentrations were determined via Bradford or Thermo 660 assay. Purified Cry proteins were then tested in bioassays.

Example 7. Activity of Cry Proteins in Bioassays

The proteins produced in Example 6 were tested against one or more of the following insect pest species using an art-recognized artificial diet bioassay method: fall armyworm (FAW; *Spodoptera frugiperda*), corn earworm (CEW; *Helicoverpa zea*), European corn borer (ECB; *Ostrinia nubilalis*), black cutworm (BCW; *Agrotis ipsilon*), sugarcane borer (SCB; *Diatraea saccharlis*), velvet bean caterpillar (VBC; *Anticarsia gemmatalis*), soybean looper (SBL; *Pseudoplusia includens*), southwestern corn borer (SWCB; *Diatraea grandiosella*), western bean cutworm (WBCW; *Striacosta albicosta*), tobacco budworm (TBW; *Heliothis virescens*), Asian corn borer (ACB; *Ostrinia fumacalis*), cotton bollworm (CBW; *Helicoverpa armigera*), striped stem borer (SSB; *Chilo suppressalis*), pink stem borer (PSB; *Sesamia inferens*) and rice leaf folder (RLF; *Cnaphalocrocis medinails*).

plates were sealed and maintained at ambient laboratory conditions with regard to temperature, lighting and relative humidity. A positive-control group consisted of larvae exposed to a very active and broad-spectrum wild-type *Bacillus* strain. Negative control groups consisted of larvae exposed to insect diet treated with only the buffer solution and larvea on untreated insect diet; i.e. diet alone. Mortality was assessed after about 120 hours and scored relative to the controls.

Results are shown in Table 3, where a "−" means no activity compared to check, a "+/−" means 0-10% activity compared to check (this category also includes 0% mortality with strong larval growth inhibition), a "+" means 10-25% activity compared to check, a "++" means 25-75% activity compared to check, and a "+++" 75-100% activity compared to check.

TABLE 3

Results of bioassay with Cry Proteins.

| | BT Proteins | | | |
|---|---|---|---|---|
| Insect | 0044 | 0051 | 0068 | 0128 |
| FAW | − | − | − | − |
| CEW | + | − | − | + |
| ECB | − | +++ | − | +/− |
| BCW | + | +++ | +++ | +++ |
| SCB | +/− | +++ | − | +/− |
| VBC | | +++ | +++ | +++ |
| SBL | | − | +++ | +++ |
| SWCB | − | +++ | + | ++ |
| WBCW | − | − | | |
| TBW | | | +++ | +++ |
| ACB | | +++ | | |
| CBW | | +/− | | |
| SSB | | + | | |
| PSB | | + | | |
| RLF | | +++ | | |

Example 8. Fate of Cry Proteins in Simulated Gastric Fluid Assay

Certain Cry proteins have been expressed in plants and seed from such plants are sold annually to farmers for use in controlling various insect pests. Such self-protected pesticidal products are subject to review and registration by various regulatory agencies including, for example, the US Environmental Protection Agency (EPA).

Dietary exposure is the major route by which humans can be exposed to Cry proteins expressed in transgenic plants. Acute oral mammalian toxicity and protein digestibility are the end points for EPA's human health risk assessment. Further scientific evidence of the safety of Cry proteins is that they have been shown to be rapidly degraded in vitro using simulated gastric fluids. Results of seven in vitro assays conducted with representative Cry1, Cry2, and Cry3 proteins establish that the proteins are rapidly degraded, typically within 30 seconds. These results support the broader conclusion that members of these groups of Cry proteins (that share significant amino acid sequence identity) are likely to be rapidly degraded following ingestion by humans. Another area of consideration is whether Cry proteins may induce an allergenic reaction. The demonstrated rapid in vitro degradation of Cry proteins should minimize the potential for such an occurrence. By comparison, food allergens generally persisted in the in vitro gastrointestinal model, whereas common food proteins with no allergenic history degraded rapidly in simulated gastric fluid (Metcalfe et al. 1996).

Additional insights into the potential allergenicity of a protein can be gained through an analysis of the protein's digestibility in simulated gastric fluid (SGF). Almost all Cry proteins expressed in transgenic plants that have been tested to date are rapidly digested and therefore have been determined to be non-allergenic. However, a Cry9C protein found in the transgenic corn product known as Starlink was found to be partially stable to SGF. Although Starlink Cry9C is not toxic to animals, the properties of partial digestibility and partial processing stability made it difficult for the EPA to absolutely preclude the possibility that the Starlink Cry9C protein could act a food allergen ultimately leading the company that developed Starlink to recall products from the US market.

Currently, no definitive tests for determining the allergenic potential of novel proteins exist. Therefore, EPA uses a weight-of-evidence approach where the following factors are considered: source of the trait; amino acid sequence comparison with known allergens; and biochemical properties of the protein, including in vitro digestibility in simulated gastric fluid (SGF) and glycosylation.

A simulated gastric fluid (SGF) assay measures the in vitro digestibility of a test protein at tightly controlled conditions representative of the upper mammalian digestive tract. In brief, bacterially produced test Cry protein (at a concentration of 0.5-5 mg/ml) was exposed to the enzyme pepsin (from porcine gastric mucosa, solubilized in 2 mg/ml NaCl, pH 1.2) at a ratio of 10 Units of pepsin activity/μg test protein over a time period of one hour at 37° C. Samples are removed at 1, 2, 5, 10, 30, and 60 minutes and immediately quenched with the addition of pre-heated (95° C.-2 minutes) stop buffer (65% 0.5M Sodium Bicarbonate pH 11, 35% Tricine Loading Buffer) to immediately render pepsin inactive, and returned to heat for an additional 5 minutes. Once the assay was complete, time point samples and controls (test protein alone, pepsin alone) were examined by SDS-PAGE on a 10-20% Tris-Tricine gel (with peptides visible down to 1 kDa) to track the kinetics and level of digestion performed by pepsin.

Results of the SGF assays demonstrated that all of the Cry proteins of the invention were degraded very rapidly. These results provide evidence that although the Cry proteins of the invention are related to the Cry 9 protein family, they are quite different in their response to the SGF assay compared to certain published results, for example Cry9C in Starlink, suggesting significant structural differences at key pepsin cleavage sites in the protein. These results further suggest that the potential for the Cry proteins of the invention to be allergenic is minimal.

Example 9. Mutagenesis of BT-0051

Prediction of antigenic regions in a protein is helpful for a rational approach to the synthesis of peptides which may elicit antibodies reactive with the intact protein and differentiate closely related proteins. For this example, the amino acid sequence of the native BT-0051 (SEQ ID NO:6) was superimposed onto the crystal structure of a Cry8Ea1 protein (Accession No. 3EB7; Protein Databank at worldwide web-scsb.org/pdb/; See also Berman et al., 2000. Nuc. Acids Res. 28:235-242) and predicted antigenic regions using the Vector NTI 8.0 (Thermo Fisher Scientific, Inc., Waltham, Mass.; See also Welling et al. 1985. FEBS Lett. 188:215-218) were mapped onto the structure. Selection of a suitable mutagenic region consisted of choosing loop domains in non-conserved regions outside of domain I. Loops known to be involved in Cry protein receptor recognition were eliminated from selection as were any residues predicted to be involved in protease activation. This left one region for mutagenesis represented by amino acids 342-354 of SEQ ID NO:6. Changes L350I, N351Q, and T354S were chosen (SEQ ID NO: 18) based on the expectation that they would result in minimal structural change or functional change relative to the native BT-0051. Such changes produce an antigenic region that allows the mutant BT-0051 (mBT-0051; SEQ ID NO:18) to be distinguished from native BT-0051 (SEQ ID NO:14) and from other related Cry9 proteins.

Example 10. Vectoring of Genes for Plant Expression

Prior to expression in plants, a synthetic polynucleotide comprising a nucleotide sequence encoding each of the Bt Cry proteins, BT-0044, BT-0051, BT-0068 and BT-0128 (SEQ ID NOs:5-8, respectively), and a synthetic polynucleotide comprising a nucleotide sequence encoding each of the mutant Bt Cry proteins, mBT-0044, mBT-0051, mBT-0068 and mBT-0128 (SEQ ID NOs:17-20, respectively) is synthesized on an automated gene synthesis platform (Genscript, Inc., Piscataway, N.J.). For this example, a first expression cassette is made comprising a maize ubiquitin promoter (Ubi1) operably linked to the Cry protein coding sequence which is operably linked to a NOS terminator and a second expression cassette is made comprising a Ubi1 promoter operably linked to a phosphomannose isomerase (PMI) coding sequence which is operably linked to a NOS terminator. Expression of PMI allows for positive selection of transgenic plants on mannose. Both expression cassettes are cloned into a suitable vector for *Agrobacterium*-mediated maize transformation.

Example 11. Expression of Cry Proteins in Plants

Transformation of immature maize embryos is performed essentially as described in Negrotto et al., 2000, Plant Cell Reports 19: 798 803. Briefly, *Agrobacterium* strain LBA4404 (pSB1) comprising a vector described in Example 12 is grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* cells are suspended in LS-inf media supplemented with 100 μM As. Bacteria are pre-induced in this medium for approximately 30-60 minutes.

Immature embryos from an inbred maize line are excised from 8-12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/l) and silver nitrate (1.6 mg/l) and cultured in the dark at approximately 28° C. for 10 days.

Immature embryos, producing embryogenic callus are transferred to LSD1M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the PMI genes and the Bt cry gene by PCR. Positive plants from the PCR assay are transferred to a greenhouse for further evaluation.

Transgenic plants are evaluated for copy number (determined by Taqman analysis), protein expression level (determined by ELISA), and efficacy against insect species of interest in leaf excision bioassays. Specifically, leaf tissue is excised from single copy events (V3-V4 stage) and infested with neonate larvae, then incubated at room temperature for 5 days. Sample size for leaf disk bioassay varies depending on the insect species tested (European corn borer (ECB), n=10; corn earworm (CEW), n=3, black cutworm (BCW), n=5). Readings to assess tissue damage and mortality are taken at approximately day 3 and day 5; samples are rated for damage relative to the negative control using the following scale: "+": <5% tissue damage, all larvae dead; "+/−": 5-20% tissue damage, all larvae dead; or "−": >20% tissue damage, some larvae alive and/or progressing to $2^{nd}$ instar.

Results of the transgenic plant tissue bioassay confirm that the Cry proteins of the invention when expressed in transgenic plants are toxic to target insects. For example, mBT-0051 expressed in maize stably transformed with a chimeric gene of the invention is active against at least black cutworm (*Agrotis ipsilon*) as well as Asian corn borer (*Ostrinia furnacalis*), striped stem borer (*Chilo suppressalis*)\ and cotton bollworm (*Helicoverpa armigera*).

What is claimed is:

1. A chimeric gene comprising a heterologous promoter operably linked to a nucleic acid molecule comprising a nucleotide sequence that (a) encodes an insecticidal protein comprising an amino acid sequence that has at least 99% sequence identity with SEQ ID NO:16; or (b) encodes a protein comprising SEQ ID NO:16; or (c) is a synthetic sequence of (a) or (b) that has codons optimized for expression in a transgenic organism.

2. The chimeric gene of claim 1, wherein the heterologous promoter is a plant expressible promoter.

3. The chimeric gene of claim 2, wherein the plant expressible promoter is selected from the group consisting of ubiquitin, cmp, corn TrpA, bacteriophage T3 gene 9 5' UTR, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

4. The chimeric gene of claim 1, wherein the insecticidal protein is toxic to at least black cutworm (*Agrotis ipsilon*).

5. The chimeric gene of claim 1, wherein the synthetic sequence comprises SEQ ID NO:8.

6. A recombinant vector comprising the chimeric gene of claim 1.

7. A transgenic plant comprising the chimeric gene of claim 1.

8. Seed of the transgenic plant of claim 7, wherein said seed comprises the chimeric gene.

9. A harvested product derived from the transgenic plant of claim 7, wherein the harvested product comprises the chimeric gene or a protein encoded by the chimeric gene.

10. An extract from the transgenic plant of claim 7, wherein the extract comprises the chimeric gene or a protein encoded by the chimeric gene.

11. A method of producing an insect-resistant transgenic plant, comprising: introducing into a plant the chimeric gene of claim 1, wherein the insecticidal protein is expressed in the plant, said protein conferring to the plant resistance to an insect pest, and thereby producing an insect-resistant transgenic plant.

12. The method of claim 11, wherein the introducing step is achieved by (a) transforming the plant; or (b) crossing a first plant comprising the chimeric gene with a different second plant.

13. A method of controlling at least black cutworm (*Agrotis ipsilon*), comprising delivering to the insect pest an effective amount of an insecticidal protein encoded by the chimeric gene of claim 1.

14. A synthetic nucleic acid molecule comprising a nucleotide sequence that encodes an insecticidal protein and that has codons optimized for expression in a transgenic organism, wherein the nucleotide sequence (a) comprises SEQ ID NO:8; or (b) encodes an amino acid sequence that has at least 99% identity with SEQ ID NO:16.

15. The synthetic nucleic acid molecule of claim 14, wherein the nucleotide sequence encodes SEQ ID NO:16.

16. The chimeric gene of claim 1, wherein the nucleotide sequence comprises SEQ ID NO:4.

\* \* \* \* \*